US008299218B2

(12) United States Patent
Marks et al.

(10) Patent No.: US 8,299,218 B2
(45) Date of Patent: Oct. 30, 2012

(54) THERAPEUTIC MONOCLONAL ANTIBODIES THAT NEUTRALIZE BOTULINUM NEUROTOXINS

(75) Inventors: James D. Marks, Kensington, CA (US); Ali Razai, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 353 days.

(21) Appl. No.: 12/468,526

(22) Filed: May 19, 2009

(65) Prior Publication Data

US 2009/0324606 A1 Dec. 31, 2009

Related U.S. Application Data

(60) Division of application No. 10/632,706, filed on Aug. 1, 2003, now Pat. No. 7,563,874, which is a continuation-in-part of application No. 09/144,886, filed on Aug. 31, 1998, now abandoned.

(60) Provisional application No. 60/400,721, filed on Aug. 1, 2002.

(51) Int. Cl.
*C07K 16/00* (2006.01)
*C12P 21/08* (2006.01)
*G01N 33/53* (2006.01)

(52) U.S. Cl. ............. 530/387.1; 530/388.15; 530/388.1; 530/389.1; 530/389.5; 435/7.1

(58) Field of Classification Search ........................ None
See application file for complete search history.

(56) References Cited

U.S. PATENT DOCUMENTS

| | | | |
|---|---|---|---|
| 4,689,299 A | 8/1987 | Insel et al. | |
| 5,306,730 A | 4/1994 | Nagai et al. | |
| 5,599,539 A | 2/1997 | Carroll et al. | |
| 5,719,267 A | 2/1998 | Carroll et al. | |
| 5,731,161 A | 3/1998 | Aoki et al. | |
| 5,807,741 A | 9/1998 | Brown et al. | |
| 5,919,665 A | 7/1999 | Williams | |
| 5,932,449 A | 8/1999 | Emanuel et al. | |
| 6,331,402 B1 | 12/2001 | Nussbaum et al. | |
| 6,416,947 B1 | 7/2002 | Balasubramanian et al. | |
| 6,461,617 B1 | 10/2002 | Shone et al. | |
| 6,495,143 B2 | 12/2002 | Lee et al. | |
| 6,656,468 B1 | 12/2003 | Carroll et al. | |
| 6,667,158 B1 | 12/2003 | Bavari et al. | |
| 6,730,324 B2 | 5/2004 | Troczynski et al. | |
| 6,762,280 B2 | 7/2004 | Schmidt et al. | |
| 6,794,128 B2 | 9/2004 | Marks et al. | |
| 6,841,156 B2 | 1/2005 | Aoki et al. | |
| 6,932,449 B2 | 8/2005 | Collins et al. | |
| 7,081,529 B2 | 7/2006 | Smith et al. | |
| 7,157,562 B1 | 1/2007 | Olsen, II et al. | |
| 7,192,596 B2 | 3/2007 | Shone et al. | |
| 7,214,787 B1 | 5/2007 | Smith et al. | |
| 7,244,826 B1 | 7/2007 | Marks et al. | |
| 7,332,580 B2 | 2/2008 | Adams et al. | |
| 7,332,585 B2 | 2/2008 | Adams et al. | |
| 7,341,843 B2 | 3/2008 | Atassi | |
| 7,563,874 B2 | 7/2009 | Marks et al. | |
| 7,700,738 B2 * | 4/2010 | Marks et al. | ................ 530/387.1 |
| 7,999,079 B2 * | 8/2011 | Marks et al. | ................ 530/387.1 |
| 2002/0155114 A1 | 10/2002 | Marks et al. | |
| 2004/0009172 A1 | 1/2004 | Fischkoff et al. | |
| 2004/0175385 A1 | 9/2004 | Marks et al. | |
| 2004/0265935 A1 | 12/2004 | Atassi | |
| 2005/0147610 A1 | 7/2005 | Ghayur et al. | |
| 2006/0147471 A1 | 7/2006 | Borodic et al. | |
| 2006/0246071 A1 | 11/2006 | Green et al. | |
| 2006/0251658 A1 | 11/2006 | Ledbetter et al. | |
| 2008/0124328 A1 | 5/2008 | Marks et al. | |
| 2009/0123481 A1 * | 5/2009 | Marks et al. | ................ 424/164.1 |
| 2010/0166773 A1 * | 7/2010 | Marks et al. | ................ 424/167.1 |
| 2010/0203559 A1 * | 8/2010 | Ester et al. | ................... 435/7.92 |
| 2011/0171235 A1 * | 7/2011 | Marks et al. | ................ 424/164.1 |
| 2011/0200615 A1 * | 8/2011 | Marks et al. | ................ 424/167.1 |

FOREIGN PATENT DOCUMENTS

| | | |
|---|---|---|
| EP | 0578515 A2 | 1/1994 |
| EP | 1850866 A1 | 11/2009 |
| WO | 94/10332 | 5/1994 |
| WO | 96/25669 | 8/1996 |
| WO | 99/56129 | 11/1999 |
| WO | 00/69891 | 11/2000 |
| WO | 00/69895 | 11/2000 |
| WO | 01/19992 | 3/2001 |
| WO | 03/057857 | 7/2003 |
| WO | 2004/106376 | 12/2004 |
| WO | 2005/016232 | 2/2005 |
| WO | 2005/084361 | 9/2005 |
| WO | 2005/118635 | 12/2005 |
| WO | 2007/094754 | 8/2007 |
| WO | 2008/097866 | 8/2008 |
| WO | WO 2009/096162 * | 8/2009 |
| WO | WO 2009105150 | 8/2009 |
| WO | WO 2009/114748 A1 * | 9/2009 |
| WO | WO 2009131605 | 10/2009 |
| WO | WO 2010/014854 * | 2/2010 |

OTHER PUBLICATIONS

Thanongsaksrikul et al, Toxins, 2011, 3:469-488.*
Marks, Movement Disorders, 2004, vol. 19, Suppl 8:S101-S108.*
Garcia-Rodriguez et al, Protein Egineering, Design & Selection, 20011, 24/3:321-331.*
Scotcher et al, Hybridoma, 2009, 28/5:315-325.*
Paul, Fundamental Immunology, 3rd Edition, 1993, pp. 292-295.*
Rudikoff et al, PNAS, USA, Mar. 1982, 79/6:1979-1983.*
Colman, Research in Immunology, 1994, 145:33-36.*
Bendig (Methods: A Companion to Methods in Enzymology 1995; 8:83-93).*
Padlan et al. (PNAS 1989, 86:5938-5942).*

(Continued)

*Primary Examiner* — Nita M Minnifield
(74) *Attorney, Agent, or Firm* — Carol L. Francis; Bozicevic, Field & Francis LLP

(57) ABSTRACT

This invention provides antibodies that specifically bind to and neutralize botulinum neurotoxin type A (BoNT/A) and the epitopes bound by those antibodies. The antibodies and derivatives thereof and/or other antibodies that specifically bind to the neutralizing epitopes provided herein can be used to neutralize botulinum neurotoxin and are therefore also useful in the treatment of botulism.

22 Claims, 10 Drawing Sheets

OTHER PUBLICATIONS

Middlebrook et al., Immunodiagnosis and immunotherapy of tetanus and botulinum neurotoxins. Curr. Top. Microbiol. Immunol. 1995;195:89-122.

Montecucco, How do tetanus and botulinum toxins bind to neuronal membranes? Trends Biochem. Sci. 1986;11:314-7.

Montecucco et al, Structure and function of tetanus and botulinum neurotoxins. Q. Rev. Biophys. 1995;28(4): 423-72.

Montero-Julian et al., Pharmacokinetic study of anti-interleukin-6 (IL-6) therapy with monoclonal antibodies: enhancement of IL-6 clearance by cocktails of anti-IL-6 antibodies. Blood 1995;85(4):917-24.

Mullaney et al., Epitope mapping of neutralizing botulinum neurotoxin A antibodies by phage display. Infect. Immun. 2004;69(10):6511-4.

Nowakowski et al., Potent neutralization of botulinum neurotoxin by recombinant oligoclonal antibody. Proc. Natl. Acad. Sci. USA, 2002;99(17):11346-50.

Oguma et al., Infant botulism due to Clostridium botulinum type C toxin. Lancet 1990;336(8728):1449-50.

Pless et al., High-affinity, protective antibodies to the binding domain of botulinum neurotoxin type A. Infect. Immun. 2001;69(1):570-4.

Reichert, Monoclonal antibodies in the clinic. Nat. Biotechnol. 2001;19(9):819-22.

Schengrund, What is the cell surface receptor(s) for the different serotypes of botulinum neurotoxin? J Toxicol Toxin Rev., 1999;18:35-44.

Schiavo et al., Tetanus and botulinum-B neurotoxins block neurotransmitter release by proteolytic cleavage of synaptobrevin. Nature 1992;359(6398):832-5.

Schiavo et al., Identification of the nerve terminal targets of botulinum neurotoxin serotypes A, D, and E. J. Biol. Chem. 1993;268(32):23784-7.

Schier et al., In vitro and in vivo characterization of a human anti-c-erbB-2 single-chain Fv isolated from a filamentous phage antibody library. Immunotechnology 1995;1(1):73-81.

Siegel, Human immune response to botulinum pentavalent (ABCDE) toxoid determined by a neutralization test and by an enzyme-linked immunosorbent assay. J. Clin. Microbiol. 1988;26(11):2351-6.

Simpson, Kinetic studies on the interaction between botulinum toxin type A and the cholinergic neuromuscular junction. J. Pharmacol. Exp. Ther. 1980;212(1):16-21.

Sonnabend et al., Isolation of Clostridium botulinum type G and identification of type G botulinal toxin in humans: report of five sudden unexpected deaths. J. Infect. Dis., 1981;143(1):22-7.

Tacket et al, Equine antitoxin use and other factors that predict outcome in type A foodborne botulism. Am. J. Med., 1984;76(5):794-8.

Volk et al., Neutralization of tetanus toxin by distinct monoclonal antibodies binding to multiple epitopes on the toxin molecule. Infect. Immun. 1984;45(3):604-9.

Williams et al., Radioiodination of botulinum neurotoxin type A with retention of biological activity and its binding to brain synaptosomes. Eur. J. Biochem 1983;131(2):437-45.

Zwick et al., Neutralization synergy of human immunodeficiency virus type 1 primary isolates by cocktails of broadly neutralizing antibodies. J. Virol. 2004;75(24):12198-208.

PCT/US06/03070 International Search Report and Written Opinion dated Aug. 3, 2007.

WO 2005/16232, International Search Report and Written Opinion dated Jul. 14, 2005.

Amersdorfer et al., Phage libraries for generation of anti-botulinum scFv antibodies. Meth. Mol Biol. 2000;145: 219-40.

Baldwin et al., Characterization of the antibody response to the receptor binding domain of botulinum neurotoxin serotypes A and E. Infect. Immun. 2005;73(10):6998-7005.

Bartels et al., Specific antibodies against the Zn(2+)-binding domain of clostridial neurotoxins restore exocytosis in chromaffin cells treated with tetanus or botulinum A neurotoxin. J Biol Chem. 1994;269(11): 8122-7.

Bavari et al., Identifying the principal protective antigenic determinants of type A botulinum neurotoxin. Vaccine 2002;20:1640-8.

Behzod et al., Immune recognition of botulinum neurotoxin B: Antibody-binding regions on the heavy chain of the toxin. Mol Immunol. 2007 [Sep. 24, 2007 Epub ahead of print].

Dixit et al., Characterization of Clostridium sp. RKD producing botulinum-like neurotoxin. Systematic and Applied Microbiology 2005;28:405-14.

Dixit et al., Development of an immunodetection test for a botulinum-like neurotoxin produced by Clostridium sp. Indian J Med Res. 2006;124(3):355-62.

Doellgast et al., Sensitive enzyme-linked immunosorbent assay for detection of Clostridium botulinum neurotoxins A, B, and E using signal amplification via enzyme-linked coagulation assay. J. Clin. Microbiol. 1993;31 (9):2402-9.

Doellgast et al., Sensitive assay for measurement of antibodies to Clostridium botulinum neurotoxins A, B, and E: use of hapten-labeled-antibody elution to isolate specific complexes. J. Clin. Microbiol., 1997;35(3):578-83.

Garcia et al., Molecular evolution of antibody specificity and cross reactivity for type A botulinum neurotoxins. Nature Biotech. 2007;25:107-16.

Hall et al., Novel Application of an in vitro technique to the detection of quantification of botulinum neurotoxin antibodies. J. Immunological Methods 2004;288:55-60.

Levy et al., Fine and domain-level epitope mapping of botulinum neurotoxin type A neutralizing antibodies by yeast surface display. J. Mol. Biol. 2007;365:196-210.

Lipps et al., Antigenic cross reactivity among the venoms and toxins from unrelated diverse sources. Toxicon. 2000; 38(7):973-80.

O'Connell et al., Production of a recombinant antibody fragment in whole insect larvae. Mol Biotechnol. 2007;36 (1):44-51.

Oshima et al., Immune recognition of botulinum neurotoxin type A: regions recognized by T cells and antibodies against the protective H(C) fragment (residues 855-1296) of the toxin. Molecular Imm. 1997;34(14):1031-40.

Palys et al., Conversion of a mouse Fab into a whole humanized IgG antibody for detecting botulinum toxin. Hum Antibodies 2006;15(4):125-32.

Park et al. (2003) Immunologic characterization of spasmodic dysphonia patients who develop resistance to botulinum toxin. J Voice. 17(2): 255-264.

Schmidt et al., Botulinum neurotoxin serotype F: identification of substrate recognition requirements and development of inhibitors with low nanomolar affinity. Biochemistry 2005;44(10):4067-73.

Sharma et al., Detection of type A, B, E, and F Clostridium botulinum neurotoxins in foods by using an amplified enzyme-linked immunosorbent assay with digoxigenin-labeled antibodies. Appl Environ. Microbiol., 2006;72(2):1231-8.

Tsuzuki et al., Establishment of a monoclonal antibody recognizing an antigenic site common to Clostridium botulinum type B, C1, D, and E toxins and tetanus toxin. Infect. Immun., 1988;56(4):898-902.

Wu et al., Characterization of neutralizing antibodies and identification of neutralizing epitope mimics on the Clostridium botulinum neurotoxin type A. Applied and Environmental Microbiology 2001;67(7):3201-7.

Ferreira et al., Monoclonal antibody to type F Clostridium botulinum toxin. Appl Environ Microbiol. 1990;56(3): 808-11.

Oguma et al., Four different monoclonal antibodies against type C1 toxin of Clostridium botulinum. Infect. Immun. 1982;38(1):14-20.

Oguma et al., Analysis of antigenicity of Clostridium botulinum type C1 and D toxins by polyclonal and monoclonal antibodies. Infect Immun. 1984;43(2):584-8.

Levy et al., Early onset of somatic mutation in immunoglobulin VH genes during the primary immune response. J. Exp. Med. 1989;169:2007-19.

Weigert et al., Rearrangement of genetic information may produce immunoglobulin diversity. Nature 1978;276:785-90.

Caton et al., Structural and functional implications of a restricted antibody response to a defined antigenic region on the influenza virus hemagglutinin. EMBO Journal 1986;5(7):1577-87.

Lebecque et al., Boundaries of somatic mutation in rearranged immunoglobulin genes: 5' boundary is near the promoter, and 3' boundary is approximately 1 kb from V(D)J gene. J. Exp. Med. 1990;172:1717-27.

McKean et al., Mechanisms of antibody diversity: multiple genes encode structurally related mouse kappa variable regions. PNAS 1978;75(8):3913-7.

Arndt et al., The structure of the neurotoxin-associated protein HA33/A from Clostridium botulinum suggests a reoccurring beta-trefoil fold in the progenitor toxin complex. J. Mol. Biol. 2005;346(4):1083-93.

Office action dated Dec. 22, 2006 from U.S. Appl. No. 10/632,706.

Office action dated Dec. 23, 2005 from U.S. Appl. No. 10/632,706.

Rudikoff et al., Single amino acid substitution altering antigen-binding specificity. PNAS 1982;79(6):1979-83.

Colman, Effects of amino acid changes on antibody-antigen interactions. Research in Immunology 1994;145:33-6.

MacCallum et al, Antibody-antigen Interactions: Contact Analysis and Binding Site Topography. J Mol Biol 1996;262:732-45.

Casset et al., A peptide mimetic of an anti-CD4 monoclonal antibody by rational design. Biochem Biophys Res Comm 2003;307:198-205.

Berzofsky et al., Chapter 8: Immunogenicity and Antigen Structure. In Fundamental Immunology 3rd edition, William E Paul ed. 1993, p. 242.

Bendig, Humanization of rodent monoclonal antibodies by CDR grafting. Methods: A companion to methods in enzymology 1995;8:83-93.

Mah et al., Recombinant anti-botulinum neurotoxin A single-chain variable fragment antibody generated using a phage display system. Hybridoma and Hybridomics 2003;22(5):277-83.

Marks et al., Deciphering antibody properties that lead to potent botulinum neurotoxin neutralization. Movement Disorders 2004;19(Supp 8):S101-8.

Kozaki et al., Immunological characterization of the neurotoxin produced by Clostridium botulinum type A associated with infant botulism in Japan. Microbiol. Immunol. 1995;39(10):767-74.

Coleman et al. Faseb Journal 2004;18(8-Supp S):C174, Meeting abstract, Abstract Only.

Smith et al., Sequence variation within botulinum neurotoxin serotypes impacts antibody binding and neutralization. Infection and Immunity, 2005;73(9):5450-7.

Razai et al., Molecular evolution of antibody affinity for sensitive detection of botulinum neurotoxin type A. J. Mol. Biol. 2005;351(1):158-69.

Schier et al., Isolation of picomolar affinity anti-c-erbB-2 single-chain Fv by molecular evolution of the complementarity determining regions in the center of the antibody binding site. J. Mol. Biol. 1996;263(4):551-67.

Shone et al., Monoclonal antibody-based immunoassay for type a Clostridium botulinum toxin is comparable to the mouse bioassay. Appl. Environ. Microbiol., 1985;50(1):63-7, abstract only.

Almquist et al., Expression of an anti-botulinum toxin a neutralizing single-chain Fv recombinant antibody in transgenic tobacco. Vaccine 2006;24(12):2079-86.

Emanuel et al., Recombinant antibodies: a new reagent for biological agent detection. Biosensors and Bioelectronics 2000;14(10-11)151-9.

Bavari et al., Identifying the principal protective antigenic determinants of type A botulinum neurotoxin. Vaccine 1998;16(19):1850-6.

Mowry et al., Production and purification of a chimeric monoclonal antibody against botulinum neurotoxin serotype A. Protein Expression and Purification 2004;37(2):399-408.

Amersdorfer et al., Molecular characterization of murine humoral immune response to botulinum neurotoxin type A binding domain as assessed by using phage antibody libraries. Infect. Immun. 1997;65(9):3743-52.

Amersdorfer et al., Genetic and immunological comparison of anti-botulinum type A antibodies from immune and non-immune human phage libraries. Vaccine 2002;20(11-12):1640-8.

Arnon, in Botulinum and Tetanus Neurotoxins: Neurotransmission and Biomedical Aspects. Ed. DasGupta, B. R. Plenum, New York; 1993:477-82.

Arnon et al., Botulinum toxin as a biological weapon: medical and public health management. J. Am. Med. Assoc. 2001;285(8):1059-1070.

Atassi et al., Mapping of the antibody-binding regions on botulinum neurotoxin H-chain domain 855-1296 with antitoxin antibodies from three host species. J. Protein Chem. 1996;15(7):691-700.

Black et al., Hypersensitivity reactions associated with botulinal antitoxin. Am. J. Med. 1980;69:567-70.

Black et al., Interaction of 125I-labeled botulinum neurotoxins with nerve terminals. I. Ultrastructural autoradiographic localization and quantitation of distinct membrane acceptors for types A and B on motor nerves. J. Cell Biol. 1986;103(2):521-534.

Bowmer, Preparation and assay of the international standards for Clostridium botulinum types A, B, C, D and E antitoxins. Bull. W. H. O. 1963;29:701-9.

Byrne et al., Development of vaccines for prevention of botulism. Biochimie 2000;82(9-10):955-66.

Chen et al., Antibody mapping to domains of botulinum neurotoxin serotype A in the complexed and uncomplexed forms. Infect. Immun. 1997;65(5)1626-30.

Chen et al., Biophysical characterization of the stability of the 150-kilodalton botulinum toxin, the nontoxic component, and the 900-kilodalton botulinum toxin complex species. Infect. Immun. 1998;66(6):2420-5.

Colcher et al., In vivo tumor targeting of a recombinant single-chain antigen-binding protein. J. Natl. Cancer Inst. 1990;82(14):1191-7.

Daniels-Holgate et al., Productive and non-productive binding of botulinum neurotoxin A to motor nerve endings are distinguished by its heavy chain. J. Neurosci. Res. 1996;44(3):263-71.

Demarchi et al., Existence of type D botulism in man. Bull. Acad. Nat. Med. 1958;142(21-2):580-2.

Dolly et al., Acceptors for botulinum neurotoxin reside on motor nerve terminals and mediate its internalization. Nature 1984;307(5950):457-60.

Emanuel et al.,Directing antigen specificity towards botulinum neurotoxin with combinatorial phage display libraries. J. Immunol. Meth. 1996;193(2):189-97.

Fitzsimmons et al., Inhibition of tetanus toxin fragment C binding to ganglioside G(T1b) by monoclonal antibodies recognizing different epitopes. Vaccine 2000;19(1):114-21.

Foote et al., Kinetic maturation of an immune response. Nature 1991;352(6335):530-2.

Fotinou et al., The crystal structure of tetanus toxin Hc fragment complexed with a synthetic GT1b analogue suggests cross-linking between ganglioside receptors and the toxin. J. Biol. Chem. 2001;276(34):32274-81.

Franz et al., in Botulinum and Tetanus Neurotoxins: Neurotransmission and Biomedical Aspects. Ed. DasGupta, B. R. Plenum, New York, 1993:473-6.

Gibson et al., Evaluation of a monoclonal antibody-based immunoassay for detecting type B Clostridium botulinum toxin produced in pure culture and an inoculated model cured meat system. J. Appl. Bacteriol. 1988;64(4):285-91.

Gill, Bacterial toxins: a table of lethal amounts. Microbiol. Rev. 1982;46(1):86-94.

Hallis et al., In Botulinum and Tetanus Neurotoxins: Neurotransmission and Biomedical Aspects. Ed. DasGupta, B. R., Plenum, New York. 1993):433-6.

Hatheway et al.,Antitoxin levels in botulism patients treated with trivalent equine botulism antitoxin to toxin types A, B, and E. J. Infect. Dis. 1984;150(3):407-12.

Hatheway, Botulism: the present status of the disease. Curr. Top. Microbio. Immunol. 1995;195: 55-75.

Hatheway et al., In Therapy with Botulinum Toxin. Ed. Jankovic, J., Dekker, New York 1994:93-107.

Hibbs et al.,Experience with the use of an investigational F(ab')2 heptavalent botulism immune globulin of equine origin during an outbreak of type E botulism in Egypt. Clin. Infect. Dis. 1996;23(2):337-40.

Hildebrand. Proc. Soc. Exp. Biol. Med. 1961;107:284-9.

Huston et al., Single-chain Fv radioimmunotargeting. J. Nucl. Med. 1996;40(3):320-33.

Koriazova et al., Translocation of botulinum neurotoxin light chain protease through the heavy chain channel. Nat. Stud. Biol. 2003;10(1):13-8.

Kozaki et al., The use of monoclonal antibodies to analyze the structure of Clostridium botulinum type E derivative toxin. Infect. Immun., 1986;52(3):786-91.

Kozaki et al., Characterization of Clostridium botulinum type B neurotoxin associated with infant botulism in japan. Infect. Immun. 1998;66(10):4811-6.

Lacy et al., Sequence homology and structural analysis of the clostridial neurotoxins. J. Mol. Biol. 1999;291 (5):1091-104.

Lacy et al., Crystal structure of botulinum neurotoxin type A and implications for toxicity. Nat. Struct. Biol. 1998;5 (10):898-902.

Lang et al., Immunotherapy with human monoclonal antibodies. Fragment A specificity of polyclonal and monoclonal antibodies is crucial for full protection against tetanus toxin.J. Immunol. 1993;151(1):466-72.

Mahant et al., The current use of botulinum toxin. J. Clin. Neurosci. 2000;7(5):389-94.

Middlebrook et al., Botulinum Toxins, chapter 33, in Medical Aspects of Chemical and Biological Warfare. Eds. Sidell, Takafuji and Franz, TMM publications, Washington D.C. 1997.

Stark et al., Antibodies that are specific for a single amino acid interchange in a protein epitope use structurally distinct variable regions. J. Exp. Med 1991;174(3):613-24.

U.S. Appl. No. 13/175,628, filed Jul. 1, 2011, Marks et al.

Boder, et al. (2000) "CDR loops can be grafted onto a different scFV framework without loss of affinity" Proc. Natl. Acad. Sci. USA 97:10701-10705.

Boles, et al. (2006) "Recombinant C Fragment of Botulinum Neurotoxin B Serotype (rBoNTB (HC)) Immune Response and Protection in the Rhesus Monkey" Toxicon 47(8):877-884.

Gonzales, et al. (2005) "grafting of murine complementarity determining regions (CDRs) onto the variable light and variable heavy frameworks of human immunoglobulin molecules" Tumour Biol. 26:31-43.

Jung & Plückthun (1997) "Improving in Vivo Folding and Stability of a Single-Chain Fv Antibody Fragment by Loop Grafting" Protein Eng. 10(8):959-66.

McHeyzer-Williams (1993) "B Lymphocyte Biology" Fundamental Immunology, 3rd Edition, Ed. William E. Paul Raven Press: NY, Chapter 9, pp. 292-295.

Brown, et al. (1997) "Identification and Characterization of a Neutralizing Monoclonal Antibody against Botulinum Neurotoxin Serotype F, Following Vaccination with Active Toxin" Hybridoma 16(5):447-456.

Cenci Di Bello, et al. (1994) "Antagonism of the Intracellular Action of Botulinum Neurotoxin Type A with Monoclonal Antibodies That Map to Light-Chain Epitopes" Eur. J. Biochem. 219(1-2):161-169.

Ferreira, et al. (1987) "Monoclonal Antibody for the Detection of Clostridium botulinum Type A toxin" Mol. Cell Probes 1(4):337-345.

Hildebrand & Archer (1961) "Evidence Concerning Liquid Structure" PNAS USA 47(12):1881-1882.

Marchev & Marcheva (1982) "[Production of MonoSpecific Type A Botulinum Toxin and Antiserum Using a Column Chromatographic Method]" Vet. Med. Nauki. 19(1):57-63.

Noah, et al. (1995) "Production of Monoclonal Antibodies Specific to Clostridium botulinum Type B Neurotoxin" J. AOAC Int. 78(2):381-385.

\* cited by examiner

$K_d = 1.1 \times 10^{-8}$ M

3D12

$K_d = 5.5 \times 10^{-10}$ M

C25+3D12

$K_d = 6.5 \times 10^{-11}$ M

C25+3D12+S25

$K_d = 1.8 \times 10^{-11}$ M

SEQUENCE LISTING

```
<160> NUMBER OF SEQ ID NOS: 278

<210> SEQ ID NO 1
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 1
ctggacaggg atccagagtt cca                                             23

<210> SEQ ID NO 2
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 2
ctggacaggg ctccatagtt cca                                             23

<210> SEQ ID NO 3
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 3
ctcattcctg ttgaagctct tgac                                            24

<210> SEQ ID NO 4
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 4
gaggtgcagc ttcaggagtc agg                                             23

<210> SEQ ID NO 5
<211> LENGTH: 23
<212> TYPE: DNA
<213> ORGANISM: Artificial Sequence
<220> FEATURE:
<223> OTHER INFORMATION: oligonucleotide primer
```

```
<400> SEQUENCE: 5
gatgtgcagc ttcaggagtc rgg                                              23

<210> SEQ ID NO 6
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 6
caggtgcagc tgaagsagtc agg                                              23

<210> SEQ ID NO 7
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 7
gaggtycagc tgcarcartc tgg                                              23

<210> SEQ ID NO 8
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 8
caggtycarc tgcagcagyc tgg                                              23

<210> SEQ ID NO 9
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 9
gargtgaagc tggtggartc tgg                                              23

<210> SEQ ID NO 10
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 10
gaggttcagc ttcagcagtc tgg                                              23

<210> SEQ ID NO 11
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 11
gaagtgcagc tgktggagwc tgg                                              23

<210> SEQ ID NO 12
<211> LENGTH: 23
<212> TYPE: DNA
```

```
-continued

<213> ORGANISM: Artificial Sequence
<220> FEATURE:
<223> OTHER INFORMATION: oligonucleotide primer

<400> SEQUENCE: 12
cagatccagt tgctgcagtc tgg                                              23

<210> SEQ ID NO 13
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 13
gacattgtga tgwcacagtc tcc                                              23

<210> SEQ ID NO 14
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 14
gatgttktga tgacccaaac tcc                                              23

<210> SEQ ID NO 15
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 15
gatattgtga tracbcaggc wgc                                              23

<210> SEQ ID NO 16
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 16
gacattgtgc tgacmcartc tcc                                              23

<210> SEQ ID NO 17
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 17
saaawtgtkc tcacccagtc tcc                                              23

<210> SEQ ID NO 18
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 18
gayatyvwga tgacmcagwc tcc                                              23
```

```
<210> SEQ ID NO 19
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 19
caaattgttc tcacccagtc tcc                                              23

<210> SEQ ID NO 20
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 20
tcattattgc aggtgcttgt ggg                                              23

<210> SEQ ID NO 21
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 21
tgaggagacg gtgaccgtgg tccc                                             24

<210> SEQ ID NO 22
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 22
tgaggagact gtgagagtgg tgcc                                             24

<210> SEQ ID NO 23
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 23
tgcagagaca gtgaccagag tccc                                             24

<210> SEQ ID NO 24
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 24
tgaggagacg gtgactgagg ttcc                                             24

<210> SEQ ID NO 25
<211> LENGTH: 24
<212> TYPE: DNA
<213> ORGANISM: Artificial Sequence
<220> FEATURE:
<223> OTHER INFORMATION: oligonucleotide primer
```

```
<400> SEQUENCE: 25
tttgatttcc agcttggtgc ctcc                                    24

<210> SEQ ID NO 26
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 26
ttttatttcc agcttggtcc cccc                                    24

<210> SEQ ID NO 27
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 27
ttttatttcc agtctggtcc catc                                    24

<210> SEQ ID NO 28
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 28
ttttatttcc aactttgtcc ccga                                    24

<210> SEQ ID NO 29
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 29
tttcagctcc agcttggtcc cagc                                    24

<210> SEQ ID NO 30
<211> LENGTH: 56
<212> TYPE: DNA
<213> ORGANISM: Artificial Sequence
<220> FEATURE:
<223> OTHER INFORMATION: oligonucleotide primer

<400> SEQUENCE: 30
gtcctcgcaa ctgcggccca gccggccatg gccgaggtgc agcttcagga gtcagg      56

<210> SEQ ID NO 31
<211> LENGTH: 56
<212> TYPE: DNA
<213> ORGANISM: Artificial Sequence
<220> FEATURE:
<223> OTHER INFORMATION: oligonucleotide primer

<400> SEQUENCE: 31
gtcctcgcaa ctgcggccca gccggccatg gccgatgtgc agcttcagga gtcrgg      56

<210> SEQ ID NO 32
<211> LENGTH: 56
<212> TYPE: DNA
```

<213> ORGANISM: Artificial Sequence
<220> FEATURE:
<223> OTHER INFORMATION: oligonucleotide primer

<400> SEQUENCE: 32
gtcctcgcaa ctgcggccca gccggccatg gcccaggtgc agctgaagsa gtcagg        56

<210> SEQ ID NO 33
<211> LENGTH: 56
<212> TYPE: DNA
<213> ORGANISM: Artificial Sequence
<220> FEATURE:
<223> OTHER INFORMATION: oligonucleotide primer

<400> SEQUENCE: 33
gtcctcgcaa ctgcggccca gccggccatg gccgaggtyc agctgcarca rtctgg        56

<210> SEQ ID NO 34
<211> LENGTH: 56
<212> TYPE: DNA
<213> ORGANISM: Artificial Sequence
<220> FEATURE:
<223> OTHER INFORMATION: oligonucleotide primer

<400> SEQUENCE: 34
gtcctcgcaa ctgcggccca gccggccatg gcccaggtyc arctgcagca gyctgg        56

<210> SEQ ID NO 35
<211> LENGTH: 56
<212> TYPE: DNA
<213> ORGANISM: Artificial Sequence
<220> FEATURE:
<223> OTHER INFORMATION: oligonucleotide primer

<400> SEQUENCE: 35
gtcctcgcaa ctgcggccca gccggccatg gccgargtga agctggtgga rtctgg        56

<210> SEQ ID NO 36
<211> LENGTH: 56
<212> TYPE: DNA
<213> ORGANISM: Artificial Sequence
<220> FEATURE:
<223> OTHER INFORMATION: oligonucleotide primer

<400> SEQUENCE: 36
gtcctcgcaa ctgcggccca gccggccatg gccgaggttc agcttcagca gtctgg        56

<210> SEQ ID NO 37
<211> LENGTH: 56
<212> TYPE: DNA
<213> ORGANISM: Artificial Sequence
<220> FEATURE:
<223> OTHER INFORMATION: oligonucleotide primer

<400> SEQUENCE: 37
gtcctcgcaa ctgcggccca gccggccatg gccgaagtgc agctgktgga gwctgg        56

<210> SEQ ID NO 38
<211> LENGTH: 56
<212> TYPE: DNA
<213> ORGANISM: Artificial Sequence
<220> FEATURE:
<223> OTHER INFORMATION: oligonucleotide primer

<400> SEQUENCE: 38
gtcctcgcaa ctgcggccca gccggccatg gcccagatcc agttgctgca gtctgg        56

<210> SEQ ID NO 39
<211> LENGTH: 48
<212> TYPE: DNA
<213> ORGANISM: Artificial Sequence
<220> FEATURE:
<223> OTHER INFORMATION: oligonucleotide primer

<400> SEQUENCE: 39
gagtcattct cgacttgcgg ccgctttgat ttccagcttg gtgcctcc            48

<210> SEQ ID NO 40
<211> LENGTH: 48
<212> TYPE: DNA
<213> ORGANISM: Artificial Sequence
<220> FEATURE:
<223> OTHER INFORMATION: oligonucleotide primer

<400> SEQUENCE: 40
gagtcattct cgacttgcgg ccgcttttat ttccagcttg gtcccccc            48

<210> SEQ ID NO 41
<211> LENGTH: 48
<212> TYPE: DNA
<213> ORGANISM: Artificial Sequence
<220> FEATURE:
<223> OTHER INFORMATION: oligonucleotide primer

<400> SEQUENCE: 41
gagtcattct cgacttgcgg ccgcttttat ttccagtctg gtcccatc            48

<210> SEQ ID NO 42
<211> LENGTH: 48
<212> TYPE: DNA
<213> ORGANISM: Artificial Sequence
<220> FEATURE:
<223> OTHER INFORMATION: oligonucleotide primer

<400> SEQUENCE: 42
gagtcattct cgacttgcgg ccgcttttat ttccaacttt gtccccga            48

<210> SEQ ID NO 43
<211> LENGTH: 48
<212> TYPE: DNA
<213> ORGANISM: Artificial Sequence
<220> FEATURE:
<223> OTHER INFORMATION: oligonucleotide primer

<400> SEQUENCE: 43
gagtcattct cgacttgcgg ccgctttcag ctccagcttg gtcccagc            48

<210> SEQ ID NO 44
<211> LENGTH: 36
<212> TYPE: DNA
<213> ORGANISM: Artificial Sequence
<220> FEATURE:
<223> OTHER INFORMATION: oligonucleotide primer

<400> SEQUENCE: 44
gtctcctgag ctagctgagg agacggtgac cgtggt            36

<210> SEQ ID NO 45
<211> LENGTH: 42
<212> TYPE: DNA
<213> ORGANISM: Artificial Sequence
<220> FEATURE:
<223> OTHER INFORMATION: oligonucleotide primer

```
<400> SEQUENCE: 45
gtaccaacgc gtgtcttgtc ccaggtccag ctgcaggagt ct                        42

<210> SEQ ID NO 46
<211> LENGTH: 42
<212> TYPE: DNA
<213> ORGANISM: Artificial Sequence
<220> FEATURE:
<223> OTHER INFORMATION: oligonucleotide primer

<400> SEQUENCE: 46
gtaccaacgc gtgtcttgtc ccaggtgaag ctgcagcagt ca                        42

<210> SEQ ID NO 47
<211> LENGTH: 42
<212> TYPE: DNA
<213> ORGANISM: Artificial Sequence
<220> FEATURE:
<223> OTHER INFORMATION: oligonucleotide primer

<400> SEQUENCE: 47
gtaccaacgc gtgtcttgtc ccaggtgcag ctggtgcagt ct                        42

<210> SEQ ID NO 48
<211> LENGTH: 54
<212> TYPE: DNA
<213> ORGANISM: Artificial Sequence
<220> FEATURE:
<223> OTHER INFORMATION: oligonucleotide primer

<400> SEQUENCE: 48
tcagtcgttg catgtactcc aggtgcacga tgtgacatcg agctcactca gtct           54

<210> SEQ ID NO 49
<211> LENGTH: 36
<212> TYPE: DNA
<213> ORGANISM: Artificial Sequence
<220> FEATURE:
<223> OTHER INFORMATION: oligonucleotide primer

<400> SEQUENCE: 49
ctggaaatca aacgtacgtt ttatttccag cttggt                               36

<210> SEQ ID NO 50
<211> LENGTH: 54
<212> TYPE: DNA
<213> ORGANISM: Artificial Sequence
<220> FEATURE:
<223> OTHER INFORMATION: oligonucleotide primer

<400> SEQUENCE: 50
tcagtcgttg catgtactcc aggtgcacga tgtgacatcg agctcactca gtct           54

<210> SEQ ID NO 51
<211> LENGTH: 36
<212> TYPE: DNA
<213> ORGANISM: Artificial Sequence
<220> FEATURE:
<223> OTHER INFORMATION: oligonucleotide primer

<400> SEQUENCE: 51
ctggaaatca aacgtacgtt tgatttccag cttggt                               36

<210> SEQ ID NO 52
<211> LENGTH: 54
<212> TYPE: DNA
```

<213> ORGANISM: Artificial Sequence
<220> FEATURE:
<223> OTHER INFORMATION: oligonucleotide primer

<400> SEQUENCE: 52
tcagtcgttg catgtactcc aggtgcacga tgtgacatcg tgatgaccca gtct    54

<210> SEQ ID NO 53
<211> LENGTH: 36
<212> TYPE: DNA
<213> ORGANISM: Artificial Sequence
<220> FEATURE:
<223> OTHER INFORMATION: oligonucleotide primer

<400> SEQUENCE: 53
ctggaaatca aacgtacgtt ttatctccag cttggt    36

<210> SEQ ID NO 54
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 54

Gly Arg Gly Val Asn
1               5

<210> SEQ ID NO 55
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 55

Asn Gly Asp Pro Glu Ala Phe Asp Tyr
1               5

<210> SEQ ID NO 56
<211> LENGTH: 10
<212> TYPE: PRT
<213> ORGANISM: Artificial Sequence
<220> FEATURE:
<223> OTHER INFORMATION: single chain antibody fragment

<400> SEQUENCE: 56

Ala Leu Gln Ser Asp Ser Pro Tyr Phe Asp
1               5                   10

<210> SEQ ID NO 57
<211> LENGTH: 10
<212> TYPE: PRT
<213> ORGANISM: Artificial Sequence
<220> FEATURE:
<223> OTHER INFORMATION: single chain antibody fragment

<400> SEQUENCE: 57

Asp Leu Ala Ile Phe Ala Gly Asn Asp Tyr
1               5                   10

<210> SEQ ID NO 58
<211> LENGTH: 11
<212> TYPE: PRT
<213> ORGANISM: Artificial Sequence
<220> FEATURE:
<223> OTHER INFORMATION: single chain antibody fragment

```
<400> SEQUENCE: 58

Val Gly Val Asp Arg Trp Tyr Pro Ala Asp Tyr
1               5                   10

<210> SEQ ID NO 59
<211> LENGTH: 12
<212> TYPE: PRT
<213> ORGANISM: Artificial Sequence
<220> FEATURE:
<223> OTHER INFORMATION: single chain antibody fragment

<400> SEQUENCE: 59

Asp Leu Leu Asp Gly Ser Gly Ala Tyr Phe Asp Tyr
1               5                   10

<210> SEQ ID NO 60
<211> LENGTH: 13
<212> TYPE: PRT
<213> ORGANISM: Artificial Sequence
<220> FEATURE:
<223> OTHER INFORMATION: single chain antibody fragment

<400> SEQUENCE: 60

Asp Leu Asp Tyr Gly Gly Asn Ala Gly Tyr Phe Asp Leu
1               5                   10

<210> SEQ ID NO 61
<211> LENGTH: 13
<212> TYPE: PRT
<213> ORGANISM: Artificial Sequence
<220> FEATURE:
<223> OTHER INFORMATION: single chain antibody fragment

<400> SEQUENCE: 61

Asp Leu Asp Tyr Gly Gly Asn Ala Gly Tyr Phe Asp Leu
1               5                   10

<210> SEQ ID NO 62
<211> LENGTH: 13
<212> TYPE: PRT
<213> ORGANISM: Artificial Sequence
<220> FEATURE:
<223> OTHER INFORMATION: single chain antibody fragment

<400> SEQUENCE: 62

Asp Tyr Thr Ala Asn Tyr Tyr Tyr Tyr Gly Met Asp Val
1               5                   10

<210> SEQ ID NO 63
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 63

Asp Leu Gly Tyr Gly Ser Gly Thr Ser Ser Tyr Tyr Leu Asp Tyr
1               5                   10                  15

<210> SEQ ID NO 64
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 64
```

```
Gln Gln Ala Asn Ser Phe Pro Arg Thr
 1               5

<210> SEQ ID NO 65
<211> LENGTH: 8
<212> TYPE: PRT
<213> ORGANISM: Artificial Sequence
<220> FEATURE:
<223> OTHER INFORMATION: single chain antibody fragment

<400> SEQUENCE: 65

Leu Gln Asp Tyr Asn Gly Trp Thr
 1               5

<210> SEQ ID NO 66
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 66

Asn Ser Arg Asp Ser Ser Gly Asn His Val Val
 1               5                  10

<210> SEQ ID NO 67
<211> LENGTH: 12
<212> TYPE: PRT
<213> ORGANISM: Artificial Sequence
<220> FEATURE:
<223> OTHER INFORMATION: single chain antibody fragment

<400> SEQUENCE: 67

Lys Ser Arg Asp Ser Arg Gly Asn His Leu Ala Leu
 1               5                  10

<210> SEQ ID NO 68
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 68

Gln Gln Tyr His Thr Ile Ser Arg Thr
 1               5

<210> SEQ ID NO 69
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 69

Asn Ser Arg Asp Ser Ser Gly Asn His Val Val
 1               5                  10

<210> SEQ ID NO 70
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 70

His Ser Arg Asp Ser Ser Val Thr Asn Leu Asp
 1               5                  10
```

```
<210> SEQ ID NO 71
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 71

Asn Ser Arg Asp Ser Ser Gly Asn His Gln Val
1               5                   10

<210> SEQ ID NO 72
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 72

Asn Ser Arg Asp Ser Ser Gly Val Val
1               5

<210> SEQ ID NO 73
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 73

Asn Ser Arg Asp Ser Ser Gly Asn His Val Val
1               5                   10

<210> SEQ ID NO 74
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 74

Leu Ala Thr Tyr Tyr Tyr Phe Gly Leu Asp Val
1               5                   10

<210> SEQ ID NO 75
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 75

Leu Ala Thr Tyr Tyr Tyr Phe Gly Leu Asp Val
1               5                   10

<210> SEQ ID NO 76
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 76

Gly Pro Trp Glu Leu Val Gly Tyr Phe Asp Ser
1               5                   10
```

```
<210> SEQ ID NO 77
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 77

Glu Pro Asp Trp Leu Leu Trp Gly Asp Arg Gly Ala Leu Asp Val
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 78

Glu Pro Asp Trp Leu Leu Trp Gly Asp Arg Gly Ala Leu Asp Val
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 79

Glu Pro Asp Trp Leu Leu Trp Gly Asp Arg Gly Ala Leu Asp Val
1               5                   10                  15

<210> SEQ ID NO 80
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 80

Gln Gln Tyr Asn Ser Tyr Val Tyr Thr
1               5

<210> SEQ ID NO 81
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 81

Gln Gln Leu Asn Ser Tyr Pro Leu Thr
1               5

<210> SEQ ID NO 82
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 82

Gln Gln Leu Ile Ser Tyr Pro Leu Thr
1               5

<210> SEQ ID NO 83
<211> LENGTH: 9
```

```
<212> TYPE: PRT
<213> ORGANISM: Artificial Sequence
<220> FEATURE:
<223> OTHER INFORMATION: single chain antibody fragment

<400> SEQUENCE: 83

Gln His Tyr Asn Thr Tyr Pro Tyr Thr
1               5

<210> SEQ ID NO 84
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 84

Gln His Tyr Asn Thr Tyr Pro Tyr Thr
1               5

<210> SEQ ID NO 85
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 85

Gln His Tyr Asn Thr Tyr Pro Tyr Thr
1               5

<210> SEQ ID NO 86
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 86

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 87
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 87

Asp Tyr Tyr Met Tyr
1               5

<210> SEQ ID NO 88
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 88

Trp Val Arg Gln Ala Pro Gly Lys Gly Leu Glu Trp Val Ala
1               5                   10

<210> SEQ ID NO 89
```

<211> LENGTH: 17
<212> TYPE: PRT
<213> ORGANISM: Artificial Sequence
<220> FEATURE:
<223> OTHER INFORMATION: single chain antibody fragment

<400> SEQUENCE: 89

Thr Ile Ser Asp Gly Gly Ser Tyr Thr Tyr Tyr Pro Asp Ser Val Lys
1               5                   10                  15
Gly

<210> SEQ ID NO 90
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 90

Gln Val Gln Leu Gln Glu Ser Gly Gly Gly Leu Val Gln Pro Gly Gly
1               5                   10                  15
Ser Leu Arg Leu Ser Cys Ala Ala Ser Gly Phe Thr Phe Ser
            20                  25                  30

<210> SEQ ID NO 91
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 91

Asp Tyr Tyr Met Tyr
1               5

<210> SEQ ID NO 92
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 92

Trp Val Arg Gln Ala Pro Gly Lys Gly Leu Glu Trp Val Ala
1               5                   10

<210> SEQ ID NO 93
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 93

Thr Ile Ser Asp Gly Gly Ser Tyr Thr Tyr Tyr Pro Asp Ser Val Lys
1               5                   10                  15
Gly

<210> SEQ ID NO 94
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 94

```
Gln Val Gln Leu Gln Glu Ser Gly Gly Gly Leu Val Gln Pro Gly Gly
  1               5                  10                  15

Ser Leu Arg Leu Ser Cys Ala Ala Ser Gly Phe Thr Phe Ser
              20                  25                  30

<210> SEQ ID NO 95
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 95

Asp His Tyr Met Tyr
  1               5

<210> SEQ ID NO 96
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 96

Trp Val Arg Gln Ala Pro Gly Lys Gly Leu Glu Trp Val Ala
  1               5                  10

<210> SEQ ID NO 97
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 97

Thr Ile Ser Asp Gly Gly Ser Tyr Thr Tyr Tyr Pro Asp Ser Val Lys
  1               5                  10                  15

Gly

<210> SEQ ID NO 98
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 98

Gln Val Gln Leu Gln Glu Ser Gly Gly Gly Leu Val Gln Pro Gly Gly
  1               5                  10                  15

Ser Leu Arg Leu Ser Cys Ala Ala Ser Gly Phe Thr Ser Ser
              20                  25                  30

<210> SEQ ID NO 99
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 99

Asp His Tyr Met Tyr
  1               5

<210> SEQ ID NO 100
<211> LENGTH: 14
<212> TYPE: PRT
```

-continued

<213> ORGANISM: Artificial Sequence
<220> FEATURE:
<223> OTHER INFORMATION: single chain antibody fragment

<400> SEQUENCE: 100

Trp Val Arg Gln Ala Pro Gly Lys Gly Leu Glu Trp Val Ala
1               5                   10

<210> SEQ ID NO 101
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 101

Thr Ile Ser Asp Gly Gly Ser Tyr Thr Tyr Tyr Pro Asp Ser Val Lys
1               5                   10                  15
Gly

<210> SEQ ID NO 102
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 102

Gln Val Gln Leu Gln Glu Ser Gly Gly Gly Leu Val Gln Pro Gly Gly
1               5                   10                  15
Ser Leu Arg Leu Ser Cys Ala Ala Ser Gly Phe Thr Ser Ser
            20                  25                  30

<210> SEQ ID NO 103
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 103

Asp His Tyr Met Tyr
1               5

<210> SEQ ID NO 104
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 104

Trp Val Arg Gln Ala Pro Gly Lys Gly Leu Glu Trp Val Ala
1               5                   10

<210> SEQ ID NO 105
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 105

Thr Ile Ser Asp Gly Gly Ser Tyr Thr Tyr Tyr Pro Asp Ser Val Lys
1               5                   10                  15
Gly

```
<210> SEQ ID NO 106
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 106

Gln Val Gln Leu Val Gln Ser Gly Gly Gly Val Val His Pro Gly Arg
 1               5                  10                  15

Ser Leu Lys Leu Ser Cys Ala Gly Ser Gly Phe Thr Phe Ser
            20                  25                  30

<210> SEQ ID NO 107
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 107

Asp Tyr Asp Met His
 1               5

<210> SEQ ID NO 108
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 108

Trp Val Arg Gln Ala Pro Gly Lys Gly Leu Glu Trp Val Ala
 1               5                  10

<210> SEQ ID NO 109
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 109

Val Met Trp Phe Asp Gly Thr Glu Lys Tyr Ser Ala Glu Ser Val Lys
 1               5                  10                  15

Gly

<210> SEQ ID NO 110
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 110

Gln Val Gln Leu Val Gln Ser Gly Gly Gly Val Val His Pro Gly Arg
 1               5                  10                  15

Ser Leu Lys Leu Ser Cys Ala Gly Ser Gly Phe Thr Phe Ser
            20                  25                  30

<210> SEQ ID NO 111
<211> LENGTH: 5
<212> TYPE: PRT
<213> ORGANISM: Artificial Sequence
<220> FEATURE:
```

-continued

<223> OTHER INFORMATION: single chain antibody fragment

<400> SEQUENCE: 111

Asp Tyr Asp Met His
1               5

<210> SEQ ID NO 112
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 112

Trp Val Arg Gln Ala Pro Gly Lys Gly Leu Glu Trp Val Ala
1               5                   10

<210> SEQ ID NO 113
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 113

Val Met Trp Phe Asp Gly Thr Glu Lys Tyr Ser Ala Glu Ser Val Lys
1               5                   10                  15

Gly

<210> SEQ ID NO 114
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 114

Gln Val Gln Leu Val Gln Ser Gly Gly Gly Val Val His Pro Gly Arg
1               5                   10                  15

Ser Leu Lys Leu Ser Cys Ala Gly Ser Gly Phe Thr Phe Ser
            20                  25                  30

<210> SEQ ID NO 115
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 115

Asp Tyr Asp Met His
1               5

<210> SEQ ID NO 116
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 116

Trp Val Arg Gln Ala Pro Gly Lys Gly Leu Glu Trp Val Ala
1               5                   10

<210> SEQ ID NO 117
<211> LENGTH: 17

<212> TYPE: PRT
<213> ORGANISM: Artificial Sequence
<220> FEATURE:
<223> OTHER INFORMATION: single chain antibody fragment

<400> SEQUENCE: 117

Val Ile Trp Phe Asp Gly Thr Glu Lys Tyr Ser Ala Glu Ser Val Lys
 1               5                  10                  15
Gly

<210> SEQ ID NO 118
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 118

Gln Val Gln Leu Val Gln Ser Gly Gly Gly Val Val His Pro Gly Arg
 1               5                  10                  15
Ser Leu Lys Leu Ser Cys Ala Gly Ser Gly Phe Thr Phe Ser
            20                  25                  30

<210> SEQ ID NO 119
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 119

Asp Tyr Asp Met His
 1               5

<210> SEQ ID NO 120
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 120

Trp Val Arg Gln Ala Pro Gly Lys Gly Phe Glu Trp Val Ala
 1               5                  10

<210> SEQ ID NO 121
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 121

Val Met Trp Phe Asp Gly Thr Glu Lys Tyr Ser Ala Glu Ser Val Lys
 1               5                  10                  15
Gly

<210> SEQ ID NO 122
<211> LENGTH: 30
<212> TYPE: PRT
<213> ORGANISM: Artificial Sequence
<220> FEATURE:
<223> OTHER INFORMATION: single chain antibody fragment

<400> SEQUENCE: 122

Gln Val Gln Leu Gln Gln Ser Gly Gly Gly Leu Val Gln Pro Gly Gly

```
                1               5                  10                  15
Ser Leu Arg Leu Ser Cys Ala Ala Ser Gly Phe Thr Phe Ser
                20                  25                  30

<210> SEQ ID NO 123
<211> LENGTH: 5
<212> TYPE: PRT
<213> ORGANISM: Artificial Sequence
<220> FEATURE:
<223> OTHER INFORMATION: single chain antibody fragment

<400> SEQUENCE: 123

Asn Tyr Ala Met Thr
 1               5

<210> SEQ ID NO 124
<211> LENGTH: 14
<212> TYPE: PRT
<213> ORGANISM: Artificial Sequence
<220> FEATURE:
<223> OTHER INFORMATION: single chain antibody fragment

<400> SEQUENCE: 124

Trp Val Arg Gln Ala Pro Gly Lys Gly Leu Glu Trp Val Ser
 1               5                  10

<210> SEQ ID NO 125
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 125

Ser Ile Ser Val Gly Gly Ser Asp Thr Tyr Tyr Ala Asp Ser Val Lys
 1               5                  10                  15
Gly

<210> SEQ ID NO 126
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 126

Arg Phe Thr Ile Ser Arg Asp Asn Ser Lys Asn Thr Leu Tyr Leu Gln
 1               5                  10                  15
Met Asn Ser Leu Arg Ala Glu Asp Thr Ala Met Tyr Tyr Cys Ser Arg
                20                  25                  30

<210> SEQ ID NO 127
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 127

Tyr Arg Tyr Asp Asp Ala Met Asp Tyr
 1               5

<210> SEQ ID NO 128
<211> LENGTH: 11
<212> TYPE: PRT
<213> ORGANISM: Artificial Sequence
```

```
<220> FEATURE:
<223> OTHER INFORMATION: single chain antibody fragment

<400> SEQUENCE: 128

Trp Gly Gln Gly Thr Leu Val Thr Val Ser Ser
1               5                   10

<210> SEQ ID NO 129
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 129

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Ile Tyr Tyr Cys Ser Arg
            20                  25                  30

<210> SEQ ID NO 130
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 130

Tyr Arg Tyr Asp Asp Ala Met Asp Tyr
1               5

<210> SEQ ID NO 131
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 131

Trp Gly Gln Gly Thr Leu Val Thr Val Ser Ser
1               5                   10

<210> SEQ ID NO 132
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 132

Arg Phe Thr Thr Ser Arg Asp Asn Ser Lys Asn Thr Leu Tyr Leu Gln
1               5                   10                  15

Met Asn Ser Leu Arg Ala Glu Asp Thr Ala Ile Tyr Tyr Cys Ser Arg
            20                  25                  30

<210> SEQ ID NO 133
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 133

Tyr Arg Tyr Asp Asp Ala Met Asp Tyr
1               5
```

```
<210> SEQ ID NO 134
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 134

Trp Gly Gln Gly Thr Leu Val Thr Val Ser Ser
 1               5                  10

<210> SEQ ID NO 135
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 135

Arg Phe Thr Val Ser Arg Asp Asn Ser Lys Asn Thr Leu Tyr Leu Gln
 1               5                  10                  15

Met Asn Ser Leu Arg Ala Glu Asp Thr Ala Ile Tyr Tyr Cys Ser Arg
             20                  25                  30

<210> SEQ ID NO 136
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 136

Tyr Arg Tyr Asp Asp Ala Met Asp Tyr
 1               5

<210> SEQ ID NO 137
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 137

Trp Gly Gln Gly Thr Leu Val Thr Val Ser Ser
 1               5                  10

<210> SEQ ID NO 138
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 138

Arg Phe Thr Thr Ser Arg Asp Asn Ser Lys Asn Thr Leu Tyr Leu Gln
 1               5                  10                  15

Met Asn Ser Leu Arg Ala Glu Asp Thr Ala Ile Tyr Tyr Cys Ser Arg
             20                  25                  30

<210> SEQ ID NO 139
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 139
```

Tyr Arg Tyr Asp Asp Ala Met Asp Tyr
1               5

<210> SEQ ID NO 140
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 140

Trp Gly Gln Gly Thr Leu Val Thr Val Ser Ser
1               5                   10

<210> SEQ ID NO 141
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 141

Arg Phe Thr Ile Ser Arg Asp Asn Ser Lys Asn Thr Leu Phe Leu Gln
1               5                   10                  15

Met Asn Ser Leu Arg Ala Asp Asp Thr Ala Val Tyr Tyr Cys Ala Arg
            20                  25                  30

<210> SEQ ID NO 142
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 142

Glu Pro Asp Trp Leu Leu Trp Gly Asp Arg Gly Ala Leu Asp Val
1               5                   10                  15

<210> SEQ ID NO 143
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 143

Trp Gly Gln Gly Thr Thr Val Thr Val Ser Ser
1               5                   10

<210> SEQ ID NO 144
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 144

Arg Phe Thr Ile Ser Arg Asp Asn Ser Lys Asn Thr Leu Phe Leu Gln
1               5                   10                  15

Met Asn Ser Leu Arg Ala Asp Asp Thr Ala Val Tyr Tyr Cys Ala Arg
            20                  25                  30

<210> SEQ ID NO 145
<211> LENGTH: 15
<212> TYPE: PRT
<213> ORGANISM: Artificial Sequence
<220> FEATURE:

<223> OTHER INFORMATION: single chain antibody fragment

<400> SEQUENCE: 145

Glu Pro Asp Trp Leu Leu Trp Gly Asp Arg Gly Ala Leu Asp Val
1               5                   10                  15

<210> SEQ ID NO 146
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 146

Trp Gly Gln Gly Thr Thr Val Thr Val Ser Ser
1               5                   10

<210> SEQ ID NO 147
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 147

Arg Phe Thr Ile Ser Arg Asp Asn Ser Lys Asn Thr Leu Phe Leu Gln
1               5                   10                  15

Met Asn Ser Leu Arg Ala Asp Asp Thr Ala Val Tyr Tyr Cys Ala Arg
            20                  25                  30

<210> SEQ ID NO 148
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 148

Glu Pro Asp Trp Leu Leu Trp Gly Asp Arg Gly Ala Leu Asp Val
1               5                   10                  15

<210> SEQ ID NO 149
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 149

Trp Gly Gln Gly Thr Thr Val Thr Val Ser Ser
1               5                   10

<210> SEQ ID NO 150
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 150

Arg Phe Thr Ile Ser Arg Asp Asn Ser Lys Asn Thr Leu Phe Leu Gln
1               5                   10                  15

Met Asn Ser Leu Arg Ala Asp Asp Thr Ala Val Tyr Tyr Cys Ala Arg
            20                  25                  30

<210> SEQ ID NO 151

```
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 151

Glu Pro Asp Arg Leu Leu Trp Gly Asp Arg Gly Ala Leu Asp Val
1               5                   10                  15

<210> SEQ ID NO 152
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 152

Trp Gly Gln Gly Thr Thr Val Thr Val Ser Ser
1               5                   10

<210> SEQ ID NO 153
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 153

Arg Phe Thr Val Ser Arg Asp Asn Ser Lys Asn Thr Leu Leu Leu Gln
1               5                   10                  15

Met Asn Ser Leu Arg Ala Glu Asp Thr Ala Val Tyr Tyr Cys Ala Lys
            20                  25                  30

<210> SEQ ID NO 154
<211> LENGTH: 17
<212> TYPE: PRT
<213> ORGANISM: Artificial Sequence
<220> FEATURE:
<223> OTHER INFORMATION: single chain antibody fragment

<400> SEQUENCE: 154

Val Arg Thr Lys Tyr Cys Ser Ser Leu Ser Cys Phe Ala Gly Phe Asp
1               5                   10                  15

Ser

<210> SEQ ID NO 155
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 155

Trp Gly Gln Gly Thr Leu Val Thr Val Ser Ser
1               5                   10

<210> SEQ ID NO 156
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 156

Glu Ile Val Leu Thr Gln Ser Pro Ala Thr Leu Ser Leu Ser Pro Gly
1               5                   10                  15
```

Glu Arg Ala Thr Ile Ser Cys
            20

<210> SEQ ID NO 157
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 157

Arg Ala Ser Glu Ser Val Asp Ser Tyr Gly His Ser Phe Met Gln
1               5                   10                  15

<210> SEQ ID NO 158
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 158

Trp Tyr Gln Gln Lys Pro Gly Gln Ala Pro Arg Leu Leu Ile Tyr
1               5                   10                  15

<210> SEQ ID NO 159
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 159

Arg Ala Ser Asn Leu Glu Pro
1               5

<210> SEQ ID NO 160
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 160

Glu Ile Val Leu Thr Gln Ser Pro Ala Thr Leu Ser Leu Ser Pro Gly
1               5                   10                  15
Glu Arg Ala Thr Ile Ser Cys
            20

<210> SEQ ID NO 161
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 161

Arg Ala Ser Glu Ser Val Asp Ser Tyr Gly His Ser Phe Met Gln
1               5                   10                  15

<210> SEQ ID NO 162
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 162

Trp Tyr Gln Gln Lys Pro Gly Gln Ala Pro Arg Leu Leu Ile Tyr
1               5                   10                  15

<210> SEQ ID NO 163
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 163

Arg Ala Ser Asn Leu Glu Pro
1               5

<210> SEQ ID NO 164
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 164

Glu Ile Val Leu Thr Gln Ser Pro Ala Thr Leu Ser Leu Ser Pro Gly
1               5                   10                  15

Glu Arg Ala Thr Ile Ser Cys
            20

<210> SEQ ID NO 165
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 165

Arg Ala Ser Glu Ser Val Asp Ser Tyr Gly His Ser Phe Met Gln
1               5                   10                  15

<210> SEQ ID NO 166
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 166

Trp Tyr Gln Gln Lys Pro Gly Gln Ala Pro Arg Leu Leu Ile Tyr
1               5                   10                  15

<210> SEQ ID NO 167
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 167

Arg Ala Ser Asn Leu Glu Pro
1               5

<210> SEQ ID NO 168
<211> LENGTH: 23
<212> TYPE: PRT
<213> ORGANISM: Artificial Sequence
<220> FEATURE:
<223> OTHER INFORMATION: single chain antibody fragment

```
<400> SEQUENCE: 168

Glu Ile Val Leu Thr Gln Ser Pro Ala Thr Leu Ser Leu Ser Pro Gly
 1               5                  10                  15

Glu Arg Ala Thr Ile Ser Cys
            20

<210> SEQ ID NO 169
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 169

Arg Ala Ser Glu Ser Val Asp Ser Tyr Gly His Ser Phe Met Gln
 1               5                  10                  15

<210> SEQ ID NO 170
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 170

Trp Tyr Gln Gln Lys Pro Gly Gln Ala Pro Arg Leu Leu Ile Tyr
 1               5                  10                  15

<210> SEQ ID NO 171
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 171

Arg Ala Ser Asn Leu Glu Pro
 1               5

<210> SEQ ID NO 172
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 172

Glu Ile Val Leu Thr Gln Ser Pro Ala Thr Leu Ser Leu Ser Pro Gly
 1               5                  10                  15

Glu Arg Ala Thr Ile Ser Cys
            20

<210> SEQ ID NO 173
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 173

Arg Ala Ser Glu Ser Val Asp Ser Tyr Gly His Ser Phe Met Gln
 1               5                  10                  15

<210> SEQ ID NO 174
<211> LENGTH: 15
```

```
<212> TYPE: PRT
<213> ORGANISM: Artificial Sequence
<220> FEATURE:
<223> OTHER INFORMATION: single chain antibody fragment

<400> SEQUENCE: 174

Trp Tyr Gln Gln Lys Pro Gly Gln Ala Pro Arg Leu Leu Ile Tyr
 1               5                  10                  15

<210> SEQ ID NO 175
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 175

Arg Ala Ser Asn Leu Glu Pro
 1               5

<210> SEQ ID NO 176
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 176

Asp Ile Val Met Thr Gln Ser Pro Ser Thr Leu Ser Ala Ser Val Gly
 1               5                  10                  15

Asp Arg Val Thr Ile Thr Cys
                20

<210> SEQ ID NO 177
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 177

Arg Ala Ser Gln Ser Ile Ser Ser Trp Leu Ala
 1               5                  10

<210> SEQ ID NO 178
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 178

Trp Tyr Gln Gln Lys Pro Gly Lys Ala Pro Lys Leu Leu Met Tyr
 1               5                  10                  15

<210> SEQ ID NO 179
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 179

Glu Ala Ser Ser Leu Glu Ser
 1               5

<210> SEQ ID NO 180
```

```
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 180

Asp Ile Val Met Thr Gln Ser Pro Ser Thr Leu Ser Ala Ser Val Gly
 1               5                  10                  15

Asp Arg Val Thr Ile Thr Cys
            20

<210> SEQ ID NO 181
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 181

Trp Ala Ser Gln Ser Ile Ser Ser Arg Leu Ala
 1               5                  10

<210> SEQ ID NO 182
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 182

Trp Tyr Gln Gln Lys Pro Gly Lys Ala Pro Lys Leu Leu Met Tyr
 1               5                  10                  15

<210> SEQ ID NO 183
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 183

Glu Ala Thr Ser Leu Gly Ser
 1               5

<210> SEQ ID NO 184
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 184

Asp Ile Val Met Thr Gln Ser Pro Ser Thr Leu Ser Ala Ser Val Gly
 1               5                  10                  15

Asp Arg Val Thr Ile Thr Cys
            20

<210> SEQ ID NO 185
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 185

Arg Ala Ser Gln Ser Ile Ser Ser Trp Leu Ala
```

```
<210> SEQ ID NO 186
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 186

Trp Tyr Gln Gln Lys Pro Gly Lys Ala Pro Lys Leu Leu Met Tyr
 1               5                  10                  15

<210> SEQ ID NO 187
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 187

Gly Ala Ser Ser Leu Gly Ser
 1               5

<210> SEQ ID NO 188
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 188

Asp Ile Val Met Thr Gln Ser Pro Ser Thr Leu Ser Ala Ser Val Gly
 1               5                  10                  15

Asp Arg Val Thr Ile Thr Cys
            20

<210> SEQ ID NO 189
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 189

Arg Ala Ser Gln Ser Ile Ser Ser Trp Leu Ala
 1               5                  10

<210> SEQ ID NO 190
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 190

Trp Tyr Gln Gln Lys Pro Gly Lys Ala Pro Lys Leu Leu Met Tyr
 1               5                  10                  15

<210> SEQ ID NO 191
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 191
```

Glu Ala Ser Ser Leu Gly Arg
1               5

<210> SEQ ID NO 192
<211> LENGTH: 23
<212> TYPE: PRT
<213> ORGANISM: Artificial Sequence
<220> FEATURE:
<223> OTHER INFORMATION: single chain antibody fragment

<400> SEQUENCE: 192

Asp Ile Val Met Thr Gln Ser Pro Ser Ser Leu Ser Ala Ser Val Gly
1               5                   10                  15

Asp Arg Val Thr Ile Thr Cys
            20

<210> SEQ ID NO 193
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 193

Arg Ala Ser Gln Ser Ile Ser Ser Tyr Leu Asn
1               5                   10

<210> SEQ ID NO 194
<211> LENGTH: 15
<212> TYPE: PRT
<213> ORGANISM: Artificial Sequence
<220> FEATURE:
<223> OTHER INFORMATION: single chain antibody fragment

<400> SEQUENCE: 194

Trp Tyr Gln Gln Lys Pro Gly Lys Ala Pro Lys Leu Leu Ile Tyr
1               5                   10                  15

<210> SEQ ID NO 195
<211> LENGTH: 7
<212> TYPE: PRT
<213> ORGANISM: Artificial Sequence
<220> FEATURE:
<223> OTHER INFORMATION: single chain antibody fragment

<400> SEQUENCE: 195

Ala Ala Ser Ser Leu Gln Ser
1               5

<210> SEQ ID NO 196
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 196

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 197
<211> LENGTH: 9
<212> TYPE: PRT
<213> ORGANISM: Artificial Sequence
<220> FEATURE:

<223> OTHER INFORMATION: single chain antibody fragment

<400> SEQUENCE: 197

Gln Gln Ser Asn Glu Asp Pro Phe Thr
1               5

<210> SEQ ID NO 198
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 198

Phe Gly Gln Gly Thr Lys Val Glu Ile Lys Arg
1               5                   10

<210> SEQ ID NO 199
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 199

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 200
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 200

Gln Gln Gly Asn Glu Val Pro Phe Thr
1               5

<210> SEQ ID NO 201
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 201

Phe Gly Gln Gly Thr Lys Val Glu Ile Lys Arg
1               5                   10

<210> SEQ ID NO 202
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 202

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 203

```
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 203

Gln Gln Gly Asn Glu Val Pro Phe Thr
 1               5

<210> SEQ ID NO 204
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 204

Phe Gly Gln Gly Thr Lys Val Glu Ile Lys Arg
 1               5                  10

<210> SEQ ID NO 205
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 205

Gly Ile Pro Ala Arg Phe Ser Gly Ser Gly Ser Gly Thr Asp Phe Thr
 1               5                  10                  15

Leu Thr Ile Ser Ser Leu Glu Pro Glu Asp Phe Ala Val Tyr Tyr Cys
             20                  25                  30

<210> SEQ ID NO 206
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 206

Gln Gln Gly Asn Glu Val Pro Phe Thr
 1               5

<210> SEQ ID NO 207
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 207

Phe Gly Gln Gly Thr Lys Val Glu Ile Lys Arg
 1               5                  10

<210> SEQ ID NO 208
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 208

Gly Ile Pro Ala Arg Phe Ser Gly Ser Gly Ser Gly Thr Asp Phe Thr
 1               5                  10                  15

Leu Thr Ile Ser Ser Leu Glu Pro Glu Asp Phe Ala Val Tyr Tyr Cys
```

20              25              30

<210> SEQ ID NO 209
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 209

Gln Gln Gly Asn Glu Val Pro Phe Thr
1               5

<210> SEQ ID NO 210
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 210

Phe Gly Gln Gly Thr Lys Val Glu Ile Lys Arg
1               5                   10

<210> SEQ ID NO 211
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 211

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Ala Tyr Tyr Cys
            20                  25                  30

<210> SEQ ID NO 212
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 212

Gln His Tyr Asn Thr Tyr Pro Tyr Thr
1               5

<210> SEQ ID NO 213
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 213

Phe Gly Gln Gly Thr Lys Leu Glu Ile Lys Arg
1               5                   10

<210> SEQ ID NO 214
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 214

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Ala Tyr Tyr Cys
            20                  25                  30

<210> SEQ ID NO 215
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 215

Gln His Tyr Asp Thr Tyr Pro Tyr Thr
1               5

<210> SEQ ID NO 216
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 216

Phe Gly Gln Gly Thr Lys Leu Glu Ile Lys Arg
1               5                   10

<210> SEQ ID NO 217
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 217

Gly Val Pro Ser Arg Phe Ser Gly Ser Gly Ser Gly Thr Glu Phe Thr
1               5                   10                  15

Leu Thr Ile Ser Ser Leu His Pro Asp Asp Phe Ala Ala Tyr Tyr Cys
            20                  25                  30

<210> SEQ ID NO 218
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 218

Gln His Tyr Asn Thr Tyr Pro Tyr Thr
1               5

<210> SEQ ID NO 219
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 219

Phe Gly Gln Gly Thr Lys Leu Glu Ile Lys Arg
1               5                   10

<210> SEQ ID NO 220
<211> LENGTH: 32
<212> TYPE: PRT
<213> ORGANISM: Artificial Sequence
<220> FEATURE:

<223> OTHER INFORMATION: single chain antibody fragment

<400> SEQUENCE: 220

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Ala Tyr Tyr Cys
            20                  25                  30

<210> SEQ ID NO 221
<211> LENGTH: 9
<212> TYPE: PRT
<213> ORGANISM: Artificial Sequence
<220> FEATURE:
<223> OTHER INFORMATION: single chain antibody fragment

<400> SEQUENCE: 221

Gln His Tyr Ser Thr Tyr Pro Tyr Thr
1               5

<210> SEQ ID NO 222
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 222

Phe Gly Gln Gly Thr Lys Leu Glu Ile Lys Arg
1               5                   10

<210> SEQ ID NO 223
<211> LENGTH: 32
<212> TYPE: PRT
<213> ORGANISM: Artificial Sequence
<220> FEATURE:
<223> OTHER INFORMATION: single chain antibody fragment

<400> SEQUENCE: 223

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 224
<211> LENGTH: 10
<212> TYPE: PRT
<213> ORGANISM: Artificial Sequence
<220> FEATURE:
<223> OTHER INFORMATION: single chain antibody fragment

<400> SEQUENCE: 224

Gln Gln Ser Tyr Ser Thr Pro Arg Thr Thr
1               5                   10

<210> SEQ ID NO 225
<211> LENGTH: 11
<212> TYPE: PRT
<213> ORGANISM: Artificial Sequence
<220> FEATURE:
<223> OTHER INFORMATION: single chain antibody fragment

<400> SEQUENCE: 225

Phe Gly Gly Gly Thr Lys Val Asp Ile Lys Arg
1               5                   10

<210> SEQ ID NO 226

```
<211> LENGTH: 15
<212> TYPE: PRT
<213> ORGANISM: Artificial Sequence
<220> FEATURE:
<223> OTHER INFORMATION: protein linker

<400> SEQUENCE: 226

Gly Gly Gly Gly Ser Gly Gly Gly Gly Ser Gly Gly Gly Gly Ser
1               5                   10                  15

<210> SEQ ID NO 227
<211> LENGTH: 5
<212> TYPE: PRT
<213> ORGANISM: Artificial Sequence
<220> FEATURE:
<223> OTHER INFORMATION: protein linker

<400> SEQUENCE: 227

Ser Ser Ser Ser Gly
1               5

<210> SEQ ID NO 228
<211> LENGTH: 15
<212> TYPE: PRT
<213> ORGANISM: Artificial Sequence
<220> FEATURE:
<223> OTHER INFORMATION: protein linker

<400> SEQUENCE: 228

Ser Ser Ser Ser Gly Ser Ser Ser Gly Ser Ser Ser Ser Gly
1               5                   10                  15

<210> SEQ ID NO 229
<211> LENGTH: 55
<212> TYPE: DNA
<213> ORGANISM: Artificial Sequence
<220> FEATURE:
<223> OTHER INFORMATION: oligonucleotide primer

<400> SEQUENCE: 229
accaccgaat tcttattaat ggtgatgatg gtggatgacc agccggttcc agcgg          55

<210> SEQ ID NO 230
<211> LENGTH: 125
<212> TYPE: PRT
<213> ORGANISM: Artificial Sequence
<220> FEATURE:
<223> OTHER INFORMATION: single chain antibody

<400> SEQUENCE: 230

Gln Val Lys Leu Gln Gln Ser Gly Ala Glu Leu Val Arg Pro Gly Ala
1               5                   10                  15

Ser Val Lys Leu Ser Cys Lys Thr Ser Gly Tyr Ser Phe Thr Ser Tyr
                20                  25                  30

Trp Met Asn Trp Val Lys Gln Gly Pro Gly Gln Gly Leu Glu Trp Ile
            35                  40                  45

Gly Met Ile His Pro Ser Asn Ser Glu Ile Arg Phe Asn Gln Lys Phe
        50                  55                  60

Glu Asp Met Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Arg Gly Ile Tyr Tyr Asp Tyr Asp Gly Gly Asn Tyr Tyr Ala Met
            100                 105                 110
```

Asp Tyr Trp Gly Gln Gly Thr Thr Val Thr Ala Ser Ser
            115                 120                 125

<210> SEQ ID NO 231
<211> LENGTH: 125
<212> TYPE: PRT
<213> ORGANISM: Artificial Sequence
<220> FEATURE:
<223> OTHER INFORMATION: single chain antibody

<400> SEQUENCE: 231

Gln Val Lys Leu Gln Gln Ser Gly Ala Glu Leu Val Arg Pro Gly Ala
1               5                   10                  15

Ser Val Lys Leu Ser Cys Lys Thr Ser Gly Tyr Ser Phe Thr Ser Tyr
                20                  25                  30

Trp Met Asn Trp Val Lys Gln Gly Pro Gly Gln Gly Leu Glu Trp Ile
            35                  40                  45

Gly Met Ile His Pro Ser Asn Ser Glu Ile Arg Phe Asn Gln Lys Phe
    50                  55                  60

Glu Asn Met Ala Thr Leu Thr Val Asp Lys Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Arg Gly Ile Tyr Tyr Val Tyr Asp Gly Asn Tyr Tyr Ala Met
            100                 105                 110

Asp Tyr Trp Gly Gln Gly Thr Thr Val Thr Val Ser Ser
            115                 120                 125

<210> SEQ ID NO 232
<211> LENGTH: 125
<212> TYPE: PRT
<213> ORGANISM: Artificial Sequence
<220> FEATURE:
<223> OTHER INFORMATION: single chain antibody

<400> SEQUENCE: 232

Glu Val Lys Leu Val Glu Ser Gly Ala Glu Leu Val Arg Pro Gly Ala
1               5                   10                  15

Ser Val Asn Leu Ser Cys Lys Ala Ser Gly Tyr Ser Phe Thr Ser Tyr
                20                  25                  30

Trp Met Asn Trp Val Lys Gln Arg Pro Gly Gln Gly Leu Glu Trp Ile
            35                  40                  45

Gly Met Ile His Pro Ser Asn Ser Glu Thr Arg Leu Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Arg Gly Ile Tyr Tyr Asp Tyr Asp Glu Gly Tyr Tyr Tyr Thr Leu
            100                 105                 110

Asp Tyr Trp Gly Gln Gly Thr Thr Leu Thr Val Ser Ser
            115                 120                 125

<210> SEQ ID NO 233
<211> LENGTH: 121
<212> TYPE: PRT
<213> ORGANISM: Artificial Sequence
<220> FEATURE:
<223> OTHER INFORMATION: single chain antibody

<400> SEQUENCE: 233

Gln Val Lys Leu Gln Gln Ser Gly Ala Glu Leu Val Arg Pro Gly Ala
1               5                   10                  15

Ser Val Lys Leu Ser Cys Lys Ala Ser Gly Tyr Ser Phe Thr Ser Tyr
            20                  25                  30

Trp Met Asn Trp Val Lys Gln Arg Pro Gly Gln Gly Leu Glu Trp Ile
        35                  40                  45

Gly Met Ile His Pro Ser Asn Ser Asp Thr Arg Phe Asn Gln Lys Phe
    50                  55                  60

Glu Asp Lys Ala Thr Leu Thr Val Asp Arg Ser Ser Thr Ala Ile
65                  70                  75                  80

His Gln Leu Ser Ser Pro Thr Ser Glu Asp Ser Ala Val Tyr Tyr Cys
                85                  90                  95

Ala Arg Gly Leu Tyr Gly Tyr Gly Phe Trp Tyr Phe Asp Val Trp Gly
                100                 105                 110

Gln Gly Thr Thr Val Thr Val Ser Ser
            115                 120

<210> SEQ ID NO 234
<211> LENGTH: 120
<212> TYPE: PRT
<213> ORGANISM: Artificial Sequence
<220> FEATURE:
<223> OTHER INFORMATION: single chain antibody

<400> SEQUENCE: 234

Gln Val Lys Leu Gln Gln Ser Gly Ala Glu Leu Val Arg Pro Gly Ala
1               5                   10                  15

Ser Val Lys Leu Ser Cys Lys Ala Ser Gly Tyr Ser Leu Thr Ser Tyr
            20                  25                  30

Trp Met Asn Trp Val Lys Gln Arg Pro Gly Gln Gly Leu Glu Trp Ile
        35                  40                  45

Gly Met Ile His Pro Ser Asp Ser Asp Thr Arg Phe Asn Gln Lys Phe
    50                  55                  60

Glu Asp Lys Ala Thr Leu Thr Val Asp Thr Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Arg Gly Leu Tyr Asn Gly Phe Trp Tyr Phe Asp Val Trp Gly Gln
                100                 105                 110

Gly Thr Thr Val Thr Val Ser Ser
            115                 120

<210> SEQ ID NO 235
<211> LENGTH: 117
<212> TYPE: PRT
<213> ORGANISM: Artificial Sequence
<220> FEATURE:
<223> OTHER INFORMATION: single chain antibody

<400> SEQUENCE: 235

Gln Val Gln Leu Gln Gln Ser Gly Ala Glu Leu Val Arg Pro Gly Val
1               5                   10                  15

Ser Val Lys Ile Ser Cys Lys Ala Ser Gly Tyr Thr Phe Ile Asp Tyr
            20                  25                  30

Ala Met His Trp Val Lys Gln Ser Pro Ala Lys Ser Leu Glu Trp Ile
        35                  40                  45

Gly Val Ile Ser Ser Tyr Tyr Gly Asp Thr Asp Tyr Asn Gln Ile Phe
    50                  55                  60

```
Lys Gly Lys Ala Thr Leu Thr Val Asp Lys Ser Ser Asn Thr Ala Tyr
 65                  70                  75                  80

Met Glu Leu Ala Arg Leu Thr Ser Asp Asp Ser Ala Ile Tyr Tyr Cys
                 85                  90                  95

Ala Arg Arg Gly Lys Gly Ala Met Asp Tyr Trp Gly Gln Gly Thr Thr
            100                 105                 110

Val Thr Val Ser Ser
            115

<210> SEQ ID NO 236
<211> LENGTH: 117
<212> TYPE: PRT
<213> ORGANISM: Artificial Sequence
<220> FEATURE:
<223> OTHER INFORMATION: single chain antibody

<400> SEQUENCE: 236

Gln Val Gln Leu Lys Gln Ser Gly Ala Glu Leu Val Arg Pro Gly Val
 1               5                  10                  15

Ser Val Lys Ile Ser Cys Lys Gly Ser Gly Tyr Thr Phe Ile Asp Tyr
                20                  25                  30

Ala Val His Trp Val Lys Gln Ser His Ala Lys Ser Leu Glu Trp Ile
            35                  40                  45

Gly Val Ile Ser Thr Tyr Tyr Gly Asp Ala Asp Tyr Asn Pro Lys Phe
        50                  55                  60

Lys Gly Lys Ala Thr Leu Thr Val Asn Lys Ser Ser Asn Thr Ala Tyr
 65                  70                  75                  80

Met Glu Leu Pro Arg Leu Thr Ser Glu Asp Ser Ala Ile Tyr Tyr Cys
                 85                  90                  95

Ala Arg Arg Gly Lys Gly Ala Met Asp Tyr Trp Gly Gln Gly Thr Ser
            100                 105                 110

Val Thr Val Ser Ser
            115

<210> SEQ ID NO 237
<211> LENGTH: 115
<212> TYPE: PRT
<213> ORGANISM: Artificial Sequence
<220> FEATURE:
<223> OTHER INFORMATION: single chain antibody

<400> SEQUENCE: 237

Glu Val Gln Leu Gln Glu Ser Gly Pro Gly Leu Val Lys Pro Ser Gln
 1               5                  10                  15

Ser Leu Ser Leu Thr Cys Thr Val Thr Gly Tyr Ser Ile Thr Asp Tyr
                20                  25                  30

Ala Trp Asn Trp Ile Arg Gln Phe Pro Gly Lys Lys Leu Glu Trp Met
            35                  40                  45

Gly Tyr Ile Ser Tyr Ser Gly Ser Thr Gly Tyr Asn Pro Ser Leu Lys
        50                  55                  60

Ser Arg Ile Ser Ile Thr Arg Asp Thr Ser Lys Asn Gln Phe Phe Leu
 65                  70                  75                  80

Gln Leu Asn Ser Val Thr Thr Glu Asp Thr Gly Thr Tyr Tyr Cys Ala
                 85                  90                  95

Arg Gly Tyr Asp Ala Met Asp Tyr Trp Gly Gln Gly Thr Ser Val Thr
            100                 105                 110

Val Ser Ser
            115
```

-continued

<210> SEQ ID NO 238
<211> LENGTH: 115
<212> TYPE: PRT
<213> ORGANISM: Artificial Sequence
<220> FEATURE:
<223> OTHER INFORMATION: single chain antibody

<400> SEQUENCE: 238

Glu Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Asp Tyr
            20                  25                  30

Ala Trp Tyr Trp Ile Arg Gln Phe Pro Gly Lys Lys Leu Glu Trp Met
        35                  40                  45

Gly Tyr Ile Ser Tyr Ser Gly Ser Thr Gly Tyr Asn Pro Ser Leu Lys
    50                  55                  60

Ser Arg Ile Ser Ile Thr Arg Asp Thr Ser Lys Asn Gln Phe Phe Leu
65                  70                  75                  80

Gln Leu Asn Ser Val Thr Thr Glu Asp Thr Gly Thr Tyr Tyr Cys Ala
                85                  90                  95

Arg Gly Tyr Asp Ala Met Asp Tyr Trp Gly Gln Gly Thr Ser Val Thr
            100                 105                 110

Val Ser Ser
        115

<210> SEQ ID NO 239
<211> LENGTH: 123
<212> TYPE: PRT
<213> ORGANISM: Artificial Sequence
<220> FEATURE:
<223> OTHER INFORMATION: single chain antibody

<400> SEQUENCE: 239

Glu Val Lys Leu Val Glu Ser Gly Gly Gly Leu Val Gln Pro Gly Gly
1               5                   10                  15

Ser Arg Lys Leu Ser Cys Ala Thr Ser Gly Phe Thr Phe Ser Asp Tyr
            20                  25                  30

Tyr Met Ser Trp Ile Arg Gln Ser Pro Asp Lys Arg Leu Glu Trp Val
        35                  40                  45

Ala Thr Ile Ser Asp Gly Gly Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Val Arg His Gly Tyr Gly Asn Tyr Pro Ser His Trp Tyr Phe Asp Val
            100                 105                 110

Trp Gly Ala Gly Thr Thr Val Thr Val Ser Ser
        115                 120

<210> SEQ ID NO 240
<211> LENGTH: 123
<212> TYPE: PRT
<213> ORGANISM: Artificial Sequence
<220> FEATURE:
<223> OTHER INFORMATION: single chain antibody

<400> SEQUENCE: 240

Glu Val Lys Leu Val Glu Ser Gly Gly Gly Leu Val Gln Pro Gly Gly

```
            1               5                  10                 15
Ser Leu Lys Leu Ser Cys Ala Ala Ser Gly Phe Thr Phe Ser Asn Tyr
            20                 25                 30

Gly Met Ser Trp Val Arg Gln Thr Pro Asp Lys Arg Leu Glu Trp Val
            35                 40                 45

Ala Met Ile Ser Ser Gly Gly Ser Tyr Asn Tyr Tyr Ser Asp Ser Val
            50                 55                 60

Lys Gly Arg Val Thr Ile Ser Arg Asp Asn Ala Lys Ser Thr Leu Tyr
 65                70                 75                 80

Leu Gln Met Ser Ser Leu Gln Ser Glu Asp Thr Ala Met Tyr Leu Cys
                85                 90                 95

Thr Arg His Gly Tyr Gly Asn Tyr Pro Ser Tyr Trp Tyr Phe Asp Val
            100                105                110

Trp Gly Ala Gly Thr Thr Val Thr Val Ser Ser
            115                120

<210> SEQ ID NO 241
<211> LENGTH: 118
<212> TYPE: PRT
<213> ORGANISM: Artificial Sequence
<220> FEATURE:
<223> OTHER INFORMATION: single chain antibody

<400> SEQUENCE: 241

Gln Val Gln Leu Gln Glu Ser Gly Gly Gly Val Lys Pro Gly Gly
 1               5                  10                 15

Ser Leu Lys Leu Ser Cys Ala Ala Ser Gly Phe Thr Phe Ser Asp Tyr
            20                 25                 30

Tyr Met Ser Trp Val Arg Gln Thr Pro Glu Lys Arg Leu Glu Trp Val
            35                 40                 45

Ala Thr Ile Ser Asp Gly Gly Ser Tyr Thr Tyr Tyr Pro Asp Ser Val
            50                 55                 60

Lys Gly Arg Phe Thr Ile Ser Arg Asp Asn Ala Lys Asn Asn Leu Tyr
 65                70                 75                 80

Leu Gln Met Ser Ser Leu Lys Ser Glu Asp Thr Ala Ile Tyr Tyr Cys
                85                 90                 95

Val Arg Tyr Arg Tyr Asp Glu Gly Leu Asp Tyr Trp Gly Gln Gly Thr
            100                105                110

Thr Val Thr Val Ser Ser
            115

<210> SEQ ID NO 242
<211> LENGTH: 118
<212> TYPE: PRT
<213> ORGANISM: Artificial Sequence
<220> FEATURE:
<223> OTHER INFORMATION: single chain antibody

<400> SEQUENCE: 242

Gln Val Gln Leu Gln Glu Ser Gly Gly Gly Leu Val Lys Pro Gly Gly
 1               5                  10                 15

Ser Leu Lys Leu Ser Cys Ala Ala Ser Gly Phe Thr Phe Ser Asp Tyr
            20                 25                 30

Tyr Met Tyr Trp Val Arg Gln Thr Pro Glu Lys Arg Leu Glu Trp Val
            35                 40                 45

Ala Thr Ile Ser Asp Gly Gly Ser Tyr Thr Tyr Tyr Pro Asp Ser Val
            50                 55                 60

Lys Gly Arg Phe Thr Ile Ser Arg Asp Asn Ala Lys Asn Asn Leu Tyr
```

```
                 65                  70                  75                  80
Leu Gln Met Ser Ser Leu Lys Ser Glu Asp Thr Ala Met Tyr Tyr Cys
                85                  90                  95

Ser Arg Tyr Arg Tyr Asp Asp Ala Met Asp Tyr Trp Gly Gln Gly Thr
            100                 105                 110

Thr Val Thr Val Ser Ser
        115

<210> SEQ ID NO 243
<211> LENGTH: 118
<212> TYPE: PRT
<213> ORGANISM: Artificial Sequence
<220> FEATURE:
<223> OTHER INFORMATION: single chain antibody

<400> SEQUENCE: 243

Glu Val Lys Leu Val Glu Ser Gly Gly Gly Leu Val Lys Pro Gly Gly
  1               5                  10                  15

Ser Leu Lys Leu Ser Cys Ala Ala Ser Gly Phe Thr Phe Ser Ser Tyr
                20                  25                  30

Ala Met Ser Trp Val Arg Gln Thr Pro Glu Lys Arg Leu Glu Trp Val
            35                  40                  45

Ala Thr Ile Ser Asp Gly Gly Thr Tyr Thr Tyr Tyr Thr Asp Asn Val
        50                  55                  60

Lys Gly Arg Phe Thr Ile Ser Arg Asp Asn Ala Lys His Asn Leu Tyr
 65                  70                  75                  80

Leu Gln Met Ser His Leu Lys Ser Glu Asp Thr Ala Met Tyr Tyr Cys
                85                  90                  95

Ala Arg Asn Leu Pro Tyr Asp His Val Asp Tyr Trp Gly Gln Gly Thr
            100                 105                 110

Ser Val Thr Val Ser Ser
        115

<210> SEQ ID NO 244
<211> LENGTH: 118
<212> TYPE: PRT
<213> ORGANISM: Artificial Sequence
<220> FEATURE:
<223> OTHER INFORMATION: single chain antibody

<400> SEQUENCE: 244

Glu Val Lys Leu Lys Glu Ser Gly Gly Gly Leu Val Lys Pro Gly Gly
  1               5                  10                  15

Ser Leu Lys Leu Ser Cys Ala Ala Ser Gly Phe Thr Phe Ser Ser Tyr
                20                  25                  30

Ala Met Ser Trp Val Arg Gln Thr Pro Glu Lys Arg Leu Glu Trp Val
            35                  40                  45

Ala Thr Ile Ser Asp Gly Gly Thr Tyr Thr Tyr Tyr Thr Asp Asn Val
        50                  55                  60

Lys Gly Arg Phe Thr Ile Ser Arg Asp Asn Ala Lys His Asn Leu Tyr
 65                  70                  75                  80

Leu Gln Met Ser His Leu Lys Ser Glu Asp Thr Ala Met Tyr Tyr Cys
                85                  90                  95

Ala Arg Asn Leu Pro Tyr Asp His Val Asp Tyr Trp Gly Gln Gly Thr
            100                 105                 110

Ser Val Thr Val Ser Ser
        115
```

```
<210> SEQ ID NO 245
<211> LENGTH: 118
<212> TYPE: PRT
<213> ORGANISM: Artificial Sequence
<220> FEATURE:
<223> OTHER INFORMATION: single chain antibody

<400> SEQUENCE: 245

Glu Gly Lys Leu Val Glu Ser Gly Gly Gly Leu Val Lys Pro Gly Gly
 1               5                  10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu His Arg Leu Glu Trp Val
        35                  40                  45

Ala Thr Ile Ser Asp Gly Gly Thr Phe Thr Tyr Tyr Thr Asp Asn Val
    50                  55                  60

Lys Gly Arg Phe Thr Ile Ser Arg Asp Asn Ala Lys His Asn Leu Tyr
65                  70                  75                  80

Leu Gln Met Ser His Leu Lys Ser Glu Asp Thr Ala Met Tyr Tyr Cys
                85                  90                  95

Ala Arg Asn Leu Pro Tyr Asp His Val Asp Tyr Trp Gly Gln Gly Thr
            100                 105                 110

Ser Val Thr Val Ser Ser
        115

<210> SEQ ID NO 246
<211> LENGTH: 118
<212> TYPE: PRT
<213> ORGANISM: Artificial Sequence
<220> FEATURE:
<223> OTHER INFORMATION: single chain antibody

<400> SEQUENCE: 246

Glu Val Lys Leu Val Glu Ser Gly Gly Gly Leu Val Lys Pro Gly Gly
 1               5                  10                  15

Pro Leu Lys Leu Ser Cys Ala Ala Ser Gly Phe Thr Phe Ser Ser Tyr
            20                  25                  30

Ala Met Ser Trp Val Arg Gln Thr Pro Glu His Arg Leu Glu Trp Val
        35                  40                  45

Ala Thr Ile Ser Asp Gly Gly Thr Phe Thr Tyr Tyr Thr Asp Asn Val
    50                  55                  60

Lys Gly Arg Phe Thr Ile Ser Arg Asp Asn Ala Lys His Asn Leu Tyr
65                  70                  75                  80

Leu Gln Met Ser His Leu Lys Ser Glu Asp Thr Ala Met Tyr Tyr Cys
                85                  90                  95

Ala Arg Asn Leu Pro Tyr Asp His Val Asp Tyr Trp Gly Gln Gly Thr
            100                 105                 110

Ser Val Thr Val Ser Ser
        115

<210> SEQ ID NO 247
<211> LENGTH: 122
<212> TYPE: PRT
<213> ORGANISM: Artificial Sequence
<220> FEATURE:
<223> OTHER INFORMATION: single chain antibody

<400> SEQUENCE: 247

Glu Val Gln Leu Gln Glu Ser Gly Gly Gly Val Val Gln Pro Gly Arg
 1               5                  10                  15
```

-continued

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Trp Ser Glu Gly Tyr Tyr Tyr Gly Met Asp Val Trp
            100                 105                 110

Gly Gln Gly Thr Thr Val Ile Val Ser Ser
            115                 120

<210> SEQ ID NO 248
<211> LENGTH: 122
<212> TYPE: PRT
<213> ORGANISM: Artificial Sequence
<220> FEATURE:
<223> OTHER INFORMATION: single chain antibody

<400> SEQUENCE: 248

Gln Ile Gln Leu Leu Gln Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Trp Ser Glu Gly Tyr Tyr Tyr Gly Met Asp Val Trp
            100                 105                 110

Gly Gln Gly Thr Thr Val Ile Val Ser Ser
            115                 120

<210> SEQ ID NO 249
<211> LENGTH: 121
<212> TYPE: PRT
<213> ORGANISM: Artificial Sequence
<220> FEATURE:
<223> OTHER INFORMATION: single chain antibody

<400> SEQUENCE: 249

Val Lys Leu Val Glu Ser Gly Pro Gly Leu Val Lys Pro Ser Gln Ser
1               5                   10                  15

Leu Ser Leu Thr Cys Thr Val Thr Gly Tyr Ser Ile Thr Ser Asp Tyr
            20                  25                  30

Ala Trp Asn Trp Ile Arg Gln Phe Pro Gly Asn Lys Leu Glu Trp Met
            35                  40                  45

Gly Tyr Ile Asn Tyr Asp Gly Ser Asn Asn Tyr Asn Pro Ser Leu Lys
    50                  55                  60

Asn Arg Ile Ser Ile Thr Arg Asp Thr Ser Lys Asn Gln Phe Phe Leu
65                  70                  75                  80

Lys Leu Asn Ser Val Thr Ser Glu Asp Thr Ala Thr Tyr Tyr Cys Ala
                85                  90                  95

Arg Ala Gly Asp Gly Tyr Tyr Val Asp Trp Tyr Phe Asp Val Trp Gly
            100                 105                 110

Thr Gly Thr Thr Val Ile Val Ser Ser
        115                 120

<210> SEQ ID NO 250
<211> LENGTH: 117
<212> TYPE: PRT
<213> ORGANISM: Artificial Sequence
<220> FEATURE:
<223> OTHER INFORMATION: single chain antibody

<400> SEQUENCE: 250

Gln Val Gln Leu Gln Gln Ser Gly Ala Glu Leu Val Gln Pro Gly Ala
1               5                   10                  15

Ser Val Lys Met Ser Cys Lys Ala Ser Gly Tyr Thr Phe Thr Ser Tyr
            20                  25                  30

Trp Thr Thr Trp Val Lys Gln Arg Pro Gly Gln Gly Leu Glu Trp Ile
        35                  40                  45

Gly Asp Ile Tyr Pro Gly Ser Gly Ser Thr Asn Tyr Asn Glu Lys Phe
    50                  55                  60

Lys Ser Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Leu Gly Asp Ala Met Asp Tyr Trp Gly Gln Gly Thr Ser
            100                 105                 110

Val Ile Val Ser Ser
        115

<210> SEQ ID NO 251
<211> LENGTH: 117
<212> TYPE: PRT
<213> ORGANISM: Artificial Sequence
<220> FEATURE:
<223> OTHER INFORMATION: single chain antibody

<400> SEQUENCE: 251

Glu Val Gln Leu Gln Gln Ser Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Trp Thr Thr Trp Val Lys Gln Arg Pro Gly Gln Gly Leu Glu Trp Ile
        35                  40                  45

Gly Asp Ile Tyr Pro Asp Ser Gly Ser Thr Asn Tyr Asn Glu Lys Phe
    50                  55                  60

Lys Ser Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Leu Gly Asp Ala Met Asp Tyr Trp Gly Gln Gly Thr Ser
            100                 105                 110

Val Ile Val Ser Ser
        115

<210> SEQ ID NO 252
<211> LENGTH: 119

<212> TYPE: PRT
<213> ORGANISM: Artificial Sequence
<220> FEATURE:
<223> OTHER INFORMATION: single chain antibody

<400> SEQUENCE: 252

Glu Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Phe
            20                  25                  30

Trp Met His Trp Val Lys Gln Arg Pro Gly Arg Gly Leu Glu Trp Ile
        35                  40                  45

Gly Arg Leu Asp Pro Asn Ser Gly Glu Thr Lys Tyr Asn Glu Lys Phe
    50                  55                  60

Lys Ser Lys Ala Thr Leu Thr Val Asp Lys Pro Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Glu Ala Tyr Gly Tyr Trp Asn Phe Asp Val Trp Gly Thr Gly
            100                 105                 110

Thr Thr Val Thr Val Ser Ser
        115

<210> SEQ ID NO 253
<211> LENGTH: 119
<212> TYPE: PRT
<213> ORGANISM: Artificial Sequence
<220> FEATURE:
<223> OTHER INFORMATION: single chain antibody

<400> SEQUENCE: 253

Glu Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Phe
            20                  25                  30

Trp Met His Trp Val Lys Gln Arg Pro Gly Arg Gly Leu Glu Trp Ile
        35                  40                  45

Gly Arg Leu Asp Pro Asn Ser Gly Glu Thr Lys Tyr Asn Lys Lys Phe
    50                  55                  60

Lys Ser Lys Ala Thr Leu Thr Val Asp Lys Pro Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Glu Ala Tyr Gly Tyr Trp Asn Phe Asp Val Trp Gly Thr Gly
            100                 105                 110

Thr Thr Val Thr Val Ser Ser
        115

<210> SEQ ID NO 254
<211> LENGTH: 107
<212> TYPE: PRT
<213> ORGANISM: Artificial Sequence
<220> FEATURE:
<223> OTHER INFORMATION: single chain antibody

<400> SEQUENCE: 254

Asp Ile Glu Leu Thr Gln Ser Pro Ala Ile Met Ser Ala Ser Pro Gly
1               5                   10                  15

Glu Lys Val Ile Met Thr Cys Ser Ala Ser Ser Val Ser His Met
            20                  25                  30

Tyr Trp Tyr Gln Gln Lys Pro Gly Ser Ser Pro Arg Leu Leu Ile Tyr
                35                  40                  45

Asp Thr Ser Asn Leu Ala Ser Gly Val Pro Ile Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ser Ala Thr Tyr Tyr Cys Gln Gln Trp Ser Ser Tyr Pro Phe Thr
                85                  90                  95

Phe Gly Ser Gly Thr Lys Leu Glu Leu Lys Arg
            100                 105

<210> SEQ ID NO 255
<211> LENGTH: 107
<212> TYPE: PRT
<213> ORGANISM: Artificial Sequence
<220> FEATURE:
<223> OTHER INFORMATION: single chain antibody

<400> SEQUENCE: 255

Asp Ile Asp Leu Thr Gln Ser Pro Ala Ile Met Ser Ser Ser Pro Gly
1               5                   10                  15

Glu Lys Val Ile Ile Thr Cys Ser Ala Ser Ser Ser Val Ser Tyr Met
            20                  25                  30

His Trp Phe Gln Gln Lys Pro Gly Thr Ser Pro Lys Pro Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Val Glu Ala Glu
65                  70                  75                  80

Asp Ala Ala Thr Tyr Tyr Cys Gln Gln Tyr Ser Gly Tyr Pro Leu Thr
                85                  90                  95

Phe Gly Ala Gly Thr Lys Leu Glu Ile Lys Arg
            100                 105

<210> SEQ ID NO 256
<211> LENGTH: 109
<212> TYPE: PRT
<213> ORGANISM: Artificial Sequence
<220> FEATURE:
<223> OTHER INFORMATION: single chain antibody

<400> SEQUENCE: 256

Asp Ile Glu Leu Thr Gln Ser Pro Ala Ile Met Ala Ala Ser Pro Gly
1               5                   10                  15

Glu Lys Val Ile Ile Thr Cys Ser Ala Ser Ser Ser Ile Ser Ser Ser
            20                  25                  30

Asn Leu His Trp Tyr Gln Gln Lys Ser Glu Thr Ser Pro Lys Pro Trp
        35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Gly Ser Tyr Pro
                85                  90                  95

Leu Thr Phe Gly Gly Gly Thr Lys Leu Glu Ile Lys Arg
            100                 105

<210> SEQ ID NO 257

```
<211> LENGTH: 107
<212> TYPE: PRT
<213> ORGANISM: Artificial Sequence
<220> FEATURE:
<223> OTHER INFORMATION: single chain antibody

<400> SEQUENCE: 257

Asp Ile Glu Leu Thr Gln Ser Pro Ala Ile Met Ser Ala Ser Pro Gly
 1               5                  10                  15

Glu Lys Val Ile Met Thr Cys Ser Ala Ser Ser Val Ser Tyr Met
             20                  25                  30

Tyr Trp Tyr Gln Gln Lys Pro Gly Ser Ser Pro Arg Leu Leu Ile Tyr
             35                  40                  45

Asp Thr Ser Asn Leu Ala Ser Gly Val Pro Val Arg Phe Ser Gly Ser
         50                  55                  60

Gly Ser Gly Thr Ser Tyr Ser Leu Thr Ile Ser Arg Met Glu Ala Glu
 65                  70                  75                  80

Asp Ala Ala Thr Tyr Tyr Cys Gln Gln Trp Ser Ser Tyr Pro Leu Thr
                 85                  90                  95

Phe Gly Ala Gly Thr Lys Leu Glu Leu Lys Arg
            100                 105

<210> SEQ ID NO 258
<211> LENGTH: 109
<212> TYPE: PRT
<213> ORGANISM: Artificial Sequence
<220> FEATURE:
<223> OTHER INFORMATION: single chain antibody

<400> SEQUENCE: 258

Asp Ile Glu Leu Thr Gln Ser Pro Ala Leu Met Ala Ala Ser Pro Gly
 1               5                  10                  15

Glu Lys Val Ile Ile Thr Cys Ser Val Ser Ser Ile Ser Ser Ser
             20                  25                  30

Asn Leu His Trp Tyr Gln Gln Lys Ser Gly Thr Ser Pro Lys Pro Trp
             35                  40                  45

Ile Tyr Gly Thr Ser Asn Leu Ala Ser Gly Val Pro Val Arg Phe Ser
         50                  55                  60

Gly Ser Gly Ser Gly Thr Ser Tyr Ser Leu Thr Ile Ser Ser Met Glu
 65                  70                  75                  80

Ala Glu Asp Ala Ala Thr Tyr Tyr Cys Gln Gln Trp Ser Ser Tyr Pro
                 85                  90                  95

Leu Thr Phe Gly Ala Gly Thr Lys Leu Glu Ile Lys Arg
            100                 105

<210> SEQ ID NO 259
<211> LENGTH: 112
<212> TYPE: PRT
<213> ORGANISM: Artificial Sequence
<220> FEATURE:
<223> OTHER INFORMATION: single chain antibody

<400> SEQUENCE: 259

Asp Ile Glu Leu Thr Gln Ser Pro Ala Ser Leu Ala Val Ser Leu Gly
 1               5                  10                  15

Gln Arg Ala Ile Ile Ser Cys Arg Ala Ser Glu Ser Val Asp Ser Tyr
             20                  25                  30

Gly Asn Ser Phe Met His Trp Tyr Gln Gln Lys Pro Gly Gln Pro Pro
             35                  40                  45

Lys Leu Leu Ile Tyr Arg Ala Ser Asn Leu Glu Ser Gly Ile Pro Ala
```

```
                50                  55                  60
Arg Phe Ser Gly Ser Gly Ser Arg Thr Asp Phe Thr Leu Thr Ile Asn
 65                  70                  75                  80

Pro Val Glu Ala Asp Asp Val Ala Thr Tyr Tyr Cys Gln Gln Ser Asn
                    85                  90                  95

Glu Asp Pro Pro Thr Phe Gly Ala Gly Thr Lys Leu Glu Leu Lys Arg
                100                 105                 110

<210> SEQ ID NO 260
<211> LENGTH: 112
<212> TYPE: PRT
<213> ORGANISM: Artificial Sequence
<220> FEATURE:
<223> OTHER INFORMATION: single chain antibody

<400> SEQUENCE: 260

Asp Ile Glu Leu Thr Gln Ser Pro Ala Ser Leu Ala Val Ser Leu Gly
  1               5                  10                  15

Gln Arg Ala Ile Ile Ser Cys Arg Ala Ser Glu Ser Val Asp Ser Tyr
                 20                  25                  30

Gly Asn Ser Phe Met His Trp Tyr Gln Gln Lys Pro Gly Gln Pro Pro
             35                  40                  45

Lys Leu Leu Ile Tyr Arg Ala Ser Asn Leu Glu Gly Gln Ile Pro Ala
         50                  55                  60

Arg Phe Ser Gly Ser Gly Ser Arg Thr Asp Phe Thr Leu Thr Ile Asn
 65                  70                  75                  80

Pro Val Glu Ala Asp Asp Val Ala Thr Tyr Tyr Cys Gln Gln Ser Asn
                    85                  90                  95

Glu Asp Pro Tyr Thr Phe Gly Gly Gly Thr Lys Leu Glu Ile Lys Arg
                100                 105                 110

<210> SEQ ID NO 261
<211> LENGTH: 107
<212> TYPE: PRT
<213> ORGANISM: Artificial Sequence
<220> FEATURE:
<223> OTHER INFORMATION: single chain antibody

<400> SEQUENCE: 261

Asp Ile Glu Leu Thr Gln Ser Pro Ala Ile Met Ser Ala Ser Pro Gly
  1               5                  10                  15

Glu Lys Val Ile Met Thr Cys Ser Ala Ser Ser Ser Val Ser Tyr Met
                 20                  25                  30

His Trp Tyr Gln Gln Lys Ser Gly Thr Ser Pro Lys Arg Trp Ile Tyr
             35                  40                  45

Asp Thr Ser Lys Leu Ala Ser Gly Val Pro Ala Arg Phe Ser Gly Ser
         50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Ser Asn Pro Leu Thr
                    85                  90                  95

Phe Gly Ala Gly Thr Lys Leu Glu Leu Lys Arg
                100                 105

<210> SEQ ID NO 262
<211> LENGTH: 107
<212> TYPE: PRT
<213> ORGANISM: Artificial Sequence
<220> FEATURE:
<223> OTHER INFORMATION: single chain antibody
```

-continued

<400> SEQUENCE: 262

Asp Ile Glu Leu Thr Gln Ser Pro Ala Ile Met Ser Ala Ser Pro Gly
1               5                   10                  15

Glu Lys Val Ile Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg
            100                 105

<210> SEQ ID NO 263
<211> LENGTH: 112
<212> TYPE: PRT
<213> ORGANISM: Artificial Sequence
<220> FEATURE:
<223> OTHER INFORMATION: single chain antibody

<400> SEQUENCE: 263

Asp Ile Glu Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Tyr Thr Phe Gly Gly Gly Thr Lys Leu Glu Ile Lys Arg
            100                 105                 110

<210> SEQ ID NO 264
<211> LENGTH: 112
<212> TYPE: PRT
<213> ORGANISM: Artificial Sequence
<220> FEATURE:
<223> OTHER INFORMATION: single chain antibody

<400> SEQUENCE: 264

Asp Ile Glu Leu Thr Gln Ser Pro Thr Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

```
Pro Val Glu Ala Asp Asp Ala Ala Thr Tyr Tyr Cys Gln Gln Asn Asn
                85                  90                  95

Glu Asp Pro Tyr Thr Phe Gly Gly Gly Thr Lys Leu Glu Ile Lys Arg
            100                 105                 110

<210> SEQ ID NO 265
<211> LENGTH: 112
<212> TYPE: PRT
<213> ORGANISM: Artificial Sequence
<220> FEATURE:
<223> OTHER INFORMATION: single chain antibody

<400> SEQUENCE: 265

Asp Ile Glu Leu Thr Gln Ser Pro Ala Ser Leu Ala Val Ser Leu Gly
 1               5                  10                  15

Arg Arg Ala Thr Ile Ser Cys Arg Ala Ser Glu Ser Val Asp Ser Tyr
                20                  25                  30

Gly His Ser Phe Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
        50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Tyr Thr Phe Gly Gly Gly Thr Lys Leu Glu Ile Lys Arg
            100                 105                 110

<210> SEQ ID NO 266
<211> LENGTH: 112
<212> TYPE: PRT
<213> ORGANISM: Artificial Sequence
<220> FEATURE:
<223> OTHER INFORMATION: single chain antibody

<400> SEQUENCE: 266

Asp Ile Glu Leu Thr Gln Ser Pro Ala Ser Leu Ala Val Ser Leu Gly
 1               5                  10                  15

Gln Arg Ala Thr Ile Ser Cys Arg Ala Ser Glu Ser Val Asp Ser Tyr
                20                  25                  30

Gly His Ser Phe Met Gln Trp Tyr Gln Gln Lys Pro Gly Gln Pro Pro
            35                  40                  45

Lys Leu Leu Ile Tyr Arg Ala Ser Asn Leu Glu Pro Gly Ile Pro Ala
        50                  55                  60

Arg Phe Ser Gly Ser Gly Ser Gly Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Phe Thr Phe Gly Ser Gly Thr Lys Leu Glu Ile Lys Arg
            100                 105                 110

<210> SEQ ID NO 267
<211> LENGTH: 107
<212> TYPE: PRT
<213> ORGANISM: Artificial Sequence
<220> FEATURE:
<223> OTHER INFORMATION: single chain antibody

<400> SEQUENCE: 267

Asp Ile Glu Leu Thr Gln Ser Pro Ala Ile Met Ser Ala Ser Pro Gly
 1               5                  10                  15
```

Glu Lys Val Thr Thr Thr Cys Ser Ala Ser Ser Ser Val Ser Tyr Met
            20                  25                  30

Gly Trp Phe Gln Gln Lys Pro Gly Thr Ser Pro Lys Leu Trp Ile Tyr
            35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Tyr Thr
                85                  90                  95

Phe Gly Ser Gly Asp Gln Ala Gly Asn Lys Ser
            100                 105

<210> SEQ ID NO 268
<211> LENGTH: 112
<212> TYPE: PRT
<213> ORGANISM: Artificial Sequence
<220> FEATURE:
<223> OTHER INFORMATION: single chain antibody

<400> SEQUENCE: 268

Asp Ile Glu Leu Thr Gln Ser Pro Ala Ile Met Ser Ala Ser Pro Gly
1               5                   10                  15

Glu Lys Val Thr Thr Thr Cys Arg Ala Ser Gly Ser Val Asp Ser Tyr
            20                  25                  30

Gly His Ser Phe Met Gln Trp Phe Gln Gln Lys Pro Gly Thr Ser Pro
            35                  40                  45

Lys Leu Trp Ile Tyr Ser Thr Ser Asn Leu Ala Ser Gly Val Pro Ala
    50                  55                  60

Arg Phe Ser Gly Ser Gly Ser Gly Thr Ser Tyr Ser Leu Thr Ile Ser
65                  70                  75                  80

Arg Met Glu Ala Glu Asp Ala Ala Thr Tyr Tyr Cys Gln Gln Arg Ser
                85                  90                  95

Ser Tyr Pro Tyr Thr Phe Gly Ser Gly Asp Gln Ala Gly Asn Lys Arg
            100                 105                 110

<210> SEQ ID NO 269
<211> LENGTH: 107
<212> TYPE: PRT
<213> ORGANISM: Artificial Sequence
<220> FEATURE:
<223> OTHER INFORMATION: single chain antibody

<400> SEQUENCE: 269

Asp Thr Glu Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Gly Ser Ser Pro Arg Leu Leu Ile Tyr
            35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Pro Thr
                85                  90                  95

Phe Gly Ser Gly Thr Lys Leu Glu Ile Lys Arg
            100                 105

```
<210> SEQ ID NO 270
<211> LENGTH: 109
<212> TYPE: PRT
<213> ORGANISM: Artificial Sequence
<220> FEATURE:
<223> OTHER INFORMATION: single chain antibody

<400> SEQUENCE: 270

Asp Ile Glu Leu Thr Gln Ser Pro Ala Ile Met Ser Ala Ser Pro Gly
  1               5                  10                  15

Glu Lys Val Thr Met Thr Cys Arg Ala Ser Ser Ser Val Ser Ser Ser
             20                  25                  30

Tyr Leu Gly Trp Tyr Gln Gln Lys Pro Gly Ser Ser Pro Arg Leu Leu
         35                  40                  45

Ile Tyr Asp Thr Ser Asn Leu Ala Ser Gly Val Pro Val Arg Phe Ser
 50                  55                  60

Gly Ser Gly Ser Gly Thr Ser Tyr Ser Leu Thr Ile Ser Arg Met Glu
 65                  70                  75                  80

Ala Glu Asp Ala Ala Thr Tyr Tyr Cys Gln Gln Trp Ser Ser Tyr Pro
                 85                  90                  95

Pro Thr Phe Gly Ser Gly Thr Lys Leu Glu Ile Lys Arg
            100                 105

<210> SEQ ID NO 271
<211> LENGTH: 109
<212> TYPE: PRT
<213> ORGANISM: Artificial Sequence
<220> FEATURE:
<223> OTHER INFORMATION: single chain antibody

<400> SEQUENCE: 271

Asp Ser Glu Leu Thr Gln Ser Pro Thr Thr Met Ala Ala Ser Pro Gly
  1               5                  10                  15

Glu Lys Ile Thr Thr Thr Cys Ser Ala Ser Ser Ser Ile Ser Ser Asn
             20                  25                  30

Tyr Leu His Trp Tyr Gln Gln Arg Pro Gly Phe Ser Pro Lys Leu Leu
         35                  40                  45

Ile Tyr Arg Thr Ser Asn Leu Ala Ser Gly Val Pro Ala Arg Phe Ser
 50                  55                  60

Gly Ser Gly Ser Gly Thr Ser Tyr Ser Leu Thr Ile Gly Thr Met Glu
 65                  70                  75                  80

Ala Glu Asp Val Ala Thr Tyr Tyr Cys Gln Gln Gly Ser Ser Ile Pro
                 85                  90                  95

Arg Thr Phe Gly Gly Gly Thr Lys Leu Glu Ile Lys Arg
            100                 105

<210> SEQ ID NO 272
<211> LENGTH: 111
<212> TYPE: PRT
<213> ORGANISM: Artificial Sequence
<220> FEATURE:
<223> OTHER INFORMATION: single chain antibody

<400> SEQUENCE: 272

Asp Ile Glu Leu Thr Gln Ser Pro Ala Ser Leu Ala Val Ser Leu Gly
  1               5                  10                  15

Arg Arg Ala Thr Thr Ser Cys Arg Ala Ser Glu Ser Val Glu Tyr Tyr
             20                  25                  30

Gly Thr Ser Leu Met Gln Trp Tyr Gln Gln Lys Pro Gly Gln Pro Pro
         35                  40                  45
```

```
Lys Leu Leu Ile Tyr Ala Ala Ser Asn Val Glu Ser Gly Val Pro Ala
             50                  55                  60

Arg Phe Ser Gly Ser Gly Ser Gly Thr Asp Phe Ser Leu Asn Ile His
 65                  70                  75                  80

Pro Val Glu Glu Asp Ile Ala Met Tyr Phe Cys Gln Gln Ser Arg Lys
                 85                  90                  95

Val Pro Trp Thr Phe Gly Gly Gly Thr Lys Leu Glu Ile Lys Arg
            100                 105                 110
```

<210> SEQ ID NO 273
<211> LENGTH: 112
<212> TYPE: PRT
<213> ORGANISM: Artificial Sequence
<220> FEATURE:
<223> OTHER INFORMATION: single chain antibody

<400> SEQUENCE: 273

```
Tyr Ile Glu Leu Thr Gln Ser Pro Ala Ser Leu Ala Val Ser Leu Gly
  1               5                  10                  15

Gln Arg Ala Thr Thr Ser Cys Arg Ala Ser Glu Ser Val Asp Ser Tyr
                 20                  25                  30

Gly Asn Ser Phe Met His Trp Tyr Gln Gln Lys Pro Gly Gln Pro Pro
             35                  40                  45

Lys Leu Leu Ile Tyr Leu Ala Ser Asn Leu Glu Ser Gly Val Pro Ala
         50                  55                  60

Arg Phe Ser Gly Ser Gly Ser Arg Thr Asp Phe Thr Leu Thr Ile Asp
 65                  70                  75                  80

Pro Val Glu Ala Asp Asp Ala Ala Thr Tyr Tyr Cys Gln Gln Asn Asn
                 85                  90                  95

Glu Asp Pro Tyr Thr Phe Gly Gly Gly Thr Lys Leu Glu Ile Lys Ser
            100                 105                 110
```

<210> SEQ ID NO 274
<211> LENGTH: 112
<212> TYPE: PRT
<213> ORGANISM: Artificial Sequence
<220> FEATURE:
<223> OTHER INFORMATION: single chain antibody

<400> SEQUENCE: 274

```
Asp Ile Glu Leu Thr Gln Ser Pro Ala Ser Leu Ala Val Ser Leu Gly
  1               5                  10                  15

Gln Arg Ala Thr Thr Ser Cys Arg Ala Ser Glu Ser Val Glu Tyr Tyr
                 20                  25                  30

Gly Thr Ser Leu Met Gln Trp Tyr Gln Gln Lys Pro Gly Gln Pro Pro
             35                  40                  45

Lys Leu Leu Ile Tyr Ala Ala Ser Asn Val Glu Ser Gly Ala Pro Ala
         50                  55                  60

Arg Phe Ser Gly Ser Gly Ser Gly Thr Asp Phe Ser Leu Asn Ile His
 65                  70                  75                  80

Pro Val Glu Glu Asp Asp Ile Ala Met Tyr Phe Cys Gln Gln Ser Arg
                 85                  90                  95

Lys Val Pro Tyr Thr Phe Gly Gly Gly Thr Lys Leu Glu Ile Lys Arg
            100                 105                 110
```

<210> SEQ ID NO 275
<211> LENGTH: 109
<212> TYPE: PRT
<213> ORGANISM: Artificial Sequence

```
<220> FEATURE:
<223> OTHER INFORMATION: single chain antibody

<400> SEQUENCE: 275

Asp Ile Glu Leu Thr Gln Ser Pro Ala Ile Met Ser Ala Ser Pro Gly
1               5                   10                  15

Glu Lys Val Thr Thr Thr Cys Ser Val Ser Ser Ile Ser Ser Ser
            20                  25                  30

Asn Leu His Trp Tyr Gln Gln Lys Ser Gly Thr Ser Pro Lys Leu Trp
        35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Tyr Pro
                85                  90                  95

Leu Thr Phe Gly Ala Gly Thr Lys Val Glu Leu Arg Arg
            100                 105

<210> SEQ ID NO 276
<211> LENGTH: 109
<212> TYPE: PRT
<213> ORGANISM: Artificial Sequence
<220> FEATURE:
<223> OTHER INFORMATION: single chain antibody

<400> SEQUENCE: 276

Asp Ile Glu Leu Thr Gln Ser Pro Ala Ser Met Ser Ala Ser Pro Gly
1               5                   10                  15

Glu Lys Val Thr Met Thr Cys Arg Ala Thr Ser Ser Val Ser Ser Ser
            20                  25                  30

Tyr Leu His Trp Tyr Gln Gln Lys Ser Gly Ala Ser Pro Lys Leu Trp
        35                  40                  45

Ile Tyr Ser Ala Ser Asn Leu Ala Ser Gly Val Pro Ser Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ile Gly Tyr Pro
                85                  90                  95

Tyr Thr Phe Gly Gly Gly Thr Lys Leu Glu Ile Lys Arg
            100                 105

<210> SEQ ID NO 277
<211> LENGTH: 109
<212> TYPE: PRT
<213> ORGANISM: Artificial Sequence
<220> FEATURE:
<223> OTHER INFORMATION: single chain antibody

<400> SEQUENCE: 277

Asp Ile Glu Leu Thr Gln Ser Pro Thr Thr Met Ala Ala Ser Pro Gly
1               5                   10                  15

Glu Lys Ile Thr Ile Thr Cys Ser Ala Ser Ser Ser Ile Gly Ser Asn
            20                  25                  30

Tyr Leu His Trp Tyr Gln Gln Lys Pro Gly Phe Ser Pro Lys Leu Leu
        35                  40                  45

Ile Tyr Arg Thr Ser Asn Leu Ala Ser Gly Val Pro Ala Arg Phe Ser
    50                  55                  60
```

```
Gly Ser Gly Ser Gly Thr Ser Tyr Ser Leu Thr Ile Gly Ala Met Glu
65                  70                  75                  80

Ala Glu Asp Val Ala Thr Tyr Tyr Cys Gln Gln Gly Ser Ser Ile Pro
                85                  90                  95

Tyr Thr Phe Gly Gly Gly Thr Lys Leu Glu Ile Lys Arg
            100                 105

<210> SEQ ID NO 278
<211> LENGTH: 7
<212> TYPE: PRT
<213> ORGANISM: Artificial Sequence
<220> FEATURE:
<223> OTHER INFORMATION: peptide linker

<400> SEQUENCE: 278

Gly Gly Gly Gly Ser Ser Ser
1               5
```

THERAPEUTIC MONOCLONAL ANTIBODIES THAT NEUTRALIZE BOTULINUM NEUROTOXINS

CROSS-REFERENCE TO RELATED APPLICATIONS

This application is a Divisional application of U.S. Ser. No. 10/632,706 filed Aug. 1, 2003, now U.S. Pat. No. 7,563,874 which application claims priority to and benefit of U.S. Ser. No. 60/400,721, filed on Aug. 1, 2002, and which application is a continuation-in-part of U.S. Ser. No. 09/144,886, filed Aug. 31, 1998, now abandoned, all of which are incorporated herein by reference in their entirety for all purposes.

STATEMENT AS TO RIGHTS TO INVENTIONS MADE UNDER FEDERALLY SPONSORED RESEARCH AND DEVELOPMENT

This work was partially supported by the U.S. Army Medical Research and Development Command under award no. DAMD17-74-C-4034. The Government of the United States of America has certain rights in this invention.

FIELD OF THE INVENTION

This invention relates antibodies that neutralize botulinum neurotoxin type A (BoNT/A) and their use in the treatment of botulism.

BACKGROUND OF THE INVENTION

Botulism is a life-threatening, flaccid paralysis caused by a neurotoxin produced by the anaerobic bacterium *Clostridium botulinum*. The disease typically results from ingestion of pre-formed toxin present in contaminated food (Dowell (1984) *Rev. Infect. Dis.* 6(Suppl. 1): S202-S207), from toxin produced in vivo from infected wounds (Weber (1993) *Clin. Infect. Dis.*, 16: 635-639, in the intestines of infants (Amon (1992) in *Textbook of pediatric infectious diseases*, R. D. Feigen and J. D. Chemy (ed.), 3rd ed., Saunders, Philadelphia, Pa.), or occasionally in adults.

In severe cases, patients require prolonged hospitalization in an intensive-care unit and mechanical ventilation. Specific therapy consists of administration of botulism antitoxin trivalent (equine) (Tacket et al. *Am. J. Med.,* 76: 794-798); however, this product has a high incidence of side effects, including serum sickness and anaphylaxis (Black, et al. (1980) *Am. J. Med.,* 69: 567-570). To avoid these side effects, human BIG has been produced from immunized volunteers and its efficacy is being determined in a prospective randomized trial in infants with botulism (Amon (1993) pages 477-482 in *Botulinum and tetanus neurotoxins: neurotransmission and biomedical aspects*, B. R. DasGupta (ed.), Plenum, New York, N.Y.). While theoretically nontoxic, human BIG also has limitations, largely related to production issues. These include potential transmission of blood-borne infectious diseases, variability in potency and specificity between lots, and the need to immunize humans. The latter issue has taken on increased importance with the use of BoNTs for the treatment of a range of neuromuscular diseases (Jankovic et al. (1994) *Therapy with botulinum toxin*. Marcel Dekker, New York, N.Y.; Moore (1995) *Handbook of botulinum toxin treatment*, Blackwell Science, Oxford, United Kingdom) Immunization of volunteers for production of BIG would deprive them of subsequent botulinum therapy.

As an alternative to immune globulin, neutralizing monoclonal antibodies with defined potency and specificity could be produced in unlimited quantities. To date, however, no efficacious neutralizing antibotulinum monoclonal antibodies have been produced (Middlebrook, et al. (1995) *Curr. Top. Microbiol. Immunol.* 195:89-122). Potential explanations for this failure include the following: (i) a neutralizing epitope(s) is less immunogenic than other epitopes; (ii) too few unique monoclonal antibodies have been studied; (iii) a toxoid immunogen (formaldehyde-inactivated crude toxin) that poorly mimics the conformation of the neutralizing epitope(s) has been used; and (iv) multiple epitopes must be blocked in order to achieve efficient neutralization (Lang, et al. (1993) *J. Immunol.* 151: 466-473).

SUMMARY OF THE INVENTION

This invention provides novel antibodies that specifically bind to and neutralize botulinum neurotoxin type A (BoNT/A). In addition, the epitopes bound by these antibodies are provided. The antibodies and epitopes identified herein are suitable for the creation of fully human, or humanized (chimeric) whole (polyclonal or monoclonal) antibodies and/or antibody fragments. In addition the antibodies and/or variants thereof are useful in neutralizing botulinum neurotoxin type A and can be used to mitigate or eliminate symptoms of botulism.

Thus, in one embodiment, this invention provides an isolated antibody that specifically binds to an epitope specifically bound by an antibody expressed by a clone selected from the group consisting of clone S25, clone C25, clone C39, clone 1C6, clone 3D12, clone B4, clone 1F3, clone huC25, clone Art, clone Ar2, clone WR1(V), clone WR1(T), clone 3-1, clone 3-8, clone 3-10, and clone ING1. The antibody binds to and neutralizes botulinum neurotoxin type A (BoNT/A). The antibody can be of virtually any mammalian animal type (e.g. mouse, human, goat, rabbit) or chimeric (e.g. humanized), but is most preferably mouse, human, or humanized.

In one embodiment, the antibody comprises at least one (more preferably at least two and most preferably at least three) of the variable heavy ($V_H$) complementarity determining regions (CDRs) listed in Table 4, and/or Table 9 and/or Table 11 or conservative substitutions thereof. In another embodiment, the antibody comprises at least one (more preferably at least two and most preferably at least three) of the variable light ($V_L$) complementarity determining regions (CDRs) listed in Table 4, and/or Table 9 and/or Table 11 or conservative substitutions thereof. In still another embodiment, the antibody comprises at least one (more preferably at least two and most preferably at least three) of the variable heavy ($V_H$) complementarity determining regions (CDRs) listed in Table 4, and/or Table 9 and/or Table 11 or conservative substitutions thereof and at least one (more preferably at least two and most preferably at least three) of the variable light ($V_L$) complementarity determining regions (CDRs) listed in Table 4, and/or Table 9 and/or Table 11 or conservative substitutions thereof. Particularly preferred antibodies are antibodies expressed by a clone listed in Table 4, and/or Table 9 and/or Table 11 (or human or humanized variants thereof). Particularly preferred antibodies include an IgG, a single chain Fv (scFv), while other preferred antibodies include, but are not limited to a Fab, a $(Fab')_2$, and a $(scFv')_2$. The antibodies can include fusion proteins comprising of two scFv fragments. Particularly preferred antibodies comprise a framework (e.g., a $V_H$ or $V_L$ framework 1, framework 2, framework 3, framework 4 or combinations thereof (e.g., at least two, at least three, or four $V_L$ or $V_H$ frameworks)). region listed in Table 4, and/or Table 9 and/or Table 11. Other preferred embodiments include an antibody comprising a variable heavy ($V_H$) complementarity determining region (CDR) listed in Table 4, and/or Table 9 and/or Table 11 and wherein said antibody specifically binds to and neutralizes a botulinum neurotoxin type A. Preferred antibodies include one or more of the $V_H$ and/or $V_L$ CDR and/or framework regions as described herein.

This invention also provides for pharmaceutical compositions comprising one or more of the botulinum neurotoxin type A (BoNT/A)-neutralizing antibodies described herein in a pharamcological excipient.

This invention also provides methods of neutralizing a botulinum neurotoxin type A (BoNT/A). The methods involve contacting the botulinum neurotoxin type A with one or more of the BoNT/A-neutralizing antibodies described herein. Preferred antibodies have a specificity and affinity such that they specifically binds to binds to and neutralizes the botulinum neurotoxin type A. The methods can further involve contacting the BoNT/A with a second BoNT/A-neutralizing antibody.

This invention also provides BoNT/A-neutralizing epitopes. Preferred epitopes are BoNT/A $H_C$ epitopes specifically bound by an antibody expressed by clone S25, clone C25, clone C39, clone 106, clone 3D12, clone B4, clone 1F3, clone huC25, clone Ar1, clone Ar2, clone WR1(V), clone WR1(T), clone 3-1, clone 3-8, clone 3-10, and clone ING1. Particularly preferred polypeptides are not a full-length BoNT/A and more particularly preferred polypeptides are not a full-length BoNT/A $H_c$ fragment. Thus, most preferred epitopes are a BoNT/A $H_C$ subsequence or fragment with preferred subsequences having a length of at least 4, preferably at least 6, more preferably at least 8 and most preferably at least 10, 12, 14, or even 15 amino acids.

This invention also provides methods of making a botulinum neurotoxin type A antibody (anti-BoNT/A) that neutralizes BoNT/A. The methods involve contacting a plurality of antibodies with an epitope specifically bound by an antibody expressed one or more of clone S25, clone C25, clone C39, clone 106, clone 3D12, clone B4, clone 1F3, clone huC25, clone Ar1, clone Ar2, clone WR1(V), clone WR1(T), clone 3-1, clone 3-8, clone 3-10, and/or clone ING1. Particularly preferred epitopes are polypeptides that are not a full-length BoNT/A and more particularly preferred polypeptides are not a full-length BoNT/A $H_c$ fragment. Thus, most preferred epitopes are a BoNT/A $H_C$ subsequence or fragment with preferred subsequences having a length of at least 4, preferably at least 6, more preferably at least 8 and most preferably at least 10, 12, 14, or even 15 amino acids. The plurality of antibodies can include, but is not limited to antibodies displayed on a surface protein of a phage, and/or antibodies in serum from a mammal, and/or antibodies expressed by hybridomas.

DEFINITIONS

The following abbreviations are used herein: AMP, ampicillin; BIG, botulinum immune globulin; BoNT, botulinum neurotoxin; BoNT/A, BoNT type A; CDR, omplementarity determining region; ELISA, enzyme-linked immunosorbent assay; GLU, glucose; HBS, HEPES-buffered saline (10 mM HEPES, 150 mM NaCl [pH 7.4]); $H_c$, c-terminal domain of BoNT heavy chain (binding domain); $H_N$, N-terminal domain of BoNT heavy chain (translocation domain); IgG, immunoglobutin G; IMAC, immobilized-metal affinity chromatography; IPTG, isopropyl-β-D-thiogalactopyranoside; KAN, kanamycin; $K_d$, equilibrium constant; $k_{off}$, dissociation rate constant; $k_{on}$, association rate constant; MPBS, skim milk powder in PBS; NTA, nitrilotriacetic acid; PBS, phosphate-buffered saline (25 mM $NaH_2PO_4$, 125 mM NaCl [pH 7.0]; RU, resonance units; scFv, single-chain Fv antibody fragments; TPBS, 0.05% (vol/vol) Tween 20 in PBS; TMPBS, 0.05% (vol/vol) Tween 20 in MPBS; TU, transducing units; $V_H$, immunoglobulin heavy-chain variable region; $V_K$, immunoglobulin kappa light-chain variable region; $V_L$ immunoglobulin light-chain variable region; wt, wild type, BoNT/A, botulinum neurotoxin serotype A; $H_C$, botulinum neurotoxin binding domain; $H_N$, botulinum neurotoxin translocation domain; PBL, peripheral blood lymphocytes; RU, resonance unit; scFv, single-chain variable fragment; $V_H$, immunoglobulin heavy chain variable region; Vκ, immunoglobulin kappa light chain variable region; $V_L$, immunoglobulin lambda light chain variable region.

The terms "polypeptide", "peptide", or "protein" are used interchangeably herein to designate a linear series of amino acid residues connected one to the other by peptide bonds between the alpha-amino and carboxy groups of adjacent residues. The amino acid residues are preferably in the natural "L" isomeric form. However, residues in the "D" isomeric form can be substituted for any L-amino acid residue, as long as the desired functional property is retained by the polypeptide. In addition, the amino acids, in addition to the 20 "standard" amino acids, include modified and unusual amino acids, which include, but are not limited to those listed in 37 CFR (1.822(b)(4). Furthermore, it should be noted that a dash at the beginning or end of an amino acid residue sequence indicates either a peptide bond to a further sequence of one or more amino acid residues or a covalent bond to a carboxyl or hydroxyl end group.

The term "BoNT/A polypeptide" refers to either a full-length BoNT/A or a fragment thereof (e.g. the Hc fragment). BoNT/A is a neurotoxin produced by *Clostridium botulinum* of the type A serotype. The $H_C$ fragment is a 43 kDa C-terminal fragment (residues 860-1296) of BoNT/A (LaPenotiere et al. (1995) *Toxicon*, 33: 1383-1386).

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region thereby converting the (Fab')$_2$ dimer into an Fab' monomer. The Fab' monomer is essentially an Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies, more preferably single chain Fv (scFv) antibodies in which a variable heavy and a variable light chain are joined together (directly or through a peptide linker) to form a continuous polypeptide.

An "antigen-binding site" or "binding portion" refers to the part of an immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRs" and are characterized, for example by Kabat et al. *Sequences of proteins of immunological interest*, 4th ed. U.S. Dept. Health and Human Services, Public Health Services, Bethesda, Md. (1987).

As used herein, the terms "immunological binding" and "immunological binding properties" refer to the non-covalent interactions of the type which occur between an immunoglobulin molecule and an antigen for which the immunoglobulin is specific. The strength or affinity of immunological binding interactions can be expressed in terms of the dissociation constant ($K_d$) of the interaction, wherein a smaller Kd represents a greater affinity Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity and is thus equal to the dissociation constant $K_d$. See, generally, Davies et al. *Ann. Rev. Biochem.*, 59: 439-473 (1990).

The term "BoNT/A-neutralizing antibody", as used herein refers to an antibody that specifically binds to a BoNT/A polypeptide, more preferably to a BoNT/A $H_C$ polypeptide and that by so-binding reduces the toxicity of the BoNT/A polypeptide. Reduced toxicity can be measured as an increase in the time that paralysis developed and/or as a lethal dosage (e.g. $LD_{50}$) as described herein. Antibodies derived from BoNT/A-neutralizing antibodies include the antibodies whose sequence is expressly provided herein.

Antibodies derived from BoNT/A-neutralizing antibodies preferably have a binding affinity of about $1.6 \times 10^{-8}$ or better and are preferably derived by screening (for affinity to BoNT/A) a phage display library in which a known BoNT/A-neutralizing variable heavy ($V_H$) chain is expressed in combination with a multiplicity of variable light ($V_L$) chains or conversely a known BoNT/A-neutralizing variable light chain is expressed in combination with a multiplicity of variable heavy ($V_H$) chains. BoNT/A-neutralizing antibodies also include those antibodies produced by the introduction of mutations into the variable heavy or variable light complementarity determining regions (CDR1, CDR2 or CDR3) as described herein. Finally BoNT/A-neutralizing antibodies include those antibodies produced by any combination of these modification methods as applied to the BoNT/A-neutralizing antibodies described herein and their derivatives.

A neutralizing epitope refers to the epitope specifically bound by a neutralizing antibody.

A single chain Fv ("scFv" or "scFv") polypeptide is a covalently linked $V_H::V_L$ heterodimer which may be expressed from a nucleic acid including $V_H$- and $V_L$-encoding sequences either joined directly or joined by a peptide-encoding linker. Huston, et al. (1988) *Proc. Nat. Acad. Sci. USA*, 85: 5879-5883. A number of structures for converting the naturally aggregated—but chemically separated light and heavy polypeptide chains from an antibody V region into an scFv molecule which will fold into a three dimensional structure substantially similar to the structure of an antigen-binding site. See, e.g. U.S. Pat. Nos. 5,091,513 and 5,132,405 and 4,956,778.

In one class of embodiments, recombinant design methods can be used to develop suitable chemical structures (linkers) for converting two naturally associated—but chemically separate—heavy and light polypeptide chains from an antibody variable region into a scFv molecule which will fold into a three-dimensional structure that is substantially similar to native antibody structure.

Design criteria include determination of the appropriate length to span the distance between the C-terminal of one chain and the N-terminal of the other, wherein the linker is generally formed from small hydrophilic amino acid residues that do not tend to coil or form secondary structures. Such methods have been described in the art. See, e.g., U.S. Pat. Nos. 5,091,513 and 5,132,405 to Huston et al.; and U.S. Pat. No. 4,946,778 to Ladner et al.

In this regard, the first general step of linker design involves identification of plausible sites to be linked. Appropriate linkage sites on each of the $V_H$ and $V_L$ polypeptide domains include those which will result in the minimum loss of residues from the polypeptide domains, and which will necessitate a linker comprising a minimum number of residues consistent with the need for molecule stability. A pair of sites defines a "gap" to be linked. Linkers connecting the C-terminus of one domain to the N-terminus of the next generally comprise hydrophilic amino acids which assume an unstructured configuration in physiological solutions and preferably are free of residues having large side groups which might interfere with proper folding of the $V_H$ and $V_L$ chains. Thus, suitable linkers under the invention generally comprise polypeptide chains of alternating sets of glycine and serine residues, and may include glutamic acid and lysine residues inserted to enhance solubility. One particular linker under the invention has the amino acid sequence [(Gly)$_4$Ser]$_3$ (SEQ ID NO: 226). Another particularly preferred linker has the amino acid sequence comprising 2 or 3 repeats of [(Ser)$_4$Gly] (SEQ ID NO: 227) such as [(Ser)$_4$Gly]$_3$ (SEQ ID NO: 228) Nucleotide sequences encoding such linker moieties can be readily provided using various oligonucleotide synthesis techniques known in the art. See, e.g., Sambrook, supra.

The phrase "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to a protein under such conditions may require an antibody that is selected for its specificity for a particular protein. For example, BoNT/A-neutralizing antibodies can be raised to the BoNT/A protein that specifically bind to BoNT/A and not to other proteins present in a tissue sample. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity.

The term "conservative substitution" is used in reference to proteins or peptides to reflect amino acid substitutions that do not substantially alter the activity (specificity or binding affinity) of the molecule. Typically conservative amino acid substitutions involve substitution one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

BRIEF DESCRIPTION OF THE DRAWINGS

FIG. 3 shows the evaluation of scFv neutralization of BoNT/A in a mouse hemidiaphragm model. The twitch tension developed after electrical stimulation of a mouse hemidiaphragm was measured below (−30 to 0 min) and after the addition of 20 pM BoNT/a (control), 2 pM BoNT/A plus 20 nM scFv S25, C25, 1BoNT/A-neutralizing, or 1F3 (representing epitopes 1 to 4 respectively), or a combination of S25 and C25 at a final concentration of 20 nM each. Results are expressed as the fraction of steady-state twitch tension (at 0 min) versus time. scFv 106 and 1F3 do not alter the time to 50% twitch reduction, whereas scFv C25 and S25 significantly prolong it. The combination of S25 and C25 significantly prolonged the time to neuroparalysis compared to C25 or S25 alone.

FIG. 7 shows solution equilibrium dissociation constants ($K_d$) of antibodies. The solution $K_d$ of single mAb C25 and 3D12 were determined in a flow fluorimeter by measuring the amount of free Ab present as a function of increasing BoNT $H_C$ toxin. Combining C25 and 3D12 mAb in equimolar amounts decreased the C25 $K_d$ more than 100-fold. Adding a third Ab (S25) decreased the Kd another 4-fold to 18 pM.

FIGS. 8A and 8B show ELISA characterization of soluble scFv antibodies. Assays were performed by immobilizing each indicated BoNT serotype, BoNT/A HC and BoNT/A HN coated onto a polystyrene plate. FIG. 8A: Bacterially expressed scFv antibodies derived from the immune library, reactive with the coated antigen was detected with the peroxidase-conjugated mAb anti-E antibody (1:2500). FIG. 8B: Bacterially expressed scFv antibodies derived from the non-immune library, reactive with the coated antigen were detected with 9E10 antibody (1:500) followed by peroxidase-conjugated anti-mouse-Fc antibody. The results of the assay are shown as absorbance at 405 nm which have not been normalized for protein concentrations.

FIG. 9A: The scFv 3A6 and 3D12 recognize the same epitope, as indicated by no increase in the RU bound when the two scFv are mixed. FIG. 9B: scFv 2A9 and 2A1 recognize different epitopes, as indicated by an almost additive increase in the RU bound when the two scFv are mixed.

FIG. 10A: The twitch tension developed after electrical stimulation of a mouse hemidiaphragm was measured before (−30 to 0 min) and after the addition of 20 pM BoNT/A (control), 20 pM BoNT/A plus 20 nM of members of cluster I (3D12), cluster II (3F10), C25 or S25. The scFv 3F10 did not alter the time to 50% twitch reduction, whereas scFv C25, S25 or 3D12 significantly prolong the time to 50% twitch reduction. FIG. 10B: The combination of C25 with S25 or 3D12 (cluster I) prolong significantly the time to 50% twitch reduction.

DETAILED DESCRIPTION

Figure 1:
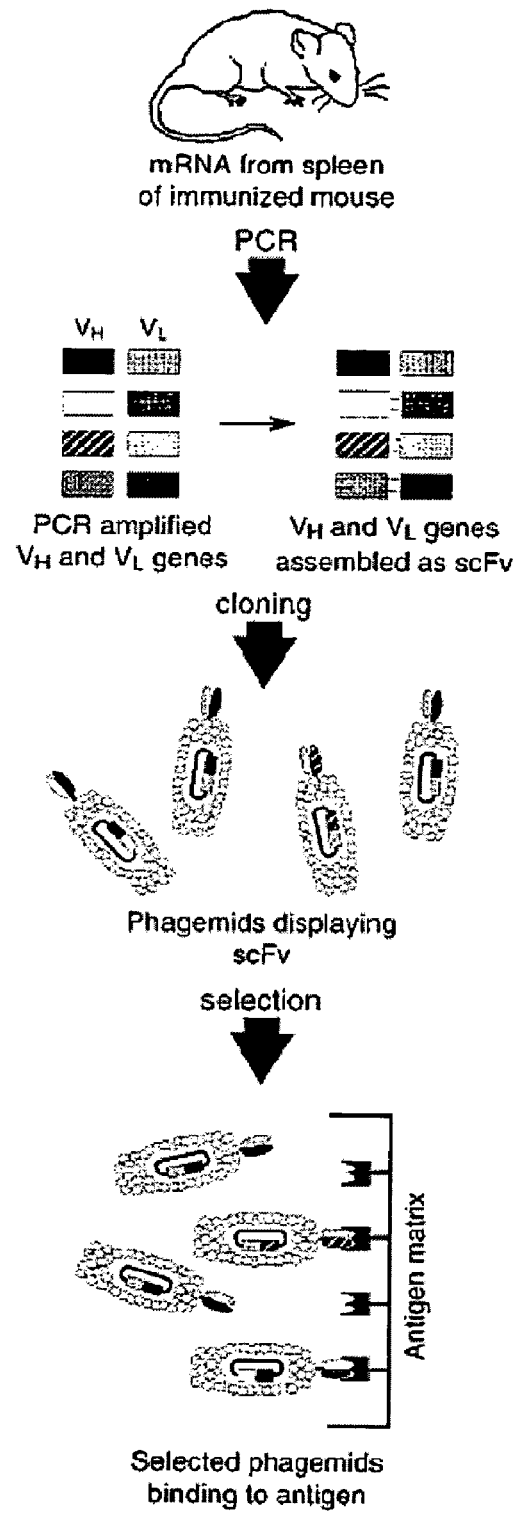
FIG. 1 Illustrates the strategy for in vitro antibody production using phage libraries. mRNA is prepared from splenocytes, first-strand cDNA is prepared, and antibody $V_H$ and $V_L$ genes are amplified by PCR. $V_H$ and $V_L$ genes are spliced together randomly using PCR to create a repertoire of scFv genes. The scFv gene repertoire is cloned into a phagemid vector in frame with a gene (gIII) encoding a phagemid minor coat protein (pIII). Each phage in the resulting phage antibody library expresses and scFv-pIII fusion protein on its surface and contains the gene encoding the scFv inside. Phage antibodies binding a specific antigen can be separated from nonbinding phage antibodies by affinity chromatography on immobilized antigen. A single round of selection increases the number of antigen-binding phage antibodies by a factor ranging from 20 to 10,000 depending on the affinity of the antibody. Eluted phage antibodies are used to infect E. coli, which then produce more phage antibodies for the next round of selection. Repeated rounds of selection make it possible to isolate antigen-binding phage antibodies that were originally present at frequencies of less than one in a billion.

This invention provides novel antibodies that specifically bind to and neutralize botulinum neurotoxin type A, a neurotoxin produced by the anaerobic bacterium *Clostridium botulinum*. Botulinum neurotoxin poisoning (botulism) arises in a number of contexts including, but not limited to food poisoning (food borne botulism), infected wounds (wound botulism), and "infant botulism" from ingestion of spores and production of toxin in the intestine of infants. Botulism is a paralytic disease that typically begins with cranial nerve involvement and progresses caudally to involve the extremities. In acute cases, botulism can prove fatal.

The antibodies provided by this invention bind to and neutralize botulinum neurotoxin type A (BoNT/A). Neutralization, in this context, refers to a measurable decrease in the toxicity of BoNT/A. Such a decrease in toxicity can be measured in vitro by a number of methods well known to those of skill in the art. One such assay involves measuring the time to a given percentage (e.g. 50%) twitch tension reduction in a hemidiaphragm preparation. Toxicity can be determined in vivo, e.g. as an $LD_{50}$ in a test animal (e.g. mouse) botulinum neurotoxin type A in the presence of one or more putative neutralizing antibodies. The neutralizing antibody can be combined with the botulinum neurotoxin prior to administration, or the animal can be administered the antibody prior to, simultaneous with, or after administration of the neurotoxin.

As the antibodies of this invention act to neutralize botulinum neurotoxin type A, they are useful in the treatment of pathologies associated with botulinum neurotoxin poisoning. The treatments essentially comprise administering to the poisoned organism (e.g. human or non-human mammal) a quantity of BoNT/A neutralizing antibody sufficient to neutralize (e.g. mitigate or eliminate) symptoms of BoNT/A poisoning.

Such treatments are most desired and efficacious in acute cases (e.g. where vital capacity is less than 30-40 percent of predicted and/or paralysis is progressing rapidly and/or hypoxemia with absolute or relative hypercarbia is present. Treatment with the neutralizing can be provided as a adjunct to other therapies (e.g. antibiotic treatment).

The antibodies provided by this invention can also be used for the rapid detection/diagnosis of botulism (type A toxin) and thereby supplement and/or replace previous laboratory diagnostics.

In another embodiment this invention provides the epitopes specifically bound by botulinum neurotoxin type A neutralizing antibodies. These epitopes can be used to isolate, and/or identify and/or screen for other antibodies BoNT/A neutralizing antibodies as described herein.

I. Preparation of BoNT/A Neutralizing Antibodies.

A) Recombinant Expression of BoNT/A-Neutralizing Antibodies.

Using the information provided herein, the botulinum neurotoxin type A (BoNT/A)-neutralizing antibodies of this invention are prepared using standard techniques well known to those of skill in the art.

For example, the polypeptide sequences provided herein (see, e.g., Table 4, Table 9, and/or Table 11) can be used to determine appropriate nucleic acid sequences encoding the BoNT/A-neutralizing antibodies and the nucleic acids sequences then used to express one or more BoNT/A-neutralizing antibodies. The nucleic acid sequence may be optimized to reflect particular codon "preferences" for various expression systems according to standard methods well known to those of skill in the art.

Using the sequence information provided, the nucleic acids may be synthesized according to a number of standard methods known to those of skill in the art. Oligonucleotide synthesis, is preferably carried out on commercially available solid phase oligonucleotide synthesis machines (Needham-VanDevanter et al. (1984) *Nucleic Acids Res.* 12:6159-6168) or manually synthesized using the solid phase phosphoramidite triester method described by Beaucage et. al. (Beaucage et. al. (1981) *Tetrahedron Letts.* 22(20): 1859-1862).

Once a nucleic acid encoding a BoNT/A-neutralizing antibody is synthesized it may be amplified and/or cloned according to standard methods. Molecular cloning techniques to achieve these ends are known in the art. A wide variety of cloning and in vitro amplification methods suitable for the construction of recombinant nucleic acids are known to persons of skill. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, NY, (Sambrook); and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Methods of producing recombinant immunoglobulins are also known in the art. See, Cabilly, U.S. Pat. No. 4,816,567; and Queen et al. (1989) *Proc. Nat'l Acad. Sci. USA* 86: 10029-10033.

Examples of techniques sufficient to direct persons of skill through in vitro amplification methods, including the polymerase chain reaction (PCR) the ligase chain reaction (LCR), Qβ-replicase amplification and other RNA polymerase mediated techniques are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis);

Arnheim & Levinson (Oct. 1, 1990) *C&EN* 36-47; *The Journal Of NIH Research* (1991) 3, 81-94; (Kwoh et al. (1989) *Proc. Natl. Acad. Sci. USA* 86, 1173; Guatelli et al. (1990) *Proc. Natl. Acad. Sci. USA* 87, 1874; Lomeli et al. (1989) *J. Clin. Chem.* 35, 1826; Landegren et al., (1988) *Science* 241, 1077-1080; Van Brunt (1990) *Biotechnology* 8, 291-294; Wu and Wallace, (1989) *Gene* 4, 560; and Barringer et al. (1990) *Gene* 89, 117. Improved methods of cloning in vitro amplified nucleic acids are described in Wallace et al., U.S. Pat. No. 5,426,039.

Once the nucleic acid for a BoNT/A-neutralizing antibody is isolated and cloned, one may express the gene in a variety of recombinantly engineered cells known to those of skill in the art. Examples of such cells include bacteria, yeast, filamentous fungi, insect (especially employing baculoviral vectors), and mammalian cells. It is expected that those of skill in the art are knowledgeable in the numerous expression systems available for expression of BoNT/A-neutralizing antibodies.

In brief summary, the expression of natural or synthetic nucleic acids encoding BoNT/A-neutralizing antibodies will typically be achieved by operably linking a nucleic acid encoding the antibody to a promoter (which is either constitutive or inducible), and incorporating the construct into an expression vector. The vectors can be suitable for replication and integration in prokaryotes, eukaryotes, or both. Typical cloning vectors contain transcription and translation terminators, initiation sequences, and promoters useful for regulation of the expression of the nucleic acid encoding the BoNT/A-neutralizing antibody. The vectors optionally comprise generic expression cassettes containing at least one independent terminator sequence, sequences permitting replication of the cassette in both eukaryotes and prokaryotes, i.e., shuttle vectors, and selection markers for both prokaryotic and eukaryotic systems. See Sambrook.

To obtain high levels of expression of a cloned nucleic acid it is common to construct expression plasmids which typically contain a strong promoter to direct transcription, a ribosome binding site for translational initiation, and a transcription/translation terminator. Examples of regulatory regions suitable for this purpose in *E. coli* are the promoter and operator region of the *E. coli* tryptophan biosynthetic pathway as described by Yanofsky, (1984) *J. Bacteriol.,* 158: 1018-1024 and the leftward promoter of phage lambda ($P_L$) as described by Herskowitz and Hagen (1980) *Ann. Rev. Genet.,* 14:399-445. The inclusion of selection markers in DNA vectors transformed in *E. coli* is also useful. Examples of such markers include genes specifying resistance to ampicillin, tetracycline, or chloramphenicol. See Sambrook for details concerning selection markers, e.g., for use in *E. coli.*

Expression systems for expressing BoNT/A-neutralizing antibodies are available using *E. coli, Bacillus* sp. (Palva, et al. (1983) *Gene* 22:229-235; Mosbach et al., *Nature,* 302: 543-545 and *Salmonella. E. coli* systems are preferred.

The BoNT/A-neutralizing antibodies produced by prokaryotic cells may require exposure to chaotropic agents for proper folding. During purification from, e.g., *E. coli,* the expressed protein is optionally denatured and then renatured. This is accomplished, e.g., by solubilizing the bacterially produced antibodies in a chaotropic agent such as guanidine HCl. The antibody is then renatured, either by slow dialysis or by gel filtration. See, U.S. Pat. No. 4,511,503.

Methods of transfecting and expressing genes in mammalian cells are known in the art. Transducing cells with nucleic acids can involve, for example, incubating viral vectors containing BoNT/A-neutralizing nucleic acids with cells within the host range of the vector. See, e.g., Goeddel (1990) *Methods in Enzymology,* vol. 185, Academic Press, Inc., San Diego, Calif. or Krieger (1990) *Gene Transfer and Expression—A Laboratory Manual,* Stockton Press, New York, N.Y. and the references cited therein.

The culture of cells used in the present invention, including cell lines and cultured cells from tissue or blood samples is well known in the art (see, e.g., Freshney (1994) *Culture of Animal Cells, a Manual of Basic Technique, third edition,* Wiley-Liss, N.Y. and the references cited therein).

Techniques for using and manipulating antibodies are found in Coligan (1991) *Current Protocols in Immunology* Wiley/Greene, N.Y.; Harlow and Lane (1989) *Antibodies: A Laboratory Manual* Cold Spring Harbor Press, NY; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) Nature 256: 495-497. BoNT/A-neutralizing antibodies that are specific for botulinum neurotoxin type A have a $K_D$ of $1 \times 10^{-8}$ M or better, with preferred embodiments having a $K_D$ of 1 nM or better and most preferred embodiments having a $K_D$ of 0.1 nM or better.

In one preferred embodiment the BoNT/A-neutralizing antibody gene (e.g. BoNT/A-neutralizing.5 scFv gene) is subcloned into the expression vector pUC119mycHis (Tomlinson et al. (1996) *J. Mol. Biol.,* 256: 813-817) or pSYN3, resulting in the addition of a hexahistidine tag at the C-terminal end of the scFv to facilitate purification. Detailed protocols for the cloning and purification of BoNT/A-neutralizing antibodies are provided in Example 1.

B) Preparation of Whole Polyclonal or Monoclonal Antibodies.

BoNT/A-neutralizing antibodies of this invention include individual, allelic, strain, or species variants, and fragments thereof, both in their naturally occurring (full-length) forms and in recombinant forms. In certain embodiments, preferred antibodies are selected to bind one or more epitopes bound by antibodies expressed by clones S25, C25, C39, 1C6, 3D12, B4, 1F3, huC25, Ar1, Ar2, WR1(V), WR1(T), 3-1, 3-8, 3-10, and/or ING1 disclosed herein. The antibodies can be raised in their native configurations or in non-native configurations. Anti-idiotypic antibodies can also be generated. Many methods of making antibodies that specifically bind to a particular epitope are known to persons of skill. The following discussion is presented as a general overview of the techniques available; however, one of skill will recognize that many variations upon the following methods are known.

1) Polyclonal Antibody Production.

Methods of producing polyclonal antibodies are known to those of skill in the art. In brief, an immunogen (e.g., BoNT/A, BoNT/A $H_C$, or BoNT/A subsequences including, but not limited to subsequences comprising epitopes specifically bound by antibodies expressed by clones S25, C25, C39, 1-C6, 3D12, B4, 1F3, huC25, Ar1, Ar2, WR1(V), WR1(T), 3-1, 3-8, 3-10, and/or ING1 disclosed herein), preferably a purified polypeptide, a polypeptide coupled to an appropriate carrier (e.g., GST, keyhole limpet hemanocyanin, etc.), or a polypeptide incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the polypeptide of interest. When appropriately high titers of antibody to the immunogen are obtained, blood is collected from the animal and antisera are prepared. Further fractionation of the antisera to enrich for antibodies reactive to the BoNT/A polypeptide is performed where desired (see, e.g., Coligan (1991) *Current Protocols in Immunology* Wiley/Greene, N.Y.; and Harlow and Lane (1989) *Antibodies: A Laboratory Manual* Cold Spring Harbor Press, NY).

Antibodies that specifically bind to the neutralizing epitopes described herein can be selected from polyclonal sera using the selection techniques described herein.

2) Monoclonal Antibody Production.

In some instances, it is desirable to prepare monoclonal antibodies from various mammalian hosts, such as mice, rodents, primates, humans, etc. Descriptions of techniques for preparing such monoclonal antibodies are found in, e.g., Stites et al. (eds.) *Basic and Clinical Immunology* (4th ed.) Lange Medical Publications, Los Altos, Calif., and references cited therein; Harlow and Lane, supra; Goding (1986) *Monoclonal Antibodies: Principles and Practice* (2d ed.) Academic Press, New York, N.Y.; and Kohler and Milstein (1975) *Nature* 256: 495-497.

Summarized briefly, monoclonal antibody production proceeds by injecting an animal with an immunogen (e.g., BoNT/A, BoNT/A $H_c$, or BoNT/A subsequences including, but not limited to subsequences comprising epitopes specifically bound by antibodies expressed by clones S25, C25, C39, 1C6, 3D12, B4, 1F3, huC25, Ar1, Ar2, WR1(V), WR1 (T), 3-1, 3-8, 3-10, and/or ING1 disclosed herein). The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Alternative methods of immortalization include transformation with Epstein Barr Virus, oncogenes, or retroviruses, or other methods known in the art. Colonies arising from single immortalized cells are screened for production of antibodies of the desired specificity and affinity for the BoNT/A antigen, and yield of the monoclonal antibodies produced by such cells is enhanced by various techniques, including injection into the peritoneal cavity of a vertebrate (preferably mammalian) host. The antibodies of the present invention are used with or without modification, and include chimeric antibodies such as humanized murine antibodies.

II. Modification of BoNT/A Neutralizing Antibodies.

A) Phage Display can be Used to Increase Antibody Affinity.

To create higher affinity antibodies, mutant scFv gene repertories, based on the sequence of a binding scFv (e.g., Table 4, Table 9, or Table 11), are created and expressed on the surface of phage. Display of antibody fragments on the surface of viruses which infect bacteria (bacteriophage or phage) makes it possible to produce human or other mammalian antibodies (e.g. scFvs) with a wide range of affinities and kinetic characteristics. To display antibody fragments on the surface of phage (phage display), an antibody fragment gene is inserted into the gene encoding a phage surface protein (e.g., pIII) and the antibody fragment-pIII fusion protein is expressed on the phage surface (McCafferty et al. (1990) *Nature*, 348: 552-554; Hoogenboom et al. (1991) *Nucleic Acids Res.*, 19: 4133-4137).

Since the antibody fragments on the surface of the phage are functional, those phage bearing antigen binding antibody fragments can be separated from non-binding or lower affinity phage by antigen affinity chromatography (McCafferty et al. (1990) *Nature*, 348: 552-554). Mixtures of phage are allowed to bind to the affinity matrix, non-binding or lower affinity phage are removed by washing, and bound phage are eluted by treatment with acid or alkali. Depending on the affinity of the antibody fragment, enrichment factors of 20 fold-1,000,000 fold are obtained by single round of affinity selection.

By infecting bacteria with the eluted phage or modified variants of the eluted phage as described below, more phage can be grown and subjected to another round of selection. In this way, an enrichment of 1000 fold in one round becomes 1,000,000 fold in two rounds of selection (McCafferty et al. (1990) *Nature*, 348: 552-554). Thus, even when enrichments in each round are low, multiple rounds of affinity selection leads to the isolation of rare phage and the genetic material contained within which encodes the sequence of the binding antibody (Marks et al. (1991) *J. Mol. Biol.*, 222: 581-597). The physical link between genotype and phenotype provided by phage display makes it possible to test every member of an antibody fragment library for binding to antigen, even with libraries as large as 100,000,000 clones. For example, after multiple rounds of selection on antigen, a binding scFv that occurred with a frequency of only 1/30,000,000 clones was recovered (Id.).

1) Chain Shuffling.

One approach for creating mutant scFv gene repertoires involves replacing either the $V_H$ or $V_L$ gene from a binding scFv with a repertoire of $V_H$ or $V_L$ genes (chain shuffling) (Clackson et al. (1991) *Nature*, 352: 624-628). Such gene repertoires contain numerous variable genes derived from the same germline gene as the binding scFv, but with point mutations (Marks et al. (1992) *Bio/Technology*, 10: 779-783). Using light or heavy chain shuffling and phage display, the binding avidities of BoNT/A-neutralizing antibody fragment can be dramatically increased (see, e.g., Marks et al. (1992) *Bio/Technology*, 10: 779-785 in which the affinity of a human scFv antibody fragment which bound the hapten phenyloxazolone (phox) was increased from 300 nM to 15 nM (20 fold)).

Thus, to alter the affinity of BoNT/A-neutralizing antibody a mutant scFv gene repertoire is created containing the $V_H$ gene of a known BoNT/A-neutralizing antibody (see, e.g., Table 4, Table 9, and/or Table 11) and a $V_L$ gene repertoire (light chain shuffling). Alternatively, an scFv gene repertoire is created containing the $V_L$ gene of a known BoNT/A-neutralizing antibody (see Table 4) and a $V_H$ gene repertoire (heavy chain shuffling). The scFv gene repertoire is cloned into a phage display vector (e.g., pHEN-1, Hoogenboom et al. (1991) *Nucleic Acids Res.*, 19: 4133-4137) and after transformation a library of transformants is obtained. Phage were prepared and concentrated and selections are performed as described in the examples.

The antigen concentration is decreased in each round of selection, reaching a concentration less than the desired $K_d$ by the final rounds of selection. This results in the selection of phage on the basis of affinity (Hawkins et al. (1992) *J. Mol. Biol.* 226: 889-896).

2) Increasing the Affinity of BoNT/A-Neutralizing Antibodies by Site Directed Mutagenesis.

The majority of antigen contacting amino acid side chains are located in the complementarity determining regions (CDRs), three in the $V_H$ (CDR1, CDR2, and CDR3) and three in the $V_L$ (CDR1, CDR2, and CDR3) (Chothia et al. (1987) *J. Mol. Biol.*, 196: 901-917; Chothia et al. (1986) *Science*, 233: 755-8; Nhan et al. (1991) *J. Mol. Biol.*, 217: 133-151). These residues contribute the majority of binding energetics responsible for antibody affinity for antigen. In other molecules, mutating amino acids that contact ligand has been shown to be an effective means of increasing the affinity of one protein molecule for its binding partner (Lowman et al. (1993) *J. Mol. Biol.*, 234: 564-578; Wells (1990) *Biochemistry*, 29: 8509-8516). Thus mutation (randomization) of the CDRs and screening against BoNT/A, BoNT/A $H_C$ or the epiotpes thereof identified herein, may be used to generate BoNT/A-neutralizing antibodies having improved binding affinity.

In a preferred embodiment, each CDR is randomized in a separate library, using, for example, S25 as a template ($K_d$=7.3×10$^{-8}$ M). To simplify affinity measurement, S25, or other lower affinity BoNT/A-neutralizing antibodies, are used as a template, rather than a higher affinity scFv. The CDR sequences of the highest affinity mutants from each CDR library are combined to obtain an additive increase in affinity. A similar approach has been used to increase the affinity of human growth hormone (hGH) for the growth hormone receptor over 1500 fold from 3.4×10$^{-10}$ to 9.0×10$^{-13}$ M (Lowman et al. (1993) *J. Mol. Biol.*, 234: 564-578).

To increase the affinity of BoNT/A-neutralizing antibodies, amino acid residues located in one or more CDRs (e.g. 9 amino acid residues located in $V_L$ CDR3) are partially randomized by synthesizing a 'doped' oligonucleotide in which the wild type nucleotide occurred with a frequency of, e.g. 49%. The oligonucleotide is used to amplify the remainder of the BoNT/A-neutralizing scFv gene(s) using PCR.

For example in one embodiment, to create a library in which $V_H$ CDR3 is randomized an oligonucleotide is synthesized which anneals to the BoNT/A-neutralizing antibody $V_H$ framework 3 and encodes $V_H$ CDR3 and a portion of framework 4. At the four positions to be randomized, the sequence NNS can be used, where N is any of the 4 nucleotides, and S is "C" or "T". The oligonucleotide is used to amplify the BoNT/A-neutralizing antibody $V_H$ gene using PCR, creating a mutant BoNT/A-neutralizing antibody $V_H$ gene repertoire. PCR is used to splice the $V_H$ gene repertoire with the BoNT/A-neutralizing antibody light chain gene, and the resulting scFv gene repertoire cloned into a phage display vector (e.g., pHEN-1 or pCANTAB5E). Ligated vector DNA is used to transform electrocompetent *E. coli* to produce a phage antibody library.

To select higher affinity mutant scFv, each round of selection of the phage antibody libraries is conducted on decreasing amounts of BoNT/A, as described in the Examples. Typically, 96 clones from the third and fourth round of selection are screened for binding to the BoNT/A antigen by ELISA on 96 well plates. scFv from twenty to forty ELISA positive clones are expressed, e.g. in 10 ml cultures, the periplasm harvested, and the scFv $k_{off}$ determined by BIACORE™. Clones with the slowest $k_{off}$ are sequenced, and each unique scFv subcloned into an appropriate vector (e.g., pUC119 mycHis). The scFv are expressed in culture, and purified as described herein. Affinities of purified scFv are determined by BIACORE™.

3) Creation of BoNT/A-Neutralizing (scFv')2 Homodimers.

To create BoNT/A-neutralizing (scFv')$_2$ antibodies, two BoNT/A-neutralizing scFvs are joined, either through a linker (e.g., a carbon linker, a peptide, etc.) or through a disulfide bond between, for example, two cysteins. Thus, for example, to create disulfide linked BoNT/A-neutralizing scFv, a cysteine residue can be introduced by site directed mutagenesis between the myc tag and hexahistidine tag at the carboxy-terminus of the BoNT/A-neutralizing scFv. Introduction of the correct sequence is verified by DNA sequencing. In a preferred embodiment, the construct is in pUC119, so that the pelB leader directs expressed scFv to the periplasm and cloning sites (Ncol and NotI) exist to introduce BoNT/A-neutralizing mutant scFv. Expressed scFv has the myc tag at the C-terminus, followed by two glycines, a cysteine, and then 6 histidines to facilitate purification by IMAC. After disulfide bond formation between the two cysteine residues, the two scFv are separated from each other by 26 amino acids (two 11 amino acid myc tags and 4 glycines). An scFv was expressed from this construct, purified by IMAC may predominantly comprise monomeric scFv. To produce (scFv')$_2$ dimers, the cysteine is reduced by incubation with 1 mM beta-mercaptoethanol, and half of the scFv blocked by the addition of DTNB. Blocked and unblocked scFvs are incubated together to form (scFv')$_2$ and the resulting material can optionally be analyzed by gel filtration. The affinity of the BoNT/A-neutralizing scFv' monomer and (scFv')$_2$ dimer can optionally be determined by BIACORE™ as described herein.

In a particularly preferred embodiment, the (scFv')$_2$ dimer is created by joining the scFv fragments through a linker, more preferably through a peptide linker. This can be accomplished by a wide variety of means well known to those of skill in the art. For example, one preferred approach is described by Holliger et al. (1993) *Proc. Natl. Acad. Sci. USA*, 90: 6444-6448 (see also WO 94/13804).

Typically, linkers are introduced by PCR cloning. For example, synthetic oligonucleotides encoding the 5 amino acid linker (G$_4$S) can be used to PCR amplify the BoNT/A-neutralizing antibody $V_H$ and $V_L$ genes which are then spliced together to create the BoNT/A-neutralizing diabody gene. The gene is then cloned into an appropriate vector, expressed, and purified according to standard methods well known to those of skill in the art.

4) Preparation of BoNT/A-neutralizing (scFv)$_2$, Fab, and (Fab')$_2$ Molecules.

BoNT/A-neutralizing antibodies such as BoNT/A-neutralizing scFv, or variant(s) with higher affinity, are suitable templates for creating size and valency variants. For example, a BoNT/A-neutralizing (scFv')$_2$ is created from the parent scFv as described above. An scFv gene can be excised using appropriate restriction enzymes and cloned into another vector as described herein.

In one embodiment, expressed scFv has a myc tag at the C-terminus, followed by two glycines, a cysteine, and six histidines to facilitate purification. After disulfide bond formation between the two cystine residues, the two scFv should be separated from each other by 26 amino acids (e.g., two eleven amino acid myc tags and four glycines). scFv is expressed from this construct and purified.

To produce (scFv')$_2$ dimers, the cysteine is reduced by incubation with 1 mM β-mercaptoethanol, and half of the scFv blocked by the addition of DTNB. Blocked and unblocked scFv are incubated together to form (scFv')$_2$, which is purified. As higher affinity scFv are isolated, their genes are similarly used to construct (scFv')$_2$.

BoNT/A-neutralizing Fab are expressed in *E. coli* using an expression vector similar to the one described by Better et. al. (1988) *Science*, 240: 1041-1043. To create a BoNT/A-neutralizing Fab, the $V_H$ and $V_L$ genes are amplified from the scFv using PCR. The $V_H$ gene is cloned into an expression vector (e.g., a PUC119 based bacterial expression vector) that provides an IgG $C_H1$ domain downstream from, and in frame with, the $V_H$ gene. The vector also contains the lac promoter, a pelb leader sequence to direct expressed $V_H$-$C_H1$ domain into the periplasm, a gene 3 leader sequence to direct expressed light chain into the periplasm, and cloning sites for the light chain gene. Clones containing the correct VH gene are identified, e.g., by PCR fingerprinting. The $V_L$ gene is spliced to the $C_L$ gene using PCR and cloned into the vector containing the $V_H C_H 1$ gene.

B) Selection of Neutralizing Antibodies.

In preferred embodiments, selection of BoNT/A-neutralizing antibodies (whether produced by phage display, immunization methods, hybridoma technology, etc.) involves screening the resulting antibodies for specific binding to an appropriate antigen. In the instant case, the preferred antigen is BoNT/A $H_C$, a C-terminal domain of BoNT heavy chain (binding domain). In particularly preferred embodiments the neutralizing antibodies are selected for specific binding of an epitope recognized by an antibody expressed by one or more of clones S25, C25, C39, 1C6, 3D12, B4, 1F3, huC25, Ar1, Ar2, WR1(V), WR1(T), 3-1, 3-8, 3-10, and/or ING1.

Selection can by any of a number of methods well known to those of skill in the art. In a preferred embodiment, selection is by immunochromatography (e.g., using immunotubes, Maxisorp, Nunc) against BoNT/A or BoNT/A $H_C$. In another preferred embodiment, selection is against BoNT/A HC in surface plasmon resonance system (e.g. BIACORE™, Pharmacia) either alone or in combination with an antibody that binds to an epitope specifically bound by an antibody expressed by one or more of clones S25, C25, C39, 1-C6, 3D12, B4, 1F3, huC25, Ar1, Ar2, WR1(V), WR1(T), 3-1, 3-8, 3-10, and/or ING1.

Analysis of binding can be simplified by including an amber codon between the antibody fragment gene and gene III. This makes it possible to easily switch between displayed and soluble antibody fragments simply by changing the host bacterial strain. When phage are grown in a supE suppresser strain of E. coli, the amber stop codon between the antibody gene and gene III is read as glutamine and the antibody fragment is displayed on the surface of the phage. When eluted phage are used to infect a non-suppressor strain, the amber codon is read as a stop codon and soluble antibody is secreted from the bacteria into the periplasm and culture media (Hoogenboom et al. (1991) Nucleic Acids Res., 19: 4133-4137). Binding of soluble scFv to antigen can be detected, e.g., by ELISA using a murine IgG monoclonal antibody (e.g., 9E10) which recognizes a C-terminal myc peptide tag on the scFv (Evan et al. (1985) Mol. Cell. Biol., 5: 3610-3616; Munro et al. (1986) Cell, 46: 291-300), e.g., followed by incubation with polyclonal anti-mouse Fc conjugated to a detectable label (e.g., horseradish peroxidase).

As indicated above, purification of the BoNT/A-neutralizing antibody can be facilitated by cloning of the scFv gene into an expression vector (e.g., expression vector pUC119mycHIS) that results in the addition of the myc peptide tag followed by a hexa-histidine tag at the C-terminal end of the scFv. The vector also preferably encodes the pectate lyase leader sequence that directs expression of the scFv into the bacterial periplasm where the leader sequence is cleaved. This makes it possible to harvest native properly folded scFv directly from the bacterial periplasm. The BoNT/A-neutralizing antibody is then expressed and purified from the bacterial supernatant using immobilized metal affinity chromatography.

C) Measurement of BoNT/A-Neutralizing Antibody Affinity for BoNT/A.

As explained above, selection for increased avidity involves measuring the affinity of a BoNT/A-neutralizing antibody (or a modified BoNT/A-neutralizing antibody) for BoNT/A (or a BoNT/A fragment (e.g., $H_c$), or an epitope on BoNT/A, etc.). Methods of making such measurements are described in detail in the examples provided herein. Briefly, for example, the $K_d$ of a BoNT/A-neutralizing antibody and the kinetics of binding to BoNT/A are determined in a BIACORE™, a biosensor based on surface plasmon resonance. For this technique, antigen is coupled to a derivatized sensor chip capable of detecting changes in mass. When antibody is passed over the sensor chip, antibody binds to the antigen resulting in an increase in mass that is quantifiable. Measurement of the rate of association as a function of antibody concentration can be used to calculate the association rate constant ($k_{on}$). After the association phase, buffer is passed over the chip and the rate of dissociation of antibody ($k_{off}$) determined. K. is typically measured in the range $1.0\times10^2$ to $5.0\times10^6$ and $k_{off}$ in the range $1.0\times10^{-1}$ to $1.0\times10^{-6}$. The equilibrium constant $K_d$ is then calculated as $k_{off}/k_{on}$ and thus is typically measured in the range $10^{-5}$ to $10^{-12}$. Affinities measured in this manner correlate well with affinities measured in solution by fluorescence quench titration.

Phage display and selection generally results in the selection of higher affinity mutant scFvs (Marks et al. (1992) Bio/Technology, 10: 779-783; Hawkins et al. (1992) J. Mol. Biol. 226: 889-896; Riechmann et al. (1993) Biochemistry, 32: 8848-8855; Clackson et al. (1991) Nature, 352: 624-628), but probably does not result in the separation of mutants with less than a 6 fold difference in affinity (Riechmann et al. (1993) Biochemistry, 32: 8848-8855). Thus a rapid method is needed to estimate the relative affinities of mutant scFvs isolated after selection. Since increased affinity results primarily from a reduction in the $k_{off}$, measurement of $k_{off}$ should identify higher affinity scFv. $k_{off}$ can be measured in the BIACORE™ on unpurified scFv in bacterial periplasm, since expression levels are high enough to give an adequate binding signal and $k_{off}$ is independent of concentration. The value of $k_{off}$ for periplasmic and purified scFv is typically in close agreement.

III. Human or Humanized (Chimeric) Antibody Production.

As indicated above, the BoNT/A-neutralizing antibodies of this invention can be administered to an organism (e.g., a human patient) for therapeutic purposes (e.g., the treatment of botulism). Antibodies administered to an organism other than the species in which they are raised can be immunogenic. Thus, for example, murine antibodies repeatedly administered to a human often induce an immunologic response against the antibody (e.g., the human anti-mouse antibody (HAMA) response). While this is typically not a problem for the use of non-human antibodies of this invention as they are typically not utilized repeatedly, the immunogenic properties of the antibody are reduced by altering portions, or all, of the antibody into characteristically human sequences thereby producing chimeric or human antibodies, respectively.

A) Humanized (Chimeric) Antibodies.

Humanized (chimeric) antibodies are immunoglobulin molecules comprising a human and non-human portion. More specifically, the antigen combining region (or variable region) of a humanized chimeric antibody is derived from a non-human source (e.g., murine) and the constant region of the chimeric antibody (which confers biological effector function to the immunoglobulin) is derived from a human source. The humanized chimeric antibody should have the antigen binding specificity of the non-human antibody molecule and the effector function conferred by the human antibody molecule. A large number of methods of generating chimeric antibodies are well known to those of skill in the art (see, e.g., U.S. Pat. Nos. 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431, and 4,975,369).

In general, the procedures used to produce chimeric antibodies consist of the following steps (the order of some steps may be interchanged): (a) identifying and cloning the correct gene segment encoding the antigen binding portion of the antibody molecule; this gene segment (known as the VDJ, variable, diversity and joining regions for heavy chains or VJ, variable, joining regions for light chains (or simply as the V or variable region) may be in either the cDNA or genomic form; (b) cloning the gene segments encoding the constant region or desired part thereof; (c) ligating the variable region to the constant region so that the complete chimeric antibody is encoded in a transcribable and translatable form; (d) ligating this construct into a vector containing a selectable marker and gene control regions such as promoters, enhancers and poly (A) addition signals; (e) amplifying this construct in a host cell (e.g., bacteria); (f) introducing the DNA into eukaryotic cells (transfection) most often mammalian lymphocytes; and culturing the host cell under conditions suitable for expression of the chimeric antibody.

Antibodies of several distinct antigen binding specificities have been manipulated by these protocols to produce chimeric proteins (e.g., anti-TNP: Boulianne et al. (1984) *Nature,* 312: 643; and anti-tumor antigens: Sahagan et al. (1986) *J. Immunol.,* 137: 1066). Likewise several different effector functions have been achieved by linking new sequences to those encoding the antigen binding region. Some of these include enzymes (Neuberger et al. (1984) *Nature* 312: 604), immunoglobulin constant regions from another species and constant regions of another immunoglobulin chain (Sharon et al. (1984) *Nature* 309: 364; Tan et al., (1985) *J. Immunol.* 135: 3565-3567).

In one preferred embodiment, a recombinant DNA vector is used to transfect a cell line that produces a BoNT/A-neutralizing antibody. The novel recombinant DNA vector contains a "replacement gene" to replace all or a portion of the gene encoding the immunoglobulin constant region in the cell line (e.g., a replacement gene may encode all or a portion of a constant region of a human immunoglobulin, a specific immunoglobulin class, or an enzyme, a toxin, a biologically active peptide, a growth factor, inhibitor, or a linker peptide to facilitate conjugation to a drug, toxin, or other molecule, etc.), and a "target sequence" which allows for targeted homologous recombination with immunoglobulin sequences within the antibody producing cell.

In another embodiment, a recombinant DNA vector is used to transfect a cell line that produces an antibody having a desired effector function, (e.g., a constant region of a human immunoglobulin) in which case, the replacement gene contained in the recombinant vector may encode all or a portion of a region of an BoNT/A-neutralizing antibody and the target sequence contained in the recombinant vector allows for homologous recombination and targeted gene modification within the antibody producing cell. In either embodiment, when only a portion of the variable or constant region is replaced, the resulting chimeric antibody may define the same antigen and/or have the same effector function yet be altered or improved so that the chimeric antibody may demonstrate a greater antigen specificity, greater affinity binding constant, increased effector function, or increased secretion and production by the transfected antibody producing cell line, etc.

Regardless of the embodiment practiced, the processes of selection for integrated DNA (via a selectable marker), screening for chimeric antibody production, and cell cloning, can be used to obtain a clone of cells producing the chimeric antibody.

Thus, a piece of DNA which encodes a modification for a monoclonal antibody can be targeted directly to the site of the expressed immunoglobulin gene within a B-cell or hybridoma cell line. DNA constructs for any particular modification may be used to alter the protein product of any monoclonal cell line or hybridoma. Such a procedure circumvents the costly and time consuming task of cloning both heavy and light chain variable region genes from each B-cell clone expressing a useful antigen specificity. In addition to circumventing the process of cloning variable region genes, the level of expression of chimeric antibody should be higher when the gene is at its natural chromosomal location rather than at a random position. Detailed methods for preparation of chimeric (humanized) antibodies can be found in U.S. Pat. No. 5,482,856.

B) Human Antibodies.

In another embodiment, this invention provides for fully human anti-BoNT/A-neutralizing antibodies. Human antibodies consist entirely of characteristically human polypeptide sequences. The human BoNT/A-neutralizing antibodies of this invention can be produced in using a wide variety of methods (see, e.g., Larrick et al., U.S. Pat. No. 5,001,065, for review).

In one preferred embodiment, fully human antibodies are produced using phage display methods as described herein. However, instead of utilizing a murine gene library, a human gene library is used. Methods of producing fully human gene libraries are well known to those of skill in the art (see, e.g., Vaughn et al. (1996) *Nature Biotechnology,* 14(3): 309-314, Marks et al. (1991) *J. Mol. Biol.,* 222: 581-597, and PCT/US96/10287).

In another preferred embodiment, the human BoNT/A-neutralizing antibodies of the present invention are usually initially in trioma cells. Genes encoding the antibodies are then cloned and expressed in other cells, particularly, nonhuman mammalian cells.

The general approach for producing human antibodies by trioma technology has been described by Ostberg et al. (1983) *Hybridoma* 2: 361-367, Ostberg, U.S. Pat. No. 4,634,664, and Engelman et al., U.S. Pat. No. 4,634,666. The antibody-producing cell lines obtained by this method are called triomas because they are descended from three cells; two human and one mouse. Triomas have been found to produce antibody more stably than ordinary hybridomas made from human cells.

Preparation of trioma cells requires an initial fusion of a mouse myeloma cell line with unimmunized human peripheral B lymphocytes. This fusion generates a xenogenic hybrid cell containing both human and mouse chromosomes (see, Engelman, supra.). Xenogenic cells that have lost the capacity to secrete antibodies are selected. Preferably, a xenogenic cell is selected that is resistant to 8-azaguanine. Such cells are unable to propagate on hypoxanthine-aminopterin-thymidine (HAT) or azaserine-hypoxanthine (AH) media.

The capacity to secrete antibodies is conferred by a further fusion between the xenogenic cell and B-lymphocytes immunized against an BoNT/A polypeptide (e.g., BoNT/A, BoNT/A $H_C$, or BoNT/A subsequences including, but not limited to subsequences comprising epitopes specifically bound by antibodies expressed by clones S25, C25, C39, 1-C6, and 1F3 disclosed herein). The B-lymphocytes are obtained from the spleen, blood or lymph nodes of human donor. If antibodies against a specific antigen or epitope are desired, it is preferable to use that antigen or epitope thereof as the immunogen rather than the entire polypeptide. Alternatively, B-lymphocytes are obtained from an unimmunized individual and stimulated with a BoNT/A polypeptide, or a epitope thereof, in vitro. In a further variation, B-lymphocytes are obtained from an infected, or otherwise immunized individual, and then hyperimmunized by exposure to a BoNT/A polypeptide for about seven to fourteen days, in vitro.

The immunized B-lymphocytes prepared by one of the above procedures are fused with a xenogenic hybrid cell by well known methods. For example, the cells are treated with 40-50% polyethylene glycol of MW 1000-4000, at about 37° C. for about 5-10 min. Cells are separated from the fusion mixture and propagated in media selective for the desired hybrids. When the xenogenic hybrid cell is resistant to 8-azaguanine, immortalized trioma cells are conveniently selected by successive passage of cells on HAT or AH medium. Other selective procedures are, of course, possible depending on the nature of the cells used in fusion. Clones secreting antibodies having the required binding specificity are identified by assaying the trioma culture medium for the ability to bind to the BoNT/A polypeptide or an epitope thereof. Triomas producing human antibodies having the desired specificity are subcloned by the limiting dilution technique and grown in vitro in culture medium, or are injected into selected host animals and grown in vivo.

The trioma cell lines obtained are then tested for the ability to bind a BoNT/A polypeptide or an epitope thereof. Antibodies are separated from the resulting culture medium or body fluids by conventional antibody-fractionation procedures, such as ammonium sulfate precipitation, DEAE cellulose chromatography and affinity chromatography.

Although triomas are genetically stable they do not produce antibodies at very high levels. Expression levels can be increased by cloning antibody genes from the trioma into one or more expression vectors, and transforming the vector into a cell line such as the cell lines typically used for expression of recombinant or humanized immunoglobulins. As well as increasing yield of antibody, this strategy offers the additional advantage that immunoglobulins are obtained from a cell line that does not have a human component, and does not therefore need to be subjected to the especially extensive viral screening required for human cell lines.

The genes encoding the heavy and light chains of immunoglobulins secreted by trioma cell lines are cloned according to methods, including but not limited to, the polymerase chain reaction (PCR), known in the art (see, e.g., Sambrook et al., *Molecular Cloning: A Laboratory Manual*, 2nd ed., Cold Spring Harbor, N.Y., 1989; Berger & Kimmel, *Methods in Enzymology, Vol.* 152: *Guide to Molecular Cloning Techniques*, Academic Press, Inc., San Diego, Calif., 1987; Co et al. (1992) *J. Immunol.*, 148: 1149). For example, genes encoding heavy and light chains are cloned from a trioma's genomic DNA or cDNA produced by reverse transcription of the trioma's RNA. Cloning is accomplished by conventional techniques including the use of PCR primers that hybridize to the sequences flanking or overlapping the genes, or segments of genes, to be cloned.

Typically, recombinant constructs comprise DNA segments encoding a complete human immunoglobulin heavy chain and/or a complete human immunoglobulin light chain of an immunoglobulin expressed by a trioma cell line. Alternatively, DNA segments encoding only a portion of the primary antibody genes are produced, which portions possess binding and/or effector activities. Other recombinant constructs contain segments of trioma cell line immunoglobulin genes fused to segments of other immunoglobulin genes, particularly segments of other human constant region sequences (heavy and/or light chain). Human constant region sequences can be selected from various reference sources, including but not limited to those listed in Kabat et al. (1987) *Sequences of Proteins of Immunological Interest*, U.S. Department of Health and Human Services.

In addition to the DNA segments encoding BoNT/A-neutralizing immunoglobulins or fragments thereof, other substantially homologous modified immunoglobulins can be readily designed and manufactured utilizing various recombinant DNA techniques known to those skilled in the art such as site-directed mutagenesis (see Gillman & Smith (1979) *Gene*, 8: 81-97; Roberts et al. (1987) *Nature* 328: 731-734). Such modified segments will usually retain antigen binding capacity and/or effector function. Moreover, the modified segments are usually not so far changed from the original trioma genomic sequences to prevent hybridization to these sequences under stringent conditions. Because, like many genes, immunoglobulin genes contain separate functional regions, each having one or more distinct biological activities, the genes may be fused to functional regions from other genes to produce fusion proteins (e.g., immunotoxins) having novel properties or novel combinations of properties.

The genomic sequences can be cloned and expressed according to standard methods as described herein.

Other approaches to antibody production include in vitro immunization of human blood. In this approach, human blood lymphocytes capable of producing human antibodies are produced. Human peripheral blood is collected from the patient and is treated to recover mononuclear cells. The suppressor T-cells then are removed and remaining cells are suspended in a tissue culture medium to which is added the antigen and autologous serum and, preferably, a nonspecific lymphocyte activator. The cells then are incubated for a period of time so that they produce the specific antibody desired. The cells then can be fused to human myeloma cells to immortalize the cell line, thereby to permit continuous production of antibody (see U.S. Pat. No. 4,716,111).

In another approach, mouse-human hybridomas which produces human BoNT/A-neutralizing antibodies are prepared (see, e.g., U.S. Pat. No. 5,506,132). Other approaches include immunization of murines transformed to express human immunoglobulin genes, and phage display screening (Vaughan et al. supra.).

IV. Assaying for Cross-Reactivity at a Neutralizing Epitope.

In a preferred embodiment, the antibodies of this invention specifically bind to one or more epitopes recognized by antibodies expressed by clones S25, C25, C39, 1-C6, or 1F3 (for convenience referred to herein as S25, C25, C39, 1-C6, or 1F3 antibodies respectively). In other words, particularly preferred antibodies are cross-reactive with one of more of these antibodies. Means of assaying for cross-reactivity are well known to those of skill in the art (see, e.g., Dowbenko et al. (1988) *J. Virol.* 62: 4703-4711).

This can be ascertained by providing an isolated BoNT/A polypeptide (preferably BoNT/A $H_C$) attached to a solid support and assaying the ability of a test antibody to compete with S25, C25, C39, 1-C6, or 1F3 antibodies for BoNT/A binding. Thus, immunoassays in a competitive binding format are preferably used for crossreactivity determinations. For example, in one embodiment, the BoNT/A $H_C$ polypeptide is immobilized to a solid support. Antibodies to be tested (e.g. generated by selection from a phage-display library) added to the assay compete with S25, C25, C39, 1C6, or 1F3 antibodies binding to the immobilized BoNT/A polypeptide. The ability of test antibodies to compete with the binding of the S25, C25, C39, 1-C6, or 1F3 antibodies to the immobilized protein are compared. The percent crossreactivity above proteins is then calculated, using standard calculations.

If the test antibody competes with one or more of the S25, C25, C39, 1-C6, or 1F3 antibodies and has a binding affinity comparable to or greater than about $1\times10^{-8}$ M with the same target then the test antibody will prove to be a BoNT/A neutralizing antibody.

In a particularly preferred embodiment, cross-reactivity is performed by using surface plasmon resonance in a BIA-CORE™. In a BIACORE™ flow cell, the BoNT/A $H_E$ is coupled to a sensor chip (e.g. CM5) as described in the examples. With a flow rate of 5 μl/min, a titration of 100 nM to 1 μM antibody is injected over the flow cell surface for about 5 minutes to determine an antibody concentration that results in near saturation of the surface. Epitope mapping or cross-reactivity is then evaluated using pairs of antibodies at concentrations resulting in near saturation and at least 100 RU of antibody bound. The amount of antibody bound is determined for each member of a pair, and then the two antibodies are mixed together to give a final concentration equal to the concentration used for measurements of the individual antibodies. Antibodies recognizing different epitopes show an essentially additive increase in the RU bound when injected together, while antibodies recognizing identical epitopes show only a minimal increase in RU (see the examples). In a particularly preferred embodiment, antibodies are said to be cross-reactive if, when "injected" together they show an essentially additive increase (preferably an increase by at least a factor of about 1.4, more preferably an increase by at least a factor of about 1.6, and most preferably an increase by at least a factor of about 1.8 or 2.

Cross-reactivity at the S25, C25, C39, 1-C6, or 1F3 epitopes can ascertained by a number of other standard techniques (see, e.g., Geysen et al (1987) *J. Immunol. Meth.* 102, 259-274). This technique involves the synthesis of large numbers of overlapping BoNT/A $H_C$ peptides. The synthesized peptides are then screened against one or more of the S25, C25, C39, 1-C6, or 1F3 antibodies and the characteristic epitopes specifically bound by these antibodies can be identified by binding specificity and affinity. The epitopes thus identified can be conveniently used for competitive assays as described herein to identify cross-reacting antibodies.

The peptides for S25, C25, C39, 1C6, or 1F3 epitope mapping can be conveniently prepared using "Multipin" peptide synthesis techniques (see, e.g., Geysen et al (1987) Science, 235: 1184-1190). Using the known sequence of BoNT/A $H_C$ (see, e.g., Atassi et al. (1996) *J. Prot. Chem.*, 7: 691-700 and references cited therein), overlapping BoNT/A $H_C$ polypeptide sequences can be synthesized individually in a sequential manner on plastic pins in an array of one or more 96-well microtest plate(s).

The procedure for epitope mapping using this multipin peptide system is described in U.S. Pat. No. 5,739,306. Briefly, the pins are first treated with a pre-coat buffer containing 2% bovine serum albumin and 0.1% Tween 20 in PBS for 1 hour at room temperature. Then the pins are then inserted into the individual wells of 96-well microtest plate containing antibody S25, C25, C39, 1C6, or 1F3 in the pre-coat buffer, e.g. at 2 mu g/ml. The incubation is preferably for about 1 hour at room temperature. The pins are washed in PBST (e.g., 3 rinses for every 10 minutes), and then incubated in the wells of a 96-well microtest plate containing 100 mu 1 of HRP-conjugated goat anti-mouse IgG (Fc) (Jackson ImmunoResearch Laboratories) at a 1:4,000 dilution for 1 hour at room temperature. After the pins are washed as before, the pins are put into wells containing peroxidase substrate solution of diammonium 2,2'-azino-bis[3-ethylbenzthiazoline-b-sulfonate] (ABTS) and $H_2O_2$ (Kirkegaard & Perry Laboratories Inc., Gaithersburg, Md.) for 30 minutes at room temperature for color reaction. The plate is read at 405 nm by a plate reader (e.g., BioTek ELISA plate reader) against a background absorption wavelength of 492 nm. Wells showing color development indicated reactivity of the BoNT/A $H_C$ peptides in such wells with S25, C25, C39, 1-C6, or 1F3 antibodies.

V. Assaying for Neutralizing Activity of Anti-BoNT/A Antibodies.

Preferred antibodies of this invention act to neutralize (reduce or eliminate) the toxicity of botulinum neurotoxin type A. Neutralization can be evaluated in vivo or in vitro. In vivo neutralization measurements simply involve measuring changes in the lethality (e.g. $LD_{50}$ or other standard metric) due to a BoNT/A type A neurotoxin administration due to the presence of one or more antibodies being tested for neutralizing activity. The neurotoxin can be directly administered to the test organism (e.g. mouse) or the organism can harbor a botulism infection (e.g., be infected with *Clostridium botulinum*). The antibody can be administered before, during, or after the injection of BoNT/A neurotoxin or infection of the test animal. A decrease in the rate of progression, or mortality rate indicates that the antibody(s) have neutralizing activity.

A preferred in vitro assay for neutralizing activity uses a hemidiaphragm preparation (Deshpande et al. (1995) *Toxicon*, 33: 551-557). Briefly, left and right phrenic nerve hemidiaphragm preparations are suspended in physiological solution and maintained at a constant temperature (e.g. 36° C.). The phrenic nerves are stimulated supramaximally (e.g. at 0.05 Hz with square waves of 0.2 ms duration). Isometric twitch tension is measured with a force displacement transducer (e.g., GrassModel FT03) connected to a chart recorder.

Purified antibodies are incubated with purified BoNT/A for 30 min at room temperature and then added to the tissue bath, resulting in a final antibody concentration of about $2.0\times10^{-8}$ M and a final BoNT/A concentration of about $2.0\times10^{-11}$ M. For each antibody studied, time to 50% twitch tension reduction is determined (e.g., three times for BoNT/A alone and three times for antibody plus BoNT/A). Differences between times to a given (arbitrary) percentage (e.g. 50%) twitch reduction are determined by standard statistical analyses (e.g. two-tailed t test) at standard levels of significance (e.g., a P value of <0.05 considered significant).

VI. Diagnostic Assays.

As explained above, the BoNT/A-neutralizing antibodies may be used for the in vivo or in vitro detection of BoNT/A toxin and thus, are useful in the diagnosis (e.g. confirmatory diagnosis) of botulism. The detection and/or quantification of BoNT/A in a biological sample obtained from an organism is indicative of a *Clostridium botulinum* infection of that organism.

The BoNT/A antigen may be quantified in a biological sample derived from a patient such as a cell, or a tissue sample derived from a patient. As used herein, a biological sample is a sample of biological tissue or fluid that contains a BoNT/A concentration that may be correlated with and indicative of a *Clostridium botulinum* infection. Preferred biological samples include blood, urine, saliva, and tissue biopsies.

Although the sample is typically taken from a human patient, the assays can be used to detect BoNT/A antigen in cells from mammals in general, such as dogs, cats, sheep, cattle and pigs, and most particularly primates such as humans, chimpanzees, gorillas, macaques, and baboons, and rodents such as mice, rats, and guinea pigs.

Tissue or fluid samples are isolated from a patient according to standard methods well known to those of skill in the art, most typically by biopsy or venipuncture. The sample is optionally pretreated as necessary by dilution in an appropriate buffer solution or concentrated, if desired. Any of a number of standard aqueous buffer solutions, employing one of a variety of buffers, such as phosphate, Tris, or the like, at physiological pH can be used.

A) Immunological Binding Assays

The BoNT/A polypeptide is preferably detected in an immunoassay utilizing a BoNT/A-neutralizing antibody as a capture agent that specifically binds to the BoNT/A polypeptide.

As used herein, an immunoassay is an assay that utilizes an antibody (e.g. a BoNT/A-neutralizing antibody) to specifically bind an analyte (e.g., BoNT/A). The immunoassay is characterized by the use of specific antibody binding to a BoNT/A-neutralizing antibody as opposed to other physical or chemical properties to isolate, target, and quantify the BoNT/A analyte.

The BoNT/A marker may be detected and quantified using any of a number of well recognized immunological binding assays. (See for example, U.S. Pat. Nos. 4,366,241; 4,376,110; 4,517,288; and 4,837,168, which are hereby incorporated by reference.) For a review of the general immunoassays, see also *Methods in Cell Biology Volume 37: Antibodies in Cell Biology*, Asai, ed. Academic Press, Inc. New York (1993); *Basic and Clinical Immunology* 7th Edition, Stites & Terr, eds. (1991)).

The immunoassays of the present invention are performed in any of several configurations, e.g., those reviewed in Maggio (ed.) (1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier Science Publishers B. V., Amsterdam; Harlow and Lane, supra; Chan (ed.) (1987) *Immunoassay: A Practical Guide* Academic Press, Orlando, Fla.; Price and Newman (eds.) (1991) *Principles and Practice of Immunoassays* Stockton Press, NY; and Ngo (ed.) (1988) *Non isotopic Immunoassays* Plenum Press, NY.

Immunoassays often utilize a labeling agent to specifically bind to and label the binding complex formed by the capture agent and the analyte (i.e., a BoNT/A-neutralizing antibody/BoNT/A complex). The labeling agent may itself be one of the moieties comprising the antibody/analyte complex. Thus, the labeling agent may be a labeled BoNT/A or a labeled BoNT/A-neutralizing antibody. Alternatively, the labeling agent is optionally a third moiety, such as another antibody, that specifically binds to the BoNT/A-neutralizing antibody, the BoNT/A peptide, the anti-body/polypeptide complex, or to a modified capture group (e.g., biotin) which is covalently linked to BoNT/A or to the BoNT/A-neutralizing antibody.

In one embodiment, the labeling agent is an antibody that specifically binds to the BoNT/A-neutralizing antibody. Such agents are well known to those of skill in the art, and most typically comprise labeled antibodies that specifically bind antibodies of the particular animal species from which the BoNT/A-neutralizing antibody is derived (e.g., an anti-species antibody). Thus, for example, where the capture agent is a human derived BoNT/A-neutralizing antibody, the label agent may be a mouse anti-human IgG, i.e., an antibody specific to the constant region of the human antibody.

Other proteins capable of specifically binding immunoglobulin constant regions, such as streptococcal protein A or protein G are also used as the labeling agent. These proteins are normal constituents of the cell walls of streptococcal bacteria. They exhibit a strong non immunogenic reactivity with immunoglobulin constant regions from a variety of species. See, generally Kronval, et al., (1973) *J. Immunol.*, 111: 1401-1406, and Akerstrom, et al., (1985) *J. Immunol.*, 135: 2589-2542.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays are carried out at ambient temperature, although they can be conducted over a range of temperatures, such as 5° C. to 45° C.

1) Non Competitive Assay Formats.

Immunoassays for detecting BoNT/A are preferably either competitive or noncompetitive. Noncompetitive immunoassays are assays in which the amount of captured analyte (in this case, BoNT/A) is directly measured. In one preferred "sandwich" assay, for example, the capture agent (e.g., BoNT/A-neutralizing antibody) is bound directly or indirectly to a solid substrate where it is immobilized. These immobilized BoNT/A-neutralizing antibodies capture BoNT/A present in a test sample (e.g., a blood sample). The BoNT/A thus immobilized is then bound by a labeling agent, such as a BoNT/A-neutralizing antibody bearing a label. Alternatively, the second antibody may lack a label, but it may, in turn, be bound by a labeled third antibody specific to antibodies of the species from which the second antibody is derived. Free labeled antibody is washed away and the remaining bound labeled antibody is detected (e.g., using a gamma detector where the label is radioactive).

2) Competitive Assay Formats.

In competitive assays, the amount of analyte (e.g., BoNT/A) present in the sample is measured indirectly by measuring the amount of an added (exogenous) analyte displaced (or competed away) from a capture agent (e.g., BoNT/A-neutralizing antibody) by the analyte present in the sample. In one competitive assay, a known amount of BoNT/A is added to a test sample with an unquantified amount of BoNT/A, and the sample is contacted with a capture agent, e.g., a BoNT/A-neutralizing antibody that specifically binds BoNT/A. The amount of added BoNT/A that binds to the BoNT/A-neutralizing antibody is inversely proportional to the concentration of BoNT/A present in the test sample.

The BoNT/A-neutralizing antibody can be immobilized on a solid substrate. The amount of BoNT/A bound to the BoNT/A-neutralizing antibody is determined either by measuring the amount of BoNT/A present in an BoNT/A-BoNT/A-neutralizing antibody complex, or alternatively by measuring the amount of remaining uncomplexed BoNT/A.

B) Reduction of Non Specific Binding.

One of skill will appreciate that it is often desirable to reduce non specific binding in immunoassays and during analyte purification. Where the assay involves BoNT/A, BoNT/A-neutralizing antibody, or other capture agent immobilized on a solid substrate, it is desirable to minimize the amount of non specific binding to the substrate. Means of reducing such non specific binding are well known to those of skill in the art. Typically, this involves coating the substrate with a proteinaceous composition. In particular, protein compositions such as bovine serum albumin (BSA), nonfat powdered milk, and gelatin are widely used.

C) Substrates.

As mentioned above, depending upon the assay, various components, including the BoNT/A, BoNT/A-neutralizing or antibodies, are optionally bound to a solid surface. Many methods for immobilizing biomolecules to a variety of solid surfaces are known in the art. For instance, the solid surface may be a membrane (e.g., nitrocellulose), a microtiter dish (e.g., PVC, polypropylene, or polystyrene), a test tube (glass or plastic), a dipstick (e.g. glass, PVC, polypropylene, polystyrene, latex, and the like), a microcentrifuge tube, or a glass, silica, plastic, metallic or polymer bead. The desired component may be covalently bound, or noncovalently attached through nonspecific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which may be employed, include paper, glasses, ceramics, metals, metalloids, semiconductive materials, cements or the like. In addition, substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12-24 carbon atoms) alkyl ammonium salts and the like are also suitable. Where the solid surface is porous, various pore sizes may be employed depending upon the nature of the system.

In preparing the surface, a plurality of different materials may be employed, e.g., as laminates, to obtain various properties. For example, protein coatings, such as gelatin can be used to avoid non specific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. See, for example, *Immobilized Enzymes*, Ichiro Chibata, Halsted Press, New York, 1978, and Cuatrecasas, (1970) *J. Biol. Chem.* 245 3059.

In addition to covalent bonding, various methods for noncovalently binding an assay component can be used. Noncovalent binding is typically nonspecific absorption of a compound to the surface. Typically, the surface is blocked with a second compound to prevent nonspecific binding of labeled assay components. Alternatively, the surface is designed such that it nonspecifically binds one component but does not significantly bind another. For example, a surface bearing a lectin such as concanavalin A will bind a carbohydrate containing compound but not a labeled protein that lacks glycosylation. Various solid surfaces for use in noncovalent attachment of assay components are reviewed in U.S. Pat. Nos. 4,447,576 and 4,254,082.

D) Other Assay Formats

BoNT/A polypeptides or BoNT/A-neutralizing antibodies can also be detected and quantified by any of a number of other means well known to those of skill in the art. These include analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

Western blot analysis and related methods can also be used to detect and quantify the presence of BoNT/A polypeptides in a sample. The technique generally comprises separating sample products by gel electrophoresis on the basis of molecular weight, transferring the separated products to a suitable solid support, (such as a nitrocellulose filter, a nylon filter, or derivatized nylon filter), and incubating the sample with the antibodies that specifically bind either the BoNT/A polypeptide. The antibodies specifically bind to the biological agent of interest on the solid support. These antibodies are directly labeled or alternatively are subsequently detected using labeled antibodies (e.g., labeled sheep anti-human antibodies where the antibody to a marker gene is a human antibody) which specifically bind to the antibody which binds BoNT/A.

Other assay formats include liposome immunoassays (LIAs), which use liposomes designed to bind specific molecules (e.g., antibodies) and release encapsulated reagents or markers. The released chemicals are then detected according to standard techniques (see, Monroe et al., (1986) *Amer. Clin. Prod. Rev.* 5:34-41).

E) Labeling of BoNT/A-Neutralizing Antibodies.

The labeling agent can be, e.g., a monoclonal antibody, a polyclonal antibody, a protein or complex such as those described herein, or a polymer such as an affinity matrix, carbohydrate or lipid. Detection proceeds by any known method, including immunoblotting, western analysis, gel-mobility shift assays, tracking of radioactive or bioluminescent markers, nuclear magnetic resonance, electron paramagnetic resonance, stopped-flow spectroscopy, column chromatography, capillary electrophoresis, or other methods which track a molecule based upon an alteration in size and/or charge. The particular label or detectable group used in the assay is not a critical aspect of the invention. The detectable group can be any material having a detectable physical or chemical property. Such detectable labels have been well-developed in the field of immunoassays and, in general, any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, Texas red, rhodamine, and the like), radiolabels (e.g. $^{3}H$, $^{125}I$, $^{35}S$, $^{14}C$, or $^{32}P$), enzymes (e.g., LacZ, CAT, horse radish peroxidase, alkaline phosphatase and others, commonly used as detectable enzymes, either as marker gene products or in an ELISA), and colorimetric labels such as colloidal gold or colored glass or plastic (e.g. polystyrene, polypropylene, latex, etc.) beads.

The label may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation, and disposal provisions.

Non radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol For a review of various labeling or signal producing systems which may be used, see, U.S. Pat. No. 4,391,904, which is incorporated herein by reference.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like. Similarly, enzymatic labels may be detected by providing appropriate substrates for the enzyme and detecting the resulting reaction product. Finally, simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of BoNT/A peptides. In this case, antigen-coated particles are agglutinated by samples comprising the target antibodies. In this format, none of the components need be labeled and the presence of the target antibody is detected by simple visual inspection.

V. Pharmaceutical Compositions.

The BoNT/A-neutralizing antibodies of this invention are useful for parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the fusion proteins and pharmaceutical compositions of this invention, when administered orally, must be protected from digestion. This is typically accomplished either by complexing the protein with a composition to render it resistant to acidic and enzymatic hydrolysis or by packaging the protein in an appropriately resistant carrier such as a liposome. Means of protecting proteins from digestion are well known in the art.

The pharmaceutical compositions of this invention are particularly useful for parenteral administration, such as intravenous administration or administration into a body cavity or lumen of an organ. The compositions for administration will commonly comprise a solution of the BoNT/A-neutralizing antibody dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of BoNT/A-neutralizing antibody in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Methods for preparing parenterally administrable compositions will be known or apparent to those skilled in the art and are described in more detail in such publications as *Remington's Pharmaceutical Science,* 15th ed., Mack Publishing Company, Easton, Pa. (1980).

The compositions containing the present fusion proteins or a cocktail thereof (i.e., with other proteins) can be administered for therapeutic treatments. In therapeutic applications, Preferred pharmaceutical compositions are administered in a dosage sufficient to neutralize (mitigate or eliminate) BoNT/A toxin (i.e., reduce or eliminate a symptom of BoNT/A poisoning (botulism)). An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the proteins of this invention to effectively treat the patient.

VI. Kits for Diagnosis or Treatment.

In another embodiment, this invention provides for kits for the treatment of botulism or for the detection/confirmation of a *Clostridium botulinum* infection. Kits will typically comprise one or more BoNT/A-neutralizing antibodies of this invention. For diagnostic purposes, the antibody(s) can be labeled. In addition the kits will typically include instructional materials disclosing means of use BoNT/A-neutralizing antibodies in the treatment of symptoms of botulism. The kits may also include additional components to facilitate the particular application for which the kit is designed. Thus, for example, where a kit contains a BoNT/A-neutralizing-antibody antibody is labeled, the kit may additionally contain means of detecting the label (e.g. enzyme substrates for enzymatic labels, filter sets to detect fluorescent labels, appropriate secondary labels such as a sheep anti-human antibodies, or the like). The kits may additionally include buffers and other reagents routinely used for the practice of a particular method. Such kits and appropriate contents are well known to those of skill in the art.

EXAMPLES

The following examples are provided by way of illustration only and not by way of limitation. Those of skill will readily recognize a variety of noncritical parameters that can be changed or modified to yield essentially similar results.

Example 1

Preparation of Botulinum Neurotoxin Neutralizing Antibodies

Materials and Methods

A) Oligonucleotide Design.

Family-specific murine $V_H$ and $V_K$ primers were designed as previously described for human V-gene primers (Marks, et al. (1991) *J. Mol. Biol.* 222:581-597; Marks, et al., *Eur. J. Immunol.* 21:985-991) to amplify full-length rearranged V genes. Briefly, murine $V_H$ and $V_K$ DNA sequences were collected from the Kabat (Kabat, et al. (1991) *Sequences of proteins of immunological interest*, U.S. Department of Health and Human Services, U.S. Government Printing Office, Bethesda, Md.) and GenBank databases, aligned, and classified by family, and family-specific primers were designed to anneal to the first 23 nucleotides comprising framework 1. Similarly, $J_H$ and $J_K$ gene-segment specific primers were designed to anneal to the final 24 nucleotides comprising each of the 4 $J_H$ and 5 $J_K$ gene segments (Kabat, et al. supra.).

B) Vector Construction.

To construct the vector pSYN3, a 1.5 kb stuffer fragment was amplified from pCANTAB5E (Pharmacia Biotech, Milwaukee, Wis.) using PCR with the primers LMB3 (Marks, et al. (1991) *Eur. J. Immunol.* 21:985-991) and E-tagback (5'-ACC ACC GAA TTC TTA TTA ATG GTG ATG ATG GTG GAT GAC CAG CCG GTT CCA GCG G-3', SEQ ID NO: 229). The DNA fragment was digested with SfiI and NotI, gel purified, and ligated into pCANTAB5E digested with SfiI and NotI. Ligated DNA was used to transform *Escherichia coli* TG1 (Gibson (1991) *Studies on the Epstein-Barr virus genome*. University of Cambridge, Cambridge, U. K.), and clones containing the correct insert were identified by DNA sequencing. The resulting vector permits subcloning of phage-displayed scFv as SfiI-NoI or McoI-NotI fragments for secretion into the periplasm of *E. coli* as native scFv with a C-terminal E epitope tag followed by a hexahistidine tag.

C) Immunizations.

For construction of library 1, BALB/c mice (16 to 22 g) were immunized at 0, 2, and 4 weeks with pure BoNT/A $H_c$ (Ophidian Pharmaceuticals, Madison, Wis.). Each animal was given subcutaneously 1 μg of material adsorbed onto alum (Pierce Chemical Co., Rockford, Ill.) in a volume of 0.5 ml. Mice were challenged 2 weeks after the second immunization with 100,000 50% lethal doses of pure BoNT/A and were sacrificed 1 week later.

For construction of library 2, CD-1 mice (16 to 22 g) were immunized at 0, 2, and 4 weeks with pure BoNT/A $H_c$ and were sacrificed two weeks after the third immunization. For both libraries, the spleens were removed immediately after sacrifice and total RNA was extracted by the method of Cathala et al. (1993) *DNA* 2: 329.

D) Library Construction.

First-strand cDNA was synthesized from approximately 10 μg of total RNA as previously described in Marks, et al. (1991) *J. Mol. Biol.* 222:581-597, except that immunoglobulin mRNA was specifically primed with 10 pmol each of oligonucleotides MIgG1 For, MIgG3 For, and $MC_K$ For (Table 1). For construction of library 1, rearranged $V_H$, and $V_K$ genes were amplified from first-strand cDNA by using commercially available $V_H$ and $V_K$ back primers and $J_H$ and $J_K$ forward primers (Recombinant Phage Antibody System; Pharmacia Biotech). For library 2, equimolar mixtures of family-specific $V_H$ and $V_K$ back primers were used in conjunction with equimolar mixtures of $J_H$ or $J_K$ gene-segment-specific forward primers in an attempt to increase library diversity (see "Oligonucleotide design" above). Re-arranged $V_H$ and $V_K$ genes were amplified separately in 50-μl reaction mixtures containing 5 μl of the first-strand cDNA reaction mixture, 20 pmol of an equimolar mixture of the appropriate back primers, 20 pmol of an equimolar mixture of the appropriate forward primers, 250 μm (each) deoxynucleoside triphosphate, 1.5 mm $MgCl_2$, 10 μg of bovine serum albumin/ml, and 1 μl (5 U) of *Thermus aquaticus* (Taq) DNA polymerase (Promega) in the buffer supplied by the manufacturer. The reaction mixture was overlaid with paraffin oil (Sigma) and cycled 30 times (at 95° C. for 1 min, 60° C. for 1 min, and 72° C. for 1 min) Reaction products were gel purified, isolated from the gel by using DEAE membranes, eluted from the membranes with high-salt buffer, ethanol precipitated, and resuspended in 20 μL of water (Sambrook, et al. (1989) *Molecular cloning; a laboratory manual, 2nd ed. Cold Spring Harbor Laboratory*, Cold Spring Harbor, N.Y.).

TABLE 1

Oligonucleotide primers used for PCR of mouse immunoglobulin genes.

| Primer ID | Sequence | Seq I.D. No. |
|---|---|---|
| A. 1st strand cDNA synthesis | | |
| Mouse heavy chain constant region primers | | |
| MIgG1/2 For | 5' CTG GAC AGG GAT CCA GAG TTC CA 3' | 1 |
| MIgG3 For | 5' CTG GAC AGG GCT CCA TAG TTC CA 3' | 2 |
| Mouse constant region primer | | |
| $MC_K$ For | 5' CTC ATT CCT GTT GAA GCT CTT GAC 3' | 3 |
| B. Primary PCR | | |
| Mouse $V_H$ back primers | | |
| VH1 Back | 5' GAG GTG CAG CTT CAG GAG TCA GG 3' | 4 |
| VH2 Back | 5' GAT GTG CAG CTT CAG GAG TCR GG 3' | 5 |
| VH3 Back | 5' CAG GTG CAG CTG AAG SAG TCA GG 3' | 6 |
| VH4/6 Back | 5' GAG GTY CAG CTG CAR CAR TCT GG 3' | 7 |
| VH5/9 Back | 5' CAG GTY CAR CTG CAG CAG YCT GG 3' | 8 |
| VH7 Back | 5' GAR GTG AAG CTG GTG GAR TCT GG 3' | 9 |
| VH8 Back | 5' GAG GTT CAG CTT CAG CAG TCT GG 3' | 10 |
| VH10 Back | 5' GAA GTG CAG CTG KTG GAG WCT GG 3' | 11 |
| VH11 Back | 5' CAG ATC CAG TTG CTG CAG TCT GG 3' | 12 |
| Mouse $V_H$ back primers | | |
| VH1 Back | 5' GAC ATT GTG ATG WCA CAG TCT CC 3' | 13 |
| VH2 Back | 5' GAT GTT KTG ATG ACC CAA ACT CC 3' | 14 |

TABLE 1-continued Oligonucleotide primers used for PCR of mouse immunoglobulin genes.

| Primer ID | Sequence | Seq I.D. No. |
|---|---|---|
| VH3 Back | 5' GAT ATT GTG ATR ACB CAG GCW GC 3' | 15 |
| VH4 Back | 5' GAC ATT GTG CTG ACM CAR TCT CC 3' | 16 |
| VH5 Back | 5' SAA AWT GTK CTC ACC CAG TCT CC 3' | 17 |
| VH6 Back | 5' GAY ATY VWG ATG ACM CAG WCT CC 3' | 18 |
| VH7 Back | 5' CAA ATT GTT CTC ACC CAG TCT CC 3' | 19 |
| VH8 Back | 5' TCA TTA TTG CAG GTG CTT GTG GG 3' | 20 |

Mouse Jh forward primers

| JH1 For | 5' TGA GGA GAC GGT GAC CGT GGT CCC 3' | 21 |
| JH2 For | 5' TGA GGA GAC TGT GAG AGT GGT GCC 3' | 22 |
| JH3 For | 5' TGC AGA GAC AGT GAC CAG AGT CCC 3' | 23 |
| JH4 For | 5' TGA GGA GAC GGT GAC TGA GGT TCC 3' | 24 |

Mouse Jκ forward primers:

| Jκ1 For | 5' TTT GAT TTC CAG CTT GGT GCC TCC 3' | 25 |
| Jκ2 For | 5' TTT TAT TTC CAG CTT GGT CCC CCC 3' | 26 |
| Jκ3 For | 5' TTT TAT TTC CAG TCT GGT CCC ATC 3' | 27 |
| Jκ4 For | 5' TTT TAT TTC CAA CTT TGT CCC CGA 3' | 28 |
| Jκ5 For | 5' TTT CAG CTC CAG CTT GGT CCC AGC 3' | 29 |

C. Reamplification primers containing restriction sites
Mouse VH Sfi back primers

| VH1 Sfi | 5' GTC CTC GCA ACT GCG GCC CAG CCG GCC ATG GCC GAG GTG CAG CTT CAG GAG TCA GG 3' | 30 |
| VH2 Sfi | 5' GTC CTC GCA ACT GCG GCC CAG CCG GCC ATG GCC GAT GTG CAG CTT CAG GAG TCR GG 3' | 31 |
| VH3 Sfi | 5' GTC CTC GCA ACT GCG GCC CAG CCG GCC ATG GCC CAG GTG CAG CTG AAG SAG TCA GG 3' | 32 |
| VH4/6 Sfi | 5' GTC CTC GCA ACT GCG GCC CAG CCG GCC ATG GCC GAG GTY CAG CTG CAR CAR TCT GG 3' | 33 |
| VH5/9 Sfi | 5' GTC CTC GCA ACT GCG GCC CAG CCG GCC ATG GCC CAG GTY CAR CTG CAG CAG YCT GG 3' | 34 |
| VH7 Sfi | 5' GTC CTC GCA ACT GCG GCC CAG CCG GCC ATG GCC GAR GTG AAG CTG GTG GAR TCT GG 3' | 35 |
| VH8 Sfi | 5' GTC CTC GCA ACT GCG GCC CAG CCG GCC ATG GCC GAG GTT CAG CTT CAG CAG TCT GG 3' | 36 |
| VH10 Sfi | 5' GTC CTC GCA ACT GCG GCC CAG CCG GCC ATG GCC GAA GTG CAG CTG KTG GAG WCT GG 3' | 37 |
| VH11 Sfi | 5' GTC CTC GCA ACT GCG GCC CAG CCG GCC ATG GCC CAG ATC CAG TTG CTG CAG TCT GG 3' | 38 |

36 Mouse Jκ Not forward primers

| Jκ1 Not | 5' GAG TCA TTC TCG ACT TGC GGC CGC TTT GAT TTC CAG CTT GGT GCC TCC 3' | 39 |
| Jκ2 Not | 5' GAG TCA TTC TCG ACT TGC GGC CGC TTT TAT TTC CAG CTT GGT CCC CCC 3' | 40 |
| Jκ3 Not | 5' GAG TCA TTC TCG ACT TGC GGC CGC TTT TAT TTC CAG TCT GGT CCC ATC 3' | 41 |
| Jκ4 Not | 5' GAG TCA TTC TCG ACT TGC GGC CGC TTT TAT TTC CAA CTT TGT CCC CGA 3' | 42 |
| Jκ5 Not | 5' GAG TCA TTC TCG ACT TGC GGC CGC TTT CAG CTC CAG CTT GGT CCC AGC 3' | 43 |

R = A/G, Y = C/T, S = G/C, K = G/T, W = A/T, M = A/C, V = C/G/A, B = G/C/T, and H = C/A/T.

scFv gene repertoires were assembled from purified $V_H$ and $V_K$ gene repertoires and linker DNA by using splicing by overlap extension. Linker DNA encoded the peptide sequence ($G_4S_3$, SEQ ID NO: 278) Huston, et al. (1988) *Proc. Natl. Acad. Sci. USA* 85:5879-5883) and was complementary to the 3' ends of the rearranged $V_H$ genes and the 5' ends of the rearranged V. genes. The $V_H$ and $V_K$ DNAs (1.5 µg of each) were combined with 500 ng of linker DNA (Recombinant Phage Antibody System; Pharmacia Biotech) in a 25 µl PCR mixture containing 250 µm (each) deoxynucteoside triphosphate, 1.5 mM MgCl, 10 µg of bovine serum albumin/ml, and 1 µl (5 U) of Taq DNA polymerase (Promega) in the buffer supplied by the manufacturer, and the mixture was cycled 10 times (at 94° C. for 1 min, 62° C. for 1 min, and 72° C. for 1 min) to join the fragments. Flanking oligonucleotide primers (RS, provided in the Recombinant Phage Antibody System kit, for library I and an equimolar mixture of $V_H$Sfi and JKNot primers [Table 1] for library 2) were added, and the reaction mixture was cycled for 33 cycles (at 94° C. for 1 min, 55° C. for 1 min, and 72° C. for 1 min) to append restriction sites.

scFv gene repertoires were gel purified as described above, digested with Sfif and NotI, and purified by electroelution, and 1 µg of each repertoire was ligated into either 1 µg of pCANTAB5E vector (Pharmacia Biotech) (library 1) or 1 µg of pHEN-1 (Hoogenboom, et al. (1991) *Nucleic Acids Res.* 19: 4133-4137) (library 2) digested with SfiI and NotI. The ligation mix was purified by extraction with phenol-chloroform, ethanol precipitated, resuspended in 20 µl of water, and 2.5 µl samples were electroporated (Dower, et al. (1988) *Nucleic Acids Res.* 16:6127-6145) into 50 µl of *E. coli* TG1 (Gibson (1984), Studies on the Epstein-Barr virus genome. University of Cambridge, Cambridge, U.K.). Cells were grown in 1 ml of SOC (Sambrook, et al. supra.) for 30 min and then plated on TYE (Miller (1972) *Experiments in molecular genetics*, Cold Spring Harbor Laboratory, Cold Spring Harbor, N.Y.) medium containing 100 µg of AMP/ml and 1% (wt/vol) GLU(TYE-AMP-GLU). Colonies were scraped off the plates into 5 ml of 2×TY broth (Miller (1972) supra.) containing 100 µg of AMP/ml, 1% GLU (2×TY-AMP-GLU), and 15% (vol/vol) glycerol for storage at −70° C. The cloning efficiency and diversity of the libraries were determined by PCR screening (Gussow, et al. (1989), *Nucleic Acids Res.* 17: 4000) as described by Marks et al. (1991) *Eur. J. Immunol.*, 21: 985-991.

E) Preparation of Phage.

To rescue phagemid particles from the libraries, 10 ml of 2×. TY-AMP-GLU was inoculated with an appropriate volume of bacteria (approximately 50 to 100 µl) from the library stocks to give an $A_{600}$ of 0.3 to 0.5 and bacteria were grown for 30 min with shaking at 37° C. About $10^{12}$ PFU of VCS-M13 (Stratagene) particles were added, and the mixture was incubated at overnight at 4° C. Tubes were blocked for 1 h at 37° C. with 2% MPBS, and selection, washing, and elution were performed exactly as described in reference 35 by using phage at a concentration of $5.0×10^{12}$ TU/ml. One-third of the eluted phage was used to infect 10 ml of log-phase *E. coli* TG1, which was plated on TYE-AMP-GLU plates as described above.

The rescue-selection-plating cycle was repeated three times, after which clones were analyzed for binding by ELISA. Libraries were also selected on soluble BoNT/A $H_c$. For library 1, 1.0 mg of BoNT/A $H_c$ (700 µg/ml) was biotinylated (Recombinant Phage Selection Module; Pharmacia) and purified as recommended by the manufacturer. For each round of selection, 1 ml of phage (approximately $10^{13}$ TU) were mixed with 1 ml of PBS containing 4% skim milk powder, 0.05% Tween 20, and 10 µg of biotinylated BoNT/A/ml. After 1 h at room temperature, antigen-bound phage were captured on blocked streptavidin-coated M280 magnetic beads (Dynabeads; Dynal) as described by Schier et al. (1996) *J. Mol. Biol.*, 255: 28-43. Dynabeads were washed a total of 10 times (three times in TPBS, twice in TMPBS, twice in PBS, once in MPBS, and two more times in PBS). Bound phage were eluted from the Dynabeads by incubation with 100 µl of 100 mM triethylamine for 5 min and were neutralized with 1 M Tris-HCl, pH 7.5, and one-third of the eluate was used to infect log-phase *E. coli* TG1.

For library 2, affinity-driven selections (Hawkins, et al. (1992) J. Mol. Biol. 226: 889-896; Schier, et al. (1996) supra.)) were performed by decreasing the concentration of soluble BoNT/A $H_c$ used for selection (10 µg/ml for round 1, 1 µg/ml for round 2, and 10 ng/ml for round 3). Soluble BoNT/A $H_c$ was captured on 200 µl of $Ni^{2+}$-NTA (Qiagen) via a C-terminal hexahistidine tag. After capture, the $Ni^{2+}$-NTA resin was washed a total of 10 times (5 times in TPBS and 5 times in PBS), bound phage were eluted as described above, and the eluate was used to infect log-phase *E. coli* TG1.

F) Initial Characterization of Binders.

Initial analysis for binding to BoNT/A, BoNT/A IL, and BoNT/A $H_N$ (Chen, et al. (1997) *Infect. Immun.* 65: 1626-1630) was performed by ELISA using bacterial supernatant containing expressed scFv. Expression of scFv (De Bellis, et al., (1990) *Nucleic Acids Res.* 18: 1311) was performed in 96-well microtiter plates as described by marks et al. (1991) *J. Mol. Biol.*, 222: 581-597. For ELISA, microtiter plates (Falcon 3912) were coated overnight at 4° C. with either BoNT/A, BoNT/A $H_c$, or BoNT/A $H_N$ (10 µg/ml) in PBS and then were blocked with 2% MPBS for 1 h at room temperature. Bacterial supernatants containing expressed scFv were added to wells and incubated at room temperature for 1.5 h. Plates were washed six times (3 times with TPBS and 3 times with PBS), and binding of scFv was detected via their C-terminal peptide tags (E epitope tag for library 1 in pCANTAB5E and myc epitope tag [Munro, et al. (1986) *Cell* 46: 291-300] for library 2 in pHEN-1) by using either anti-myc tag antibody (9E10; Santa Cruz Biotechnology) or anti-E antibody (Pharmacia Biotech) and peroxidase-conjugated anti-mouse Fc antibody (Sigma), as described by Marks et al. (1991) *J. Mol. Biol.*, 222: 581-597 and Schier et al. (1996) *Gene* 169: 147-155. The number of unique binding scFv was determined by BstN1 fingerprinting and DNA sequencing.

G Subcloning, Expression, and Purification of scFv.

To facilitate, purification, scFv genes were subcloned into the expression vector pUC119mycHis (Schier et al. (1995) *J. Mol. Biol.*, 263: 551-567) or pSYN3, resulting in the addition of a hexahistidine tag at the C-terminal end of the scFv. Two hundred-milliliter cultures of *E. coli* TG1 harboring one of the appropriate phagemids were grown, expression of scFv was induced with IPTG (De Bellis, et al. (1990), *Nucleic Acids Res.* 18:1311), and the cultures were grown at 25° C. overnight. scFv was harvested from the periplasm (Breitling, et al. (1991) *Gene* 104:147-153), dialyzed overnight at 4° C. against IMAC loading buffer (50 mM sodium phosphate [pH 7.5], 500 mM NaCl, 20 mM imidazole), and then filtered through a 0.2-µm-pore-size filter. scFv was purified by IMAC (Hochuli, et al. (1988) *Bio/Technology* 6: 1321-1325) as described by Schier et al. (1995) supra.

To separate monomeric scFv from dimeric and aggregated scFv, samples were concentrated to a volume of <1 ml in a centrifugal concentrator (Centricon 10; Amicon) and fractionated on a Superdex 75 column (Pharmacia) by using HBS. The purity of the final preparation was evaluated by assaying an aliquot by sodium dodecyl sulfate-polyacrylamide gel electrophoresis. Protein bands were detected by Coomassie blue staining. The concentration was determined spectrophotometrically, on the assumption that an $A_{280}$ of 1.0 corresponds to an scFv concentration of 0.7 mg/ml.

H) Measurement of Affinity and Binding Kinetics.

The $K_d$s of purified scFv were determined by using surface plasmon resonance in a BIACORE™ (Pharmacia Biosensor AB). In a BIACORE™ flow cell, approximately 600 RU of BoNT/A $H_c$ (15 µg/ml in 10 mM sodium acetate [pH 4.5]) was coupled to a CM5 sensor chip by using N-hydroxysuccinimide-N-ethyl-N'-(dimethylaminopropyl)carbodimide chemistry (Johnson, et al. (1991) Anal. Biochem. 198: 268-277). This amount of coupled BoNT/A $H_c$ resulted in a maximum RU of 100 to 175 of scFv bound. For regeneration of the surface after binding of scFv, 5 µl of 4 M $MgCl_2$ was injected, resulting in a return to baseline. The surface was reused 20 to 30 times under these regeneration conditions. Association was measured under a continuous flow of 5 µl/min with a concentration range from 50 to 1,000 nM. $k_{on}$ was determined from a plot of ln (dR/dt)/t versus concentration, where R is response and t is time (Karlsson, et al. (1991) *J. Immunol. Methods* 145: 229-240). $k_{off}$ was determined from the dissociation part of the sensorgram at the highest concentration of scFv analyzed (Karlsson, et al. (1991) *J. Immunol. Methods* 145: 229-240) by using a flow rate of 30 µl/min. $K_d$ was calculated as $k_{off}/k_{on}$.

I) Epitope Mapping.

Figure 2:
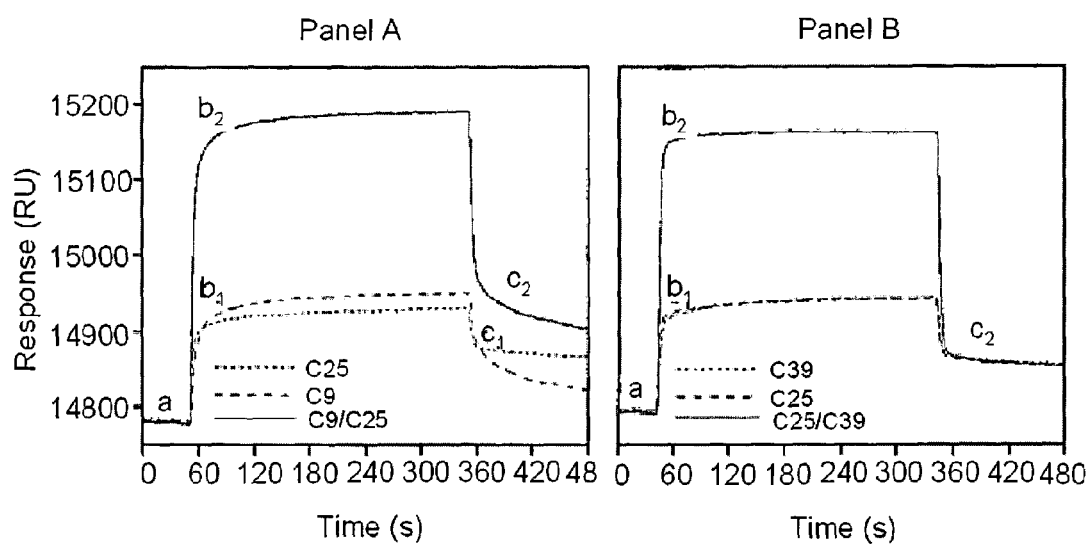
FIG. 2 panel A and panel B show sensor grams illustrating the technique used to epitope map scFv binding to BoNT/A $H_C$. Epitope mapping was performed by using surface plasmon resonance in a BIACORE™, with scFv studied in pairs. Each scFv was injected into the BIACORE™ and allowed to bind to BoNT/A $H_C$ coupled to the sensor chip surface until saturation was achieved. The amount (in RU) bound for each scFv alone was compared to the amount bound when the two scFv were mixed and injected together. Point a shows the baseline, followed by the beginning of injection. Points $b_1$ and $b_2$ show the initial association phase. Points $c_1$ and $c_2$ show the beginning of dissociation. The differences in RU between points a and c equal the amount of scFv bound to BoNT/A $H_C$. Panel A shows two scFv recognizing different epitopes (C25 and C9). The amount bound of the two scFv injected together (C9/C25, point $c_2$) is the sum of the two scFv injected alone ($c_1$). Panel B shows two scFv recognizing the same epitope (C39 and C25). The amount bound for the two scFv injected together (C25/C39; point c) is the same as that for the two scFv injected alone (c). The large differences in RU between points $b_1$ and $c_1$, $b_2$ and $c_2$, and $b_1$ and c are due to differences in refractive index between scFv and running buffer.

Epitope mapping was performed by using surface plasmon resonance in a BIACORE™. In a BIACORE™ flow cell, approximately 1,200 RU of BoNT/A H$_c$ was coupled to a CM5 sensor chip as described above. With a flow rate of 5 a titration of 100 nM to 1 µM scFv was injected over the flow cell surface for 5 min to determine an scFv concentration which resulted in near saturation of the surface. Epitope mapping was performed with pairs of scFv at concentrations resulting in near saturation and at least 100 RU of scFv bound. The amount of scFv bound was determined for each member of a pair, and then the two scFv were mixed together to give a final concentration equal to the concentration used for measurements of the individual scFv. scFv recognizing different epitopes showed an additive increase in the RU bound when injected together (FIG. 2 panel A), while scFv recognizing identical epitopes showed only a minimal increase in RU (FIG. 2 panel B).

J) In Vitro Neutralization Studies.

In vitro neutralization studies were performed by using a mouse hemidiaphragm preparation, as described by Deshpande et al. (1995) *Toxicon* 33: 551-557. Briefly, left and right phrenic nerve hemidiaphragm preparations were excised from male CD/1 mice (25 to 33 g) and suspended in physiological solution (135 mM NaCl, 5 mM KCl, 15 mM NaHCO$_3$, 1 mM Na2HPO$_4$, 1 mM MgCl$_2$, 2 mM CaCl$_2$, and 11 mM GLU). The incubation bath was bubbled with 95% O$_2$-5% CO$_2$ and maintained at a constant temperature of 36° C. Phrenic nerves were stimulated supramaximally at 0.05 Hz with square waves of 0.2 ms duration. Isometric twitch tension was measured with a force displacement transducer (Model FT03; Grass) connected to a chart recorder. Purified scFv were incubated with purified BoNT/A for 30 min at room temperature and then added to the tissue bath, resulting in a final scFv concentration of $2.0 \times 10^{-8}$ M and a final BoNT/A concentration of $2.0 \times 10^{-11}$ M. For each scFv studied, time to 50% twitch tension reduction was determined three times for BoNT/A alone and three times for scFv plus BoNT/A. The combination of S25 and C25 was studied at a final concentration of $2.0 \times 10^{-8}$ M each. Differences between times to 50% twitch reduction were determined by a two-tailed t test, with a P value of <0.05 considered significant.

TABLE 2

Frequency of binding of clones from phage antibody libraries

| Antigen used for selection | Frequency of ELISA-positive clones[a] in selection round: | | |
|---|---|---|---|
| | 1 | 2 | 3 |
| Library 1[b] | | | |
| BoNT/A: immunotube[c] | 20/184 | 124/184 | ND |
| BoNT/A H$_c$: immunotube | 7/92 | 86/92 | 88/92 |
| BoNT/A H$_c$: biotinylated[d] | 7/90 | 90/90 | 90/90 |
| | 14/48 | 48/48 | ND |
| Library 2[e] | | | |
| BoNT/A: immunotube | ND | 81/92 | ND |
| BoNT/A H$_c$: immunotube | ND | ND | 76/92 |
| BoNT/A H$_c$: Ni$^{2+}$-NTA[f] | ND | ND | 67/92 |

[a]Expressed as number of positive clones/total number of clones. For selections on BoNT/A and BoNT/A H$_c$, ELISA was done on immobilized BoNT/A and BoNT/A H$_c$, respectively. ND, data not determined from selection performed.
[b]Derived from a mouse immunized twice with BoNT/A H$_c$ and once with BoNT/A.
[c]Immunotube selections were performed with the antigen absorbed onto immunotubes.
[d]Biotinylated selections were performed in solution with capture on streptavidin magnetic beads.
[e]Derived from a mouse immunized three times with BoNT/A H$_c$.
[f]Ni$^{2+}$-NTA selections were performed in solution with capture on Ni$^{2+}$-NTA agarose.

Results.

A) Phage Antibody Library Construction and Characterization.

Two phage antibody libraries were constructed from the V$_H$ and V$_K$ genes of immunized mice (FIG. 1). For library 1, a mouse was immunized twice with BoNT/A H$_C$ and challenged 2 weeks after the second immunization with 100,000 50% lethal doses of BoNT/A. The mouse survived the BoNT/A challenge and was sacrificed 1 week later. The spleen was removed immediately after sacrifice, and total RNA was prepared. For library construction, IgG heavy-chain and kappa light-chain mRNA were specifically primed and first-strand cDNA was synthesized. V$_H$ and V$_K$ gene repertoires were amplified by PCR, and V$_H$, J$_H$ V$_K$, and J$_K$ primers were provided in the recombinant phage antibody system.

The V$_H$ and V$_K$ gene repertoires were randomly spliced together to create an scFv gene repertoire by using synthetic DNA encoding the 15-amino-acid peptide linker (G4S)$_3$ (SEQ ID NO: 226). Each scFv gene repertoire was separately cloned into the phage display vector pCANTAB5E (Pharmacia). After transformation, a library of $2.1 \times 10^6$ members was obtained. Ninety percent of the clones had an insert of the appropriate size for an scFv gene, as determined by PCR screening, and the cloned scFv genes were diverse, as determined by PCR fingerprinting. DNA sequencing of 10 unselected clones from library 1 revealed that all V$_H$ genes were derived from the murine V$_H$2 family and all V$_K$ genes were derived from the murine V$_K$4 and V$_K$6 families (Kabat, et al. (1991) supra.). Based on this observed V-gene bias, family-specific V$_H$ and V$_K$ primers were designed along with J$_H$ and J$_K$ gene-segment-specific primers (Table 1). These primers were then used to construct a second phage antibody library.

For library 2, a mouse was immunized three times with BoNT/A H$_c$ and sacrificed 2 weeks after the third immunization. The mouse was not challenged with BoNT/A prior to spleen harvest, as this led to the production of non-H$_c$-binding antibodies (see "Selection and initial characterization of phage antibodies" below). The spleen was harvested, and a phage antibody library was constructed as described above, except that V$_H$-, J$_H$, V$_K$-, and J$_K$-specific primers were used. After transformation, a library of $1.0 \times 10^6$ members was obtained. Ninety-five percent of the clones had an insert of the appropriate size for an scFv gene, as determined by PCR screening, and the cloned scFv genes were diverse, as determined by PCR fingerprinting (data not shown). DNA sequencing of 10 unselected clones from library 2 revealed greater diversity than was observed in library 1; V$_H$ genes were derived from the V$_{H1}$, V$_K$2, and V$_K$3 families, and V$_K$ genes were derived from the V$_K$2, V$_K$3, V$_K$4, and V$_K$6 families (Kabat, et al. 1991 supra.).

B) Selection and Initial Characterization of Phage Antibodies.

To isolate BoNT/A binding phage antibodies, phage were rescued from the library and selected on either purified BoNT/A or BoNT/A H$_c$. Selections were performed on the holotoxin in addition to IL, since it was unclear to what extent the recombinant toxin H$_c$ would mimic the conformation of the $H_c$ in the holotoxin. Selection for BoNT/A and BoNT/A $H_c$ binders was performed on antigen adsorbed to polystyrene. In addition, $H_c$ binding phage were selected in solution on biotinylated IL, with capture on streptavidin magnetic beads (for library 1) or on hexahistidine tagged IL, with capture on $Ni^{2+}$-NTA agarose (for library 2). Selections in solution were utilized based on our previous observation that selection on protein adsorbed to polystyrene could yield phage antibodies that did not recognize native protein (Schier et al. (1995) *Immunotechnology*, 1: 73-81). Selection in solution was not performed on the holotoxin due to our inability to successfully biotinylate the toxin without destroying immunoreactivity.

After two to three rounds of selection, at least 67% of scFv analyzed bound the antigen used for selection (Table 2). The number of unique scFv was determined by DNA fingerprinting followed by DNA sequencing, and the specificity of each scFv was determined by ELISA on pure BoNT/A and recombinant BoNT/A $H_c$ and HN scFv binding BoNT/A but not binding, $H_c$ or HN were presumed to bind the light chain (catalytic domain). A total of 33 unique scFv were isolated from mice immunized with $H_c$ and challenged with BoNT/A (Table 3, library 1). When library 1 was selected on holotoxin, 25 unique scFv were identified. Only 2 of these scFv, however, bound IL, with the majority (Hathaway, et al. (1984) *J. Infect. Dis.* 150:407-412) binding the light chain and 2 binding $H_N$. The two $H_c$ binding scFv did not express as well as other scFv recognizing similar epitopes, and they were therefore not characterized with respect to affinity or neutralization capacity (see below).

Selection of library 1 on $H_c$ yielded an additional eight unique scFv (Tables 3 and 4). Overall, however, only 50% of scFv selected on $H_c$ also bound holotoxin. This result suggests that a significant portion of the $H_c$ surface may be inaccessible in the holotoxin. Alternatively, scFv could be binding, $H_c$ conformations that do not exist in the holotoxin. From mice immunized with $H_c$ only (library 2), all scFv selected on holotoxin also bound $H_c$. As with library 1, however, only 50% of scFv selected on $H_c$ bound holotoxin. In all, 18 unique $H_c$ binding scFv were isolated from library 2, resulting in a total of 28 unique binding scFv (Tables 3 and 4). scFv of identical or related sequences were isolated on both $H_c$ immobilized on polystyrene and $H_c$ in solution. Thus, in the case of $H_c$, the method of selection was not important.

TABLE 3

Specificity of BoNT binding scFv selected from phage antibody libraries.

| scFv Specificity | Number of unique scFv | |
|---|---|---|
| | library 1 | library 2 |
| BoNT/A $H_c$ | 10 | 18 |
| BoNT/A $H_N$ | 2 | 0 |
| BoNT/A light chain | 21 | 0 |
| Total | 33 | 18 |

C) Epitope Mapping.

All 28 unique $H_c$ binding scFv were epitope mapped using surface plasmon resonance in a BIACORE™. Epitope mapping was performed with pairs of scFv at concentrations resulting in near saturation of the chip surface and at least 100 RU of scFv bound. The amount of scFv bound was determined for each member of a pair, and then the two scFv were mixed together to give a final concentration equal to the concentration used for measurements of the individual scFv. Those scFv recognizing different epitopes showed an additive increase in the RU bound when injected together (FIG. 2, panel A), while scFv recognizing identical epitopes showed only a minimal increase in RU (FIG. 2, panel B). By this technique, mapping of the 28 scFv yielded 4 nonoverlapping epitopes recognized on (Table 4). scFv recognizing only epitopes 1 and 2 were obtained from library 1, whereas scFv recognizing all 4 epitopes were obtained from library 2.

Many of the scFv recognizing the same epitope (C1 and S25; C9 and C15; 1E8 and 1G7; 1B6 and 1C9; C25 and C39; 2G5, 3C3, 3F4, and 3H4; 1A1 and 1F1; 1B3 and 106; 1G5 and 1H6; 1F3 and 2E8) had $V_H$ domains derived from the same V-D-J rearrangement, as evidenced by the high level of homology of the $V_H$CDR3 and $V_H$-gene segment (Table 4). These scFv differ only by substitutions introduced by somatic hypermutation or PCR error. For epitopes 1 and 2, most or all of the scFv recognizing the same epitope are derived from the same or very similar $V_H$-gene segments but differ significantly with respect to $V_H$CDR3 length and sequence (5 of 9 scFv for epitope 1; 8 of 8 scFv for epitope 2) (Table 4). These include scFv derived from different mice. Given the great degree of diversity in $V_H$CDR2 sequences in the primary repertoire (Tomlinson et al. (1996) *J. Mol. biol.*, 256: 813-817), specific $V_H$-gene segments may have evolved for their ability to form binding sites capable of recognizing specific pathogenic antigenic shapes. In contrast, greater structural variation appears to occur in the rearranged $Y_K$ genes. For example, three different germ line genes and CDR1 main-chain conformations (Chothia, et al. (1987) *J. Mol. Biol.* 196: 901-917) are observed for epitope 21 where all the $V_H$ (genes are derived from the same germ line gene. Such "promiscuity" in chain pairings has been reported previously (Clackson, et al. (1991) Nature 352: 624-628).

D) Affinity, Binding Kinetics, and In Vitro Toxin Neutralization.

Affinity, binding kinetics, and in vitro toxin neutralization were determined for one representative scFv binding to each epitope. For each epitope, the scFv chosen for further study had the best combination of high expression level and slow $k_{off}$, as determined during epitope mapping studies. $K_d$ for the four scFv studied ranged between $7.3 \times 10^{-8}$ and $1.1 \times 10^{-9}$ M (Table 5), values comparable to those reported for monoclonal IgG produced from hybridomas (Foote, et al., *Nature* 352:530-532 (1991)). C25 has the highest affinity ($K_d = 1.1 \times 10^{-9}$ M) reported for an anti-botulinum toxin antibody. $k_{on}$ differed over 84-fold, and

TABLE 4

Deduced protein sequence of VH and VL of BONT/A HC binding scFv, classified by epitope recognized

| Region; Epitope | Clone; Lib[a] | SEQ ID NO | Sequence[b] Framework 1-CDR1-Framework 2-CDR2-Framework 3-CDR3-Framework 4 |
|---|---|---|---|
| $V_H$; 1 | C15; 1 | 230 | QVKLQQSGAELVRPGASVKLSCKTSGYSFT-SYWMNW-VKQGPGQGLEWIG-MIHPSNSEIRFNQKFED-MATLTVDKSSSTAYMQLSSPTSEDSAVYYCAR-GIYYDYDGGNYYAMDY-WGQGTTVTASS |
| | C9; 1 | 231 | QVKLQQSGAELVRPGASVKLSCKTSGYSFT-SYWMN-WVKQGPGQGLEWIG-MIHPSNSEIRFNQKFEN-MATLTVDKSSSTAYMQLSSPTSEDSAVYYCAR-GIYYVYDGGNYYAMDY-WGQGTTVTVSS |
| | 1D5; 2 | 232 | EVKLVESGAELVRPGASVNLSCKASGYSFT-SYWMN-WVKQRPGQGLEWIG-MIHPSNSETRLNQKFKD-KATLTVDKSSSTAYMQLSSPTSEDSAVYYCAR-GIYYDYDEGYYYTLDY-WGQGTTLTVSS |
| | C1; 1 | 233 | QVKLQQSGAELVRPGASVKLSCKASGYSFT-SYWMN-WVKQRPGQGLEWIG-MIHPSNSDTRFNQKFED-KATLTVDRSSSTAIHQLSSPTSEDSAVYYCAR-GLYGYGFWYFDV-WGQGTTVTVSS |
| | S25; 1 | 234 | QVKLQQSGAELVRPGASVKLSCKASGYSLT-SYWMN-WVKQRPGQGLEWIG-MIHPSDSDTRFNQKFED-KATLTVDTSSSTAYMQLSSPTSEDSAVYYCAR-GLYNGFWYFDV-WGQGTTVTVSS |
| | 1B6; 2 | 235 | QVQLQQSGAELVRPGVSVKISCKASGYTFI-DYAMH-WVKQSPAKSLEWIG-VISSYYGDTDYNQIFKG-KATLTVDKSSNTAYMELARLTSDDSAIYYCAR-RGKGAMDY-WGQGTTVTVSS |
| | 1C9; 2 | 236 | QVQLKQSGAELVRPGVSVKISCKGSGYTFI-DYAVH-WVKQSHAKSLEWIG-VISTYYGDADYNPKFKG-KATLTVNKSSNTAYMELPRLTSEDSAIYYCAR-RGKGAMDY-WGQGTSVTVSS |
| | 1E8; 2 | 237 | EVQLQESGPGLVKPSQSLSLTCTVTGYSIT-DYAWN-WIRQFPGKKLEWMG-YISYSGSTGYNPSLKS-RISITRDTSKNQFFLQLNSVTTEDTGTYYCAR-GYDAMDY-WGQGTSVTVSS |
| | 1G7; 2 | 238 | EVQLQESGPGLVKPSQSLSLTCTVTGYSIT-DYAWY-WIRQFPGKKLEWMG-YISYSGSTGYNPSLKS-RISITRDTSKNQFFLQLNSVTTEDTGTYYCAR-GYDAMDY-WGQGTSVTVSS |
| $V_H$; 2 | 1A1; 2 | 239 | EVKLVESGGGLVQPGGSRKLSCATSGFTFS-DYYMS-WIRQSPDKRLEWVA-TISDGGTYTYYPDSVKG-RFTISRDNAKNTLYLQMSSLKSEDTAMYYCVR-HGYGNYPSHWYFDV-WGAGTTVTVSS |
| | 1F1; 2 | 240 | EVKLVESGGGLVQPGGSLKLSCAASGFTFS-NYGMS-WVRQTPDKRLEWVA-MISSGGSYNYYSDSVKG-RVTISRDNAKSTLYLQMSSLQSEDTAMYLCTR-HGYGNYPSYWYFDV-WGAGTTVTVSS |
| | C39; 1 | 241 | QVQLQESGGGSVKPGGSLKLSCAASGFTFS-DYYMS-WVRQTPEKRLEWVA-TISDGGSYTYYPDSVKG-RFTISRDNAKNNLYLQMSSLKSEDTAIYYCVR-YRYDEGLDY-WGQGTTVTVSS |
| | C25; 1 | 242 | QVQLQESGGGLVKPGGSLKLSCAASGFTFS-DYYMY-WVRQTPEKRLEWVA-TISDGGSYTYYPDSVKG-RFTISRDNAKNNLYLQMSSLKSEDTAMYYCSR-YRYDDAMDY-WGQGTTVTVSS |
| | 2G5; 2 | 243 | EVKLVESGGGLVKPGGSLKLSCAASGFTFS-SYAMS-WVRQTPEKRLEWVA-TISDGGTYTYYTDNVKG-RFTISRDNAKHNLYLQMSHLKSEDTAMYYCAR-NLPYDHVDY-WGQGTSVTVSS |
| | 3C3; 2 | 244 | EVKLKESGGGLVKPGGSLKLSCAASGFTFS-SYAMS-WVRQTPEKRLEWVA-TISDGGTYTYYTDNVKG-RFTISRDNAKHNLYLQMSHLKSEDTAMYYCAR-NLPYDHVDY-WGQGTSVTVSS |
| | 3F4; 2 | 245 | EGKLVESGGGLVKPGGSLKLSCAASGFTFS-SYAMS-WVRQTPEHRLEWVA-TISDGGTFTYYTDNVKG-RFTISRDNAKHNLYLQMSHLKSEDTAMYYCAR-NLPYDHVDY-WGQGTSVTVSS |
| | 3H4; 2 | 246 | EVKLVESGGGLVKPGGPLKLSCAASGFTFS-SYAMS-WVRQTPEHRLEWVA-TISDGGTFTYYTDNVKG-RFTISRDNAKHNLYLQMSHLKSEDTAMYYCAR-NLPYDHVDY-WGQGTSVTVSS |
| $V_H$; 3 | 1B3; 2 | 247 | EVQLQESGGGVVQPGRSLRLSCAASGFTFS-SYAMH-WVRQAPGKGLEWVA-VISYDGSNKYYADSVKG-RFTISRDNSKNTLYLQMNSLRAEDTAVYYCAR-DWSEGYYYYGMDV-WGQGTTVIVSS |
| | 1C6; 2 | 248 | QIQLLQSGGGVVQPGRSLRLSCAASGFTFS-SYAMH-WVRQAPGKGLEWVA-VISYDGSNKYYADSVKG-RFTISRDNSKNTLYLQMNSLRAEDTAVYYCAR-DWSEGYYYYGMDV-WGQGTTVIVSS |
| | 2B6; 2 | 249 | VKLVESGPGLVKPSQSLSLTCTVTGYSITS-DYAWN-WIRQFPGNKLEWMG-YINYDGSNNYNPSLKN-RISITRDTSKNQFFLKLNSVTSEDTATYYCAR-AGDGYYVDWYFDV-WGTGTTVIVSS |
| | 1G5; 2 | 250 | QVQLQQSGAELVQPGASVKMSCKASGYTFT-SYWTT-WVKQRPGQGLEWIG-DIYPGSGSTNYNEKFKS-KATLTVDTSSSTAYMQLSSLTSEDSAVYYCAR-ELGDAMDY-WGQGTSVIVSS |
| | 1H6; 2 | 251 | EVQLQQSGAELVKPGASVKMSCKASGYTFT-SYWTT-WVKQRPGQGLEWIG-DIYPDSGSTNYNEKFKS-KATLTVDTSSSTAYMQLSSLTSEDSAVYYCAR-ELGDAMDY-WGQGTSVIVSS |
| $V_H$; 4 | 1F3; 2 | 252 | EVQLQQSGAELVKPGASVKLSCKASGYTFT-SFWMH-WVKQRPGRGLEWIG-RLDPNSGETKYNEKFKS-KATLTVDKPSSTAYMELSSLTSEDSAVYYCAR-EAYGYWNFDV-WGTGTTVTVSS |
| | 2E8; 2 | 253 | EVQLQQSGAELVKPGASVKLSCKASGYTFT-SFWMH-WVKQRPGRGLEWIG-RLDPNSGETKYNKKFKS-KATLTVDKPSSTAYMELSSLTSEDSAVYYCAR-EAYGYWNFDV-WGTGTTVTVSS |
| $V_L$; 1 | C15; 1 | 254 | DIELTQSPAIMSASPGEKVIMTC-SASSSVSHMY-WYQQKPGSSPRLLIY-DTSNLAS-GVPIRFSGSGSGTSYSLTISRMEAEDSATYYC-QQWSSYPFT-FGSGTKLELKR |
| | C9; 1 | 255 | DIDLTQSPAIMSSSPGEKVIITC-SASSSVSYMH-WFQQKPGTSPKPWIY-STSNLAS-GVPARFSGSGSGTSYSLTISSVEAEDAATYYC-QQYSGYPLT-FGAGTKLEIKR |
| | 1D5; 2 | 256 | DIELTQSPAIMAASPGEKVIITC-SASSSISSSNLH-WYQQKSETSPKPWIY-GTSNLAS-GVPVRFSGSGSGTSYSLTISSMEAEDAATYYC-QQWGSYPLT-FGGGTKLEIKR |
| | C1; 1 | 257 | DIELTQSPAIMSASPGEKVIMTC-SASSSVSYMY-WYQQKPGSSPRLLIY-DTSNLAS-GVPVRFSGSGSGTSYSLTISRMEAEDAATYYC-QQWSSYPLT-FGAGTKLELKR |
| | S25; 1 | 258 | DIELTQSPALMAASPGEKVIITC-SVSSSISSSNLH-WYQQKSGTSPKPWIY-GTSNLAS-GVPVRFSGSGSGTSYSLTISSMEAEDAATYYC-QQWSSYPLT-FGAGTKLEIKR |

TABLE 4-continued

Deduced protein sequence of VH and VL of BONT/A HC binding scFv, classified by epitope recognized

| Region; Epitope | Clone; Lib[a] | SEQ ID NO | Sequence[b] Framework 1-CDR1-Framework 2-CDR2-Framework 3-CDR3-Framework 4 |
|---|---|---|---|
| | 1B6; 2 | 259 | DIELTQSPASLAVSLGQRAIISC-RASESVDSYGNSFMH-WYQQKPGQPPKLLIY-RASNLES-GIPARFSGSGSRTDFTLTINPVEADDVATYYC-QQSNEDPPT-FGAGTKLELKR |
| | 1C9; 2 | 260 | DIELTQSPASLAVSLGQRAIISC-RASESVDSYGNSFMH-WYQQKPGQPPKLLIY-RASNLES-GIPARFSGSGSRTDFTLTINPVEADDVATYYC-QQSNEDPYT-FGGGTKLEIKR |
| | 1E8; 2 | 261 | DIELTQSPAIMSASPGEKVIMTC-SASSSVSYMH-WYQQKSGTSPKRWIY-DTSKLAS-GVPARFSGSGSGTSYSLTISSMEAEDAATYYC-QQWSSNPLT-FGAGTKLELKR |
| | 1G7; 2 | 262 | DIELTQSPAIMSASPGEKVIMTC-SASSSVSYMH-WYQQKSGTSPKRWIY-DTSKLAS-GVPARFSGSGSGTSYSLTISSMEAEDAATYYC-QQWSSNPLT-FGAGTKLELKR |
| $V_L$; 2 | 1A1; 2 | 263 | DIELTQSPASLAVSLGQRATISC-RASESVDSYGNSFMH-WYQQKPGQPPKLLIY-LASNLES-GVPARFSGSGSRTDFTLTIDPVEADDAATYYC-QQNNEDPYT-FGGGTKLEIKR |
| | 1F1; 2 | 264 | DIELTQSPTSLAVSLGQRATISC-RASESVDSYGNSFMH-WYQQKPGQPPKLLIY-LASNLES-GVPARFSGSGSRTDFTLTIDPVEADDAATYYC-QQNNEDPYT-FGGGTKLEIKR |
| | C39; 1 | 265 | DIELTQSPASLAVSLGRRATISC-RASESVDSYGHSFMH-WYQQKPGQPPKLLIY-LASNLES-GVPARFSGSGSRTDFTLTIDPVEADDAATYYC-QQNNEDPYT-FGGGTKLEIKR |
| | C25; 1 | 266 | DIELTQSPASLAVSLGQRATISC-RASESVDSYGHSFMQ-WYQQKPGQPPKLLIY-RASNLEP-GIPARFSGSGSGTDFTLTINPVEADDVATYYC-QQSNEDPFT-FGSGTKLEIKR |
| | 2G5; 2 | 267 | DIELTQSPAIMSASPGEKVTTTC-SASSSVSYMG-WFQQKPGTSPKLWIY-STSNLAS-GVPARFSGSGSGTSYSLTISRMEAEDAATYYC-QQRSSYPYT-FGSGDQAGNKS |
| | 3C3; 2 | 268 | DIELTQSPAIMSASPGEKVTTTC-RASESVDSYGHSFMQ-WFQQKPGTSPKLWIY-STSNLAS-GVPARFSGSGSGTSYSLTISRMEAEDAATYYC-QQRSSYPYT-FGSGDQAGNKR |
| | 3F4; 2 | 269 | DTELTQSPAIMSASPGEKVTMTC-SASSSVSYMY-WYQQKPGSSPRLLIY-DTSNLAS-GVPVRFSGSGSGTSYSLTISRMEAEDAATYYC-QQWSSYPPT-FGSGTKLEIKR |
| | 3H4; 2 | 270 | DIELTQSPAIMSASPGEKVTMTC-RASSSVSSSYLG-WYQQKPGSSPRLLIY-DTSNLAS-GVPVRFSGSGSGTSYSLTISRMEAEDAATYYC-QQWSSYPPT-FGSGTKLEIKR |
| $V_L$; 3 | 1B3; 2 | 271 | DSELTQSPTTMAASPGEKITTTC-SASSSISSNYLH-WYQQRPGFSPKLLIY-RTSNLAS-GVPARFSGSGSGTSYSLTIGTMEAEDVATYYC-QQGSSIPRT-FGGGTKLEIKR |
| | 1C6; 2 | 272 | DIELTQSPASLAVSLGRRATTSC-RASESVEYYGTSLMQ-WYQQKPGQPPKLLIY-AASNVES-GVPARFSGSGSGTDFSLNIHPVEEDIAMYFC-QQSRKVPWT-FGGGTKLEIKR |
| | 2B6; 2 | 273 | YIELTQSPASLAVSLGQRATTSC-RASESVDSYGNSFMH-WYQQKPGQPPKLLIY-LASNLES-GVPARFSGSGSRTDFTLTIDPVEADDAATYYC-QQNNEDPYT-FGGGTKLEIKS |
| | 1G5; 2 | 274 | DIELTQSPASLAVSLGQRATTSC-RASESVEYYGTSLMQ-WYQQKPGQPPKLLIY-AASNVES-GAPARFSGSGSGTDFSLNIHPVEEDDIAMYFC-QQSRKVPYT-FGGGTKLEIKR |
| | 1H6; 2 | 275 | DIELTQSPAIMSASPGEKVTTTC-SVSSSISSSNLH-WYQQKSGTSPKLWIY-GTSNLAS-GVPVRFSGSGSGTSYSLTISSMEAEDAATYYC-QQWSSYPLT-FGAGTKVELRR |
| $V_L$; 4 | 1F3; 2 | 276 | DIELTQSPASMSASPGEKVTMTC-RATSSVSSSYLH-WYQQKSGASPKLWIY-SASNLAS-GVPSRFSGSGSGTSYSLTISSVEAEDAATYYC-QQYIGYPYT-FGGGTKLEIKR |
| | 2E8; 2 | 277 | DIELTQSPTTMAASPGEKITITC-SASSSIGSNYLH-WYQQKPGFSPKLLIY-RTSNLAS-GVPARFSGSGSGTSYSLTIGAMEAEDVATYYC-QQGSSIPYT-FGGGTKLEIKR |

[a]Lib, library

[b]Full-length sequences were not determined for clines C12, C13, C2 and S44 (all bind epitope 1). Accession can be made through GenBank with nos AF003702 to AF003725.

$k_{off}$ differed over 33-fold, between scFv (Table 5). In vitro toxin neutralization was determined by using a mouse hemidiaphragm preparation and measuring the time to 50% twitch tension reduction for BoNT/A alone and in the presence of $2.0 \times 10^{-8}$ M scFv. Values are reported in time to 50% twitch reduction. scFv binding to epitope 1 (S25) and epitope 2 (C25) significantly prolonged the time to neuroparalysis: 1.5-fold (152%) and 2.7-fold (270%), respectively (Table 5 and FIG. 3). In contrast, scFv binding to epitopes 3 and 4 had no significant effect on the time to neuroparalysis. A mixture of S25 and C25 had a significant additive effect on the time to neuroparalysis, with the time to 50% twitch reduction increasing 3.9-fold (390%).

TABLE 5

Affinities, binding kinetics, and in vitro toxin neutralization results of scFv selected from phage antibody libraries

| scFv clone | Epitope | $K_d^a$ (M) | $k_{on}$ ($10^4 M^{-1} s^{-1}$) | $k_{off}$ ($10^{-3} s^{-1}$) | Paralysis Time[b] |
|---|---|---|---|---|---|
| S25 | 1 | $7.3 \times 10^{-8}$ | 1.1 | 0.82 | $85 \pm 10^c$ |
| C25 | 2 | $1.1 \times 10^{-9}$ | 30 | 0.33 | $151 \pm 12^c$ |
| C39 | 2 | $2.3 \times 10^{-9}$ | 14 | 0.32 | $139 \pm 8.9^c$ |
| 1C6 | 3 | $2.0 \times 10^{-8}$ | 13 | 2.5 | $63 \pm 3.3$ |
| 1F3 | 4 | $1.2 \times 10^{-8}$ | 92 | 11 | $52 \pm 1.4$ |
| C25 + S25 Combination | | | | | $218 \pm 22^{c,d}$ |
| BoNT/A pure toxin (control) | | | | | $56 \pm 3.8$ |

[a] $k_{on}$ and $k_{off}$ were measured by surface plasmon resonance and $K_d$ calculated as $k_{off}/k_{on}$.
[b] Time (min.) to 50% twitch reduction in mouse hemidiaphragm assay using 20 nM scFv + 20 pM BoNT/A, compared to time for BoNT/A alone. For C25 + S25 combination, 20 nM scFv each was used. Each value is the mean ± SEM of at least three observations.
[c] p < 0.01 compared to BoNT/A.
[d] p < 0.05 compared to C25

Discussion.

BoNTs consist of a heavy and a light chain linked by a single disulfide bond. The carboxy-terminal half of the toxin binds to a specific membrane receptor(s), resulting in internalization, while the amino-terminal half mediates translocation of the toxin from the endosome into the cytosol. The light chain is a zinc endopeptidase which cleaves an essential synaptosomal protein, leading to failure of synaptic transmission and paralysis. Effective immunotherapy must prevent binding of the toxin to the receptor, since the other two toxin functions occur intracellularly. Identification of epitopes on $H_c$ which mediate binding is an essential first step, both to the design of better vaccines and to development of a high-titer neutralizing monoclonal antibody (or antibodies) for passive immunotherapy.

For this work, we attempted to direct the immune response to a neutralizing epitope(s) by immunization with recombinant BoNT/A $H_c$. This should lead to the production of antibodies that prevent binding of toxin to its cellular receptor(s). One limitation of this approach is the extent to which recombinant $H_c$ mimics the conformation of $H_c$ in the holotoxin. The fact that 50% of antibodies selected on $H_c$ recognize holotoxin suggests significant structural homology for a large portion of the molecule. Although 50% of antibodies selected on $H_c$ do not bind holotoxin, this could result from packing of a signif-icant portion of the $H_c$ surface against other toxin domains. Our results do not, however, exclude the possibility that some of these antibodies are binding $H_c$ conformations that do not exist in the holotoxin or that conformational epitopes present in the holotoxin are absent from recombinant $H_c$. This could lead to failure to generate antibodies to certain conformational epitopes. Regardless, immunizing and selecting with $H_c$ resulted in the isolation of a large panel of monoclonal antibodies which bind holotoxin. In contrast, monoclonal antibodies isolated after immunization with holotoxin or toxoid bind to other toxin domains ($H_N$ or light chain) or to nontoxin proteins present in crude toxin preparations and toxoid (see results from library 1, above, and Emanuel et al. (1996) j. Immunol. Meth., 193: 189-197).

To produce and characterize the greatest number of monoclonal antibodies possible, we used phage display. This approach makes it possible to create and screen millions of different antibodies for binding. The resulting antibody fragments are already cloned and can easily be sequenced to identify the number of unique antibodies. Expression levels in E. coli are typically adequate to produce milligram quantities of scFv, which can easily be purified by IMAC after subcloning into a vector which attaches a hexahistidine tag to the C terminus. Ultimately, the $V_H$ and $V_L$ genes can be subcloned to construct complete IcG molecules, grafted to construct humanized antibodies, or mutated to create ultra-high-affinity antibodies. By this approach, 28 unique monoclonal anti-BoNT/A $H_c$ antibodies were produced and characterized.

The antibody sequences were diverse, consisting of 3 different $V_H$-gene families, at least 13 unique V-D-J rearrangements, and 3 $V_K$-gene families Generation of this large panel of BoNT/A $H_c$ antibodies was a result of the choice of antigen used for immunization and selection (BoNT/A $H_c$). For example, a Fab phage antibody library constructed from the V genes of mice immunized with pentavalent toxoid yielded only two Fab which bound pure toxin (in this case, BoNT/B). The majority of the Fab bound nontoxin proteins present in the toxoid (Emanuel, et al., J. Immunol. Methods 193:189-197 (1996)).

Despite the sequence diversity of the antibodies, epitope mapping revealed only four nonoverlapping epitopes. Epitopes 1 and 2 were immunodominant, being recognized by 21 of 28 (75%) of the antibodies. Interestingly, approximately the same, number (three to five) of immunodominant BoNT/A $H_c$ peptide (nonconformational) epitopes are recognized by mouse and human polyclonal antibodies after immunization with pentavalent toxoid and by horse polyclonal antibodies after immunization with formaldehyde-inactivated BoNT/A (Atassi (1996) J. Protein Chem., 15: 691-699).

scFv binding epitopes 1 and 2 resulted in partial antagonism of toxin-induced neuroparalysis at the mouse neuromuscular junction. When administered together, the two scFv had an additive effect, with the time to neuroparalysis increasing significantly. These results are consistent with the presence of two unique receptor binding sites on BoNT/A $H_c$. While the BoNT/A receptor(s) has not been formally identified, the results are consistent with those of ligand binding studies, which also indicate two classes of receptor binding sites on toxin, high and low affinity, and have led to a "dual receptor" model for toxin binding (Montecucco (1986) Trends Biochem. Sci. 11:314-317). Whether both of these sites are on $H_c$, however, is controversial. In two studies, BoNT/A $H_c$ partially inhibited binding and neuromuscular paralysis (Black, et al. (1986) J. Cell Biol., 103:521-534; Black, et al. (1980) Am. J. Med., 69:567-570), whereas Daniels-Holgate et al. (1996) J. Neurosci. Res. 44:263-271, showed that BoNT/A $H_c$ inhibited binding at motor nerve terminals but had no antagonistic effect on toxin-induced neuroparalysis at the mouse neuromuscular junction. Our results are consistent with the presence of two "productive" receptor binding sites on $H_c$ which result in toxin internalization and toxicity. Differences in scFv potency may reflect differences in affinity of $H_c$ for receptor binding sites or may reflect the greater than 10-fold difference in affinity of scFv for $H_c$. Finally, we have not formally shown that any of the scFv actually block binding of toxin to the cell surface. It is conceivable that the observed effect on time to neuroparalysis results from interference with a postbinding event.

scFv antagonism of toxin-induced neuroparalysis in the mouse hemidiaphragm assay was less than that (7.5-fold prolongation of time to neuroparalysis) observed for $2.0 \times 10^{-9}$ M polyclonal equine antitoxin (PerImmune Inc.). This difference could be due to the necessity of blocking additional binding sites, differences in antibody affinity or avidity, or a cross-linking effect leading to aggregated toxin which cannot bind. Affinity of antibody binding is also likely to be an important factor, since the toxin binds with high affinity to its receptor (Williams et al. (1983) *Eur. J. Biochem.*, 131: 437-445) and can be concentrated inside the cell by internalization. Of note, the most potent scFv has the highest affinity for $H_c$. Availability of other scFv described here, which recognize the same neutralizing epitope but with different $K_d$s, should help define the importance of affinity. These scFv, however, differ by many amino acids and may also differ in fine specificity, making interpretation of results difficult. Alternatively, mutagenesis combined with phage display can lead to the production of scFv which differ by only a few amino acids in sequence but vary by several orders of magnitude in affinity (Schier et al. (1996) *J. Mol. Biol.*, 263: 551-567). The same approach can be used to increase antibody affinity into the picomolar range (Id.).

The "gold standard" for neutralization is protection of mice against the lethal effects of toxin coinjected with antibody. While the relationship between in vitro and in vivo protection has not been formally established, equine antitoxin potentially neutralizes toxin in both types of assays (see above and Hatheway et al. (1984) *J. Infect. Dis.*, 150: 407-412). It is believed that this relationship holds for the scFv reported here, and this can be verified experimentally.

Such studies are not possible with small (25-kDa) scFv antibody fragments. The small size of scFv leads to rapid redistribution (the half-life at a phase is 2.4 to 12 min) and clearance (the half-life at β phase is 1.5 to 4 h) and antibody levels which rapidly become undetectable (Huston, et al., (1996) *J. Nucl. Med.* 40: 320; Schier et al. (1995) *Immunotechnology*, 1: 73-81), while toxin levels presumably remain high (Hildebrand, et al. (1961) *Proc. Soc. Exp. Biol. Med.* 107-284-289). Performance of in vivo studies will be facilitated by the construction of complete IgG molecules from the $V_H$ and $V_L$ genes of scFv. Use of human constant regions will yield chimeric antibodies less immunogenic than murine monoclonals and much less immunogenic than currently used equine antitoxin. Immunogenicity can be further reduced by CDR grafting to yield humanized antibodies.

Example 2

Potent Neutralization of Botulinum Neurotoxin by Recombinant Oligoclonal Antibody The spore-forming bacteria *Clostridium botulinum* secrete botulinum neurotoxin (BoNT), the most poisonous substance known (Gill (1982) Microbiol. Rev. 46: 86-94). The protein toxin consists of a heavy and light chain that contain three functional domains (Simpson (1980) *J. Pharmacol. Exp. Ther.* 212: 16-21; Montecucco and Schiavo (1995) *Q. Rev. Biophys.* 28: 423-472; Lacy et al. (1998) *Nat. Struct. Biol.* 5: 898-902). The Cterminal portion of the heavy chain (Hc) comprises the binding domain, which binds to a sialoganglioside receptor and a putative protein receptor on presynaptic neurons, resulting in toxin endocytosis (Dolly et al. (1984) *Nature* (London) 307: 457-460; Montecucco (1986) *Trends Biochem. Sci.* 11: 315-317). The N-terminal portion of the heavy chain ($H_N$) comprises the translocation domain, which allows the toxin to escape the endosome. The light chain is a zinc endopeptidase that cleaves different members of the SNARE complex, depending on serotype, resulting in blockade of neuromuscular transmission (Schiavo et al. (1992) *Nature* (London) 359: 832-835; Schiavo et al. (1993) *J. Biol. Chem.* 268: 23784-23787).

There are seven BoNT serotypes (A-G; Lacy and Stevens (1999) J. Mol. Biol. 291: 1091-1104), four of which (A, B, E, and F) cause the human disease botulism (Amon et al. (2001) *J. Am. Med. Assoc.* 285: 1059-1070). Botulism is characterized by flaccid paralysis, which if not immediately fatal requires prolonged hospitalization in an intensive care unit and mechanical ventilation. The potent paralytic ability of the toxin has resulted in its use in low doses as a medicine to treat a range of overactive muscle conditions including cervical dystonias, cerebral palsy, posttraumatic brain injury, and poststroke spasticity (Mahant et al. (2000) *J. Clin. Neurosci.* 7: 389-394). BoNTs are also classified by the Centers for Disease Control (CDC) as one of the six highest-risk threat agents for bioterrorism (the "Class A agents"), because of their extreme potency and lethality, ease of production and transport, and need for prolonged intensive care (Amon et al. (2001) *J. Am. Med. Assoc.* 285: 1059-1070). Both Iraq and the former Soviet Union produced BoNT for use as weapons (United Nations Security Council (1995) *Tenth Report of the Executive Committee of the Special Commission Established by the Secretary-General Pursuant to Paragraph 9(b)(I) of Security Council Resolution 687 (1991), and Paragraph 3 of Resolution 699 (1991) on the Activities of the Special Commission* (United Nations Security Council, New York); Bozheyeva et al. (1999) *Former Soviet Biological Weapons Facilities in Kazakhstan: Past, Present, and Future* (Center for Nonproliferation Studies, Monterey Institute of International Studies, Monterey, Calif.)), and the Japanese cult Aum Shinrikyo attempted to use BoNT for bioterrorism (Amon et al. (2001) *J. Am. Med. Assoc.* 285: 1059-1070). As a result of these threats, specific pharmaceutical agents are needed for prevention and treatment of intoxication.

No specific small-molecule drugs exist for prevention or treatment of botulism, but an investigational pentavalent toxoid is available from the CDC (Siegel (1988) *J. Clin. Microbiol.* 26: 2351-2356) and a recombinant vaccine is under development (Byrne and Smith (2000) *Biochimie* 82: 955-966). Regardless, mass civilian or military vaccination is unlikely because of the rarity of disease or exposure and the fact that vaccination would prevent subsequent medicinal use of BoNT. Postexposure vaccination is useless because of the rapid onset of disease. Toxin neutralizing antibody (Ab) can be used for pre- or postexposure prophylaxis or for treatment (Franz et al. (1993) Pp. 473-476 in *Botulinum and Tetanus Neurotoxins Neurotransmission and Biomedical Aspects*, ed. DasGupta, B. R. Plenum, New York). Small quantities of both equine antitoxin and human botulinum immune globulin exist and are currently used to treat adult (Black and Gunn (1980) *Am. J. Med.* 69: 567-570; Hibbs et al. (1996) *Clin. Infect. Dis.* 23: 337-340) and infant botulism (Amon (1993) Pp. 477-482 in *Botulinum and Tetanus Neurotoxins: Neurotransmission and Biomedical Aspects*, ed. DasGupta, B. R. Plenum, New York), respectively. Recombinant monoclonal antibody (mAb) could provide an unlimited supply of antitoxin free of infectious disease risk and not requiring human donors for plasmapheresis. Such mAbs must be of high potency to provide an adequate number of doses at reasonable cost. In some instances, the potency of polyclonal Ab can be recapitulated in a single mAb (Lang et al. (1993) *J. Immunol.*

151: 466-472). In the case of BoNT, potent neutralizing mAbs have yet to be produced: single mAb neutralizing at most 10 to 100 times the 50% lethal dose ($LD_{50}$) of toxin in mice (Pless et al. (2001) *Infect. Immun.* 69: 570-574; Hallis et al. (1993) Pp. 433-436 In: *Botulinum and Tetanus Neurotoxins: Neurotransmission and Biomedical Aspects*, ed. DasGupta, B. R., Plenum, New York). In this example, we show that BoNT serotype A (BoNT/A) can be very potently neutralized in vitro and in vivo by combining two or three mAbs, providing a route to drugs for preventing and treating botulism and diseases caused by other pathogens and biologic threat agents.

Methods

IgG Construction.

$V_H$ genes of C25, S25, and 3D12 single-chain fragment variable (scFv) were amplified using PCR from the respective phagemid DNA with the primer pairs GTC TCC TGA GCT AGC TGA GGA GAC GGT GAC CGT GGT (SEQ ID NO:44) and either GTA CCA ACG CGT GTC TTG TCC CAG GTC CAG CTG CAG GAG TCT (C25, SEQ ID NO:45), GTA CCA ACG CGT GTC TTG TCC CAG GTC AAG CTG CAG CAG TCA (S25, SEQ ID NO:46), or GTA CCA ACG CGT GTC TTG TCC CAG GTG CAG CTG GTG CAG TCT (3D12, SEQ ID NO:47). DNA was digested with MluI and NheI, ligated into N5KG1Val- Lark (gift of Mitch Reff, IDEC Pharmaceuticals, San Diego) and clones containing the correct $V_H$ identified by DNA sequencing. V_genes of C25, S25, and 3D12 scFv were amplified from the respective phagemid DNA with the primer pairs TCA GTC GTT GCA TGT ACT CCA GGT GCA CGA TGT GAC ATC GAG CTC ACT CAG TCT (SEQ ID NO:48) and CTG GAA ATC AAA CGT ACG TTT TAT TTC CAG CTT GGT (C25, SEQ ID NO:49), TCA GTC GTT GCA TGT ACT CCA GGT GCA CGA TGT GAC ATC GAG CTC ACT CAG TCT (SEQ ID NO:50) and CTG GAA ATC AAA CGT ACG TTT GAT TTC CAG CTT GGT (S25, SEQ ID NO:51), or TCA GTC GTT GCA TGT ACT CCA GGT GCA CGA TGT GAC ATC GTG ATG ACC CAG TCT (SEQ ID NO:52) and CTG GAA ATC AAA CGT ACG TTT TAT CTC CAG CTT GGT (3D12, SEQ ID NO:53), cloned into pCR-TOPO (Invitrogen) and clones containing the correct V identified by DNA sequencing. V_genes were excised from pCR-TOPO with DraIII and BsiWI and ligated into DraIII- and BsiWI-digested N5KG1Val-Lark DNA containing the appropriate $V_H$ gene. Clones containing the correct $V_H$ and Vκ gene were identified by DNA sequencing, and vector DNA was used to transfect CHO DG44 cells by electroporation. Stable cell lines were established by selection in G418 and expanded into $H_c$ spinner flasks. Supernatant containing IgG was collected, concentrated by ultrafiltration, and purified on Protein G (Pharmacia).

Measurement of IgG Affinity and Binding Kinetics.

IgG binding kinetics were measured using surface plasmon resonance in a BIACORE™ (Pharmacia Biosensor) and used to calculate the $K_d$. Approximately 200-400 response units of purified IgG (10-20 μg/ml in 10 mM acetate, pH 3.5-4.5) was coupled to a CM5 sensor chip by using N-hydroxysuccinimide-N-ethyl-N'-(dimethylaminopropyl)-carbodiimide chemistry. The association rate constant for purified BoNT/$AH_c$ was measured under continuous flow of 15 μl/min, using a concentration range of 50-800 nM. The association rate constant ($k_{on}$) was determined from a plot of (ln(dR/dt))/t vs. concentration. The dissociation rate constant ($k_{off}$) was determined from the dissociation part of the sensorgram at the highest concentration of scFv analyzed using a flow rate of 30 μl/min to prevent rebinding. $K_d$ was calculated as $k_{off}/k_{on}$.

Measurement of in Vitro Toxin Neutralization.

Phrenic nervehemidiaphragm preparations were excised from male CD-1 mice (25-33 g) and suspended in 135 mM NaCl, 5 mM KCl, 1 mM $Na_2HPO_4$, 15 mM $NaHCO_3$, 1 mM $MgCl_2$, 2 mM $CaCl_2$, and 11 mM glucose. The incubation bath was bubbled with 95% $O_2$/5% $CO_2$ and maintained at 36° C. Phrenic nerves were stimulated at 0.05 Hz with square waves of 0.2 ms duration. Isometric twitch tension was measured using a force-displacement transducer (Model FT03, Grass Instruments, Quincy, Mass.). Purified IgG were incubated with BoNT A for 30 min at room temperature and then added to the tissue bath resulting in a final IgG concentration of $6.0\times10^{-8}$ M (S25 and 3D12 alone) or $2.0\times10^{-8}$M (C25 alone) and a final BoNT A concentration of $2.0\times10^{-11}$ M. For pairs of IgG, the final concentration of each IgG was decreased 50%, and for studies of a mixture of all 3 IgG, the concentration of each IgG was decreased by 67%.

Measurement of in Vivo Toxin Neutralization.

Fifty micrograms of the appropriate IgG were added to the indicated number of mouse $LD_{50}$ of BoNT/A neurotoxin (Hall strain) in a total volume of 0.5 ml of gelatin phosphate buffer and incubated at RT for 30 min For pairs of Ab, 25 μg of each Ab was added, and for the combination of 3 Ab, 16.7 μg of each Ab was added. The mixture was then injected i.p. into female CD-1 mice (16-22 g). Mice were studied in groups of ten and were observed at least daily. The final death tally was determined 5 days after injection.

Measurement of Solution Affinity of Mabs.

Equilibrium binding studies were conducted using a KinExA flow fluorimeter to quantify the antibodies with unoccupied binding sites in reaction mixtures of the antibody with the antigen. Studies with reaction mixtures comprised of one, two, or three different antibodies were conducted in Hepes-buffered saline, pH 7.4, with total antibody concentrations of 342, 17.2, and 17.2 pM, respectively. In all cases, the concentration of soluble toxin was varied from less than 0.1 to greater than 10-fold the value of the apparent $K_d$ (twelve concentrations, minimum). Reaction mixtures comprised of one, two, or three different antibodies were incubated at 25° C. for 0.5, 3, and 17 h, respectively, to ensure that equilibrium was achieved.

Results

To generate mAbs capable of neutralizing BoNT/A, we previously generated scFv phage antibody libraries from mice immunized with recombinant BoNT/A binding domain ($H_c$) and from humans immunized with pentavalent botulinum toxoid (Amersdorfer et al. (1997) Infect. Immun. 65: 3743-3752; Amersdorfer et al. (2002) Vaccine 20: 1640-1648). After screening more than 100 unique mAbs from these libraries, three groups of scFv were identified that bound nonoverlapping epitopes on BoNT/$AH_c$ and that neutralized toxin in vitro (prolonged the time to neuroparalysis in a murine hemidiaphragm model; Amersdorfer et al. (1997) Infect. Immun. 65: 3743-3752; Amersdorfer et al. (2002) Vaccine 20: 1640-1648). In vitro toxin neutralization increased significantly when two scFv binding nonoverlapping epitopes were combined. In vivo toxin neutralization could not be determined because of the rapid clearance of the 25-kDa scFv from serum (Colcher et al. (1990) *J. Natl. Cancer Inst.* 82: 1191-1197).

To evaluate in vivo BoNT neurotoxin neutralization, IgG were constructed from the $V_H$ and V_genes of three BoNT/A scFv that neutralized toxin in vitro. $V_H$ and Vκ genes were sequentially cloned into a mammalian expression vector, resulting in the fusion of the human Cκ gene to the Vκ and the human γ1 gene to the $V_H$. Stable expressing cell lines were established and IgG purified from supernatant yielding chimeric IgG with murine V– domains and human C-domains, for the murine scFv C25 and S25, and a fully human IgG for the human scFv 3D12. IgG equilibrium binding constants ($K_d$) were measured and found to be at least comparable to the binding constants of the scFv from which they were derived (Table 6). The antigen binding affinity of two of the IgG (S25 and 3D12) was significantly higher (lower $K_d$) than for the corresponding scFv, largely because of an increase in the association rate constant ($k_{on}$). We presume this reflects an increase in the stability of the molecule and hence an increase in the functional antibody concentration.

TABLE 6

Association ($k_{on}$) and dissociation ($k_{off}$) rate constants and equilibrium dissociation constants ($K_d$) for BoNT/A IgG and scFv from which the IgG were derived.

| Ab | IgG | | | scFv | | |
|---|---|---|---|---|---|---|
|  | $K_d$ | $k_{on}$ | $k_{off}$ | $K_d$ | $k_{on}$ | $k_{off}$ |
| C25 | $1.69 \times 10^{-9}$ | $1.32 \times 10^6$ | $2.24 \times 10^{-3}$ | $1.10 \times 10-9$ | $3.00 \times 10^5$ | $3.30 \times 10^{-4}$ |
| S25 | $3.90 \times 10^{-9}$ | $1.46 \times 10^6$ | $5.70 \times 10^{-3}$ | $7.30 \times 10-8$ | $1.10 \times 10^4$ | $8.10 \times 10^{-4}$ |
| 3D12 | $5.62 \times 10^{-11}$ | $2.26 \times 10^6$ | $1.27 \times 10^{-4}$ | $3.69 \times 10-8$ | $1.30 \times 10^4$ | $5.00 \times 10^{-4}$ |

Figure 4:
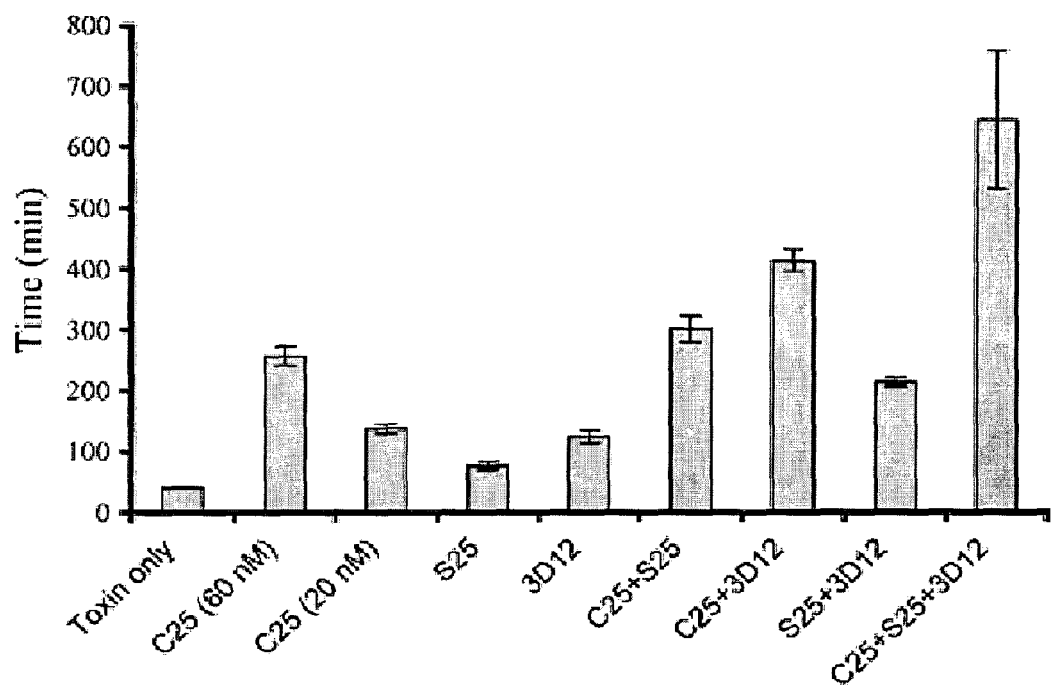
FIG. 4 shows in vitro toxin neutralization by mAb, pairs of mAbs, and oligoclonal Ab. Time to 50% twitch reduction was measured in isolated mouse hemidiaphragms and reported for toxin only control, single mAb (C25, S25, or 3D12), pairs of mAbs (C25 S25, C25+3D12, or 3D12+S25), and oligoclonal Ab (C25+3D12+S25). Single mAb significantly prolonged time to neuroparalysis compared with toxin only. Pairs of mAbs significantly prolonged time to neuroparalysis compared with single mAbs.

In vitro toxin neutralization by IgG was determined in the mouse hemidiaphragm assay (Desphande et al. (1995) *Toxicon* 33: 551-557). Compared with toxin alone, each of the three IgG significantly increased the time to neuroparalysis, with C25 being the most potent (FIG. 4). Significant synergy in toxin neutralization was observed when pairs of IgG were studied. For these studies, it was necessary to decrease the concentration of C25 IgG studied 3-fold to 20 nM because of its high potency and the fact that the hemidiaphragm preparations have an 8-h lifespan. Each pair of IgG significantly increased the time to neuroparalysis compared with the time for either single IgG (FIG. 4). A mixture of all three IgG further increased the time to neuroparalysis, although this difference did not reach statistical significance compared with antibody pairs because of the small number of diaphragms studied.

Figure 3:
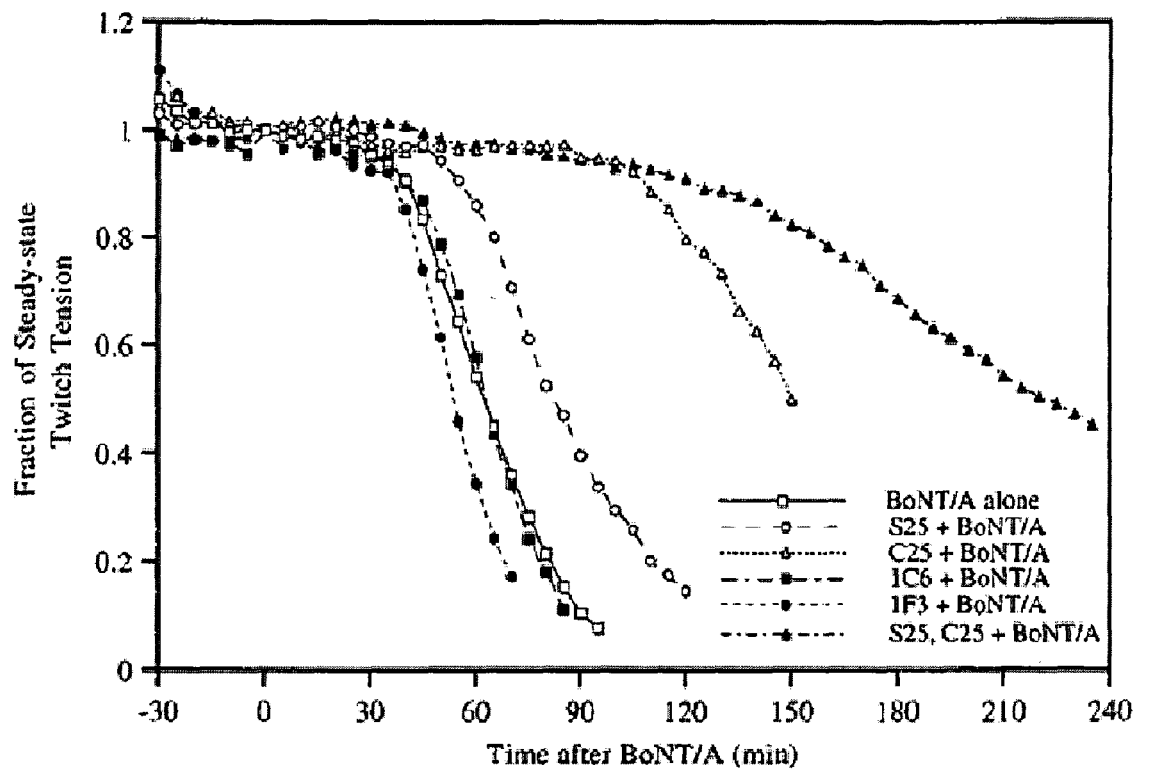
Figure 5A:
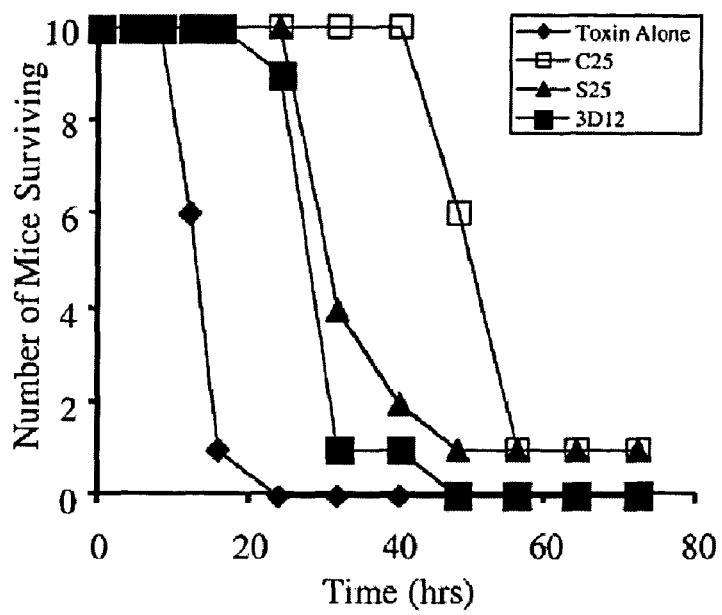
FIGS. 5A and 5B show in vivo toxin neutralization by mAbs (FIG. 5A) and pairs (FIG. 5B) of mAbs. Fifty micrograms total Ab was mixed with 20 or 100 mouse $LD_{50}$s of toxin and injected i.p. Time to death and number of surviving mice was determined. No single mAb showed significant protection against 20 $LD_{50}$s. All mice survived challenge with 100 $LD_{50}$s when given any pair of mAbs.
Figure 5B:
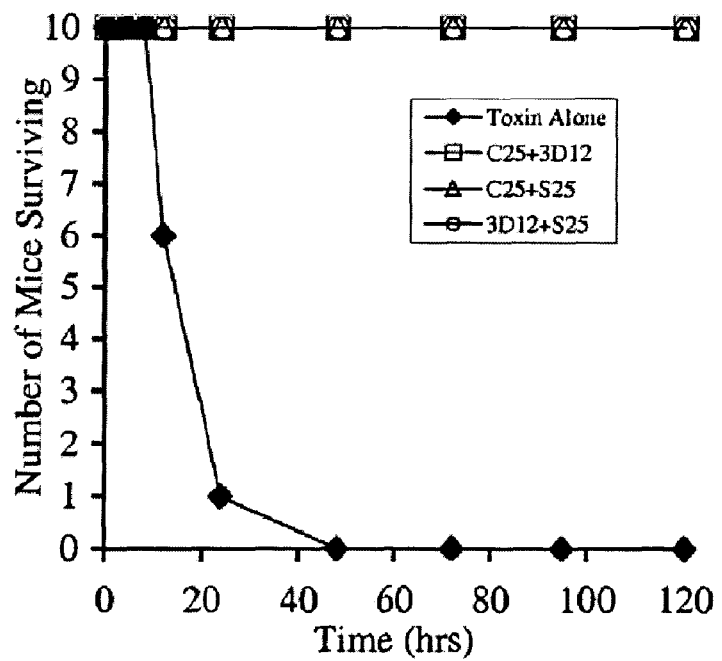
Figure 6:
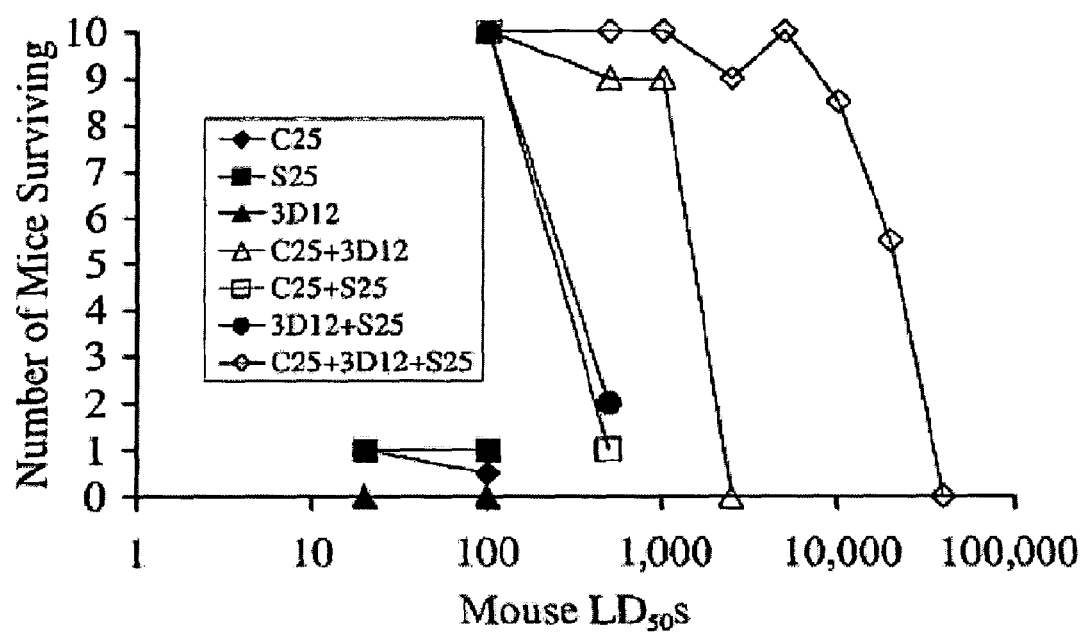
FIG. 6 shows in vivo toxin neutralization by mAbs, pairs of mAbs, and oligoclonal Ab. In vivo toxin neutralization was determined for mAbs, pairs of mAbs, and oligoclonal Ab at increasing toxin challenge doses. No single mAb showed significant protection. In contrast all mAb pairs neutralized at least 100 $LD_{50}$s, with approximately 50% of mice surviving challenge with 1,500 $LD_{50}$s of toxin for the most potent pair (C25+3D12). Oligoclonal Ab was even more potent with approximately 50% of mice surviving challenge with 20,000 $LD_{50}$s of toxin.
Figure 9A:
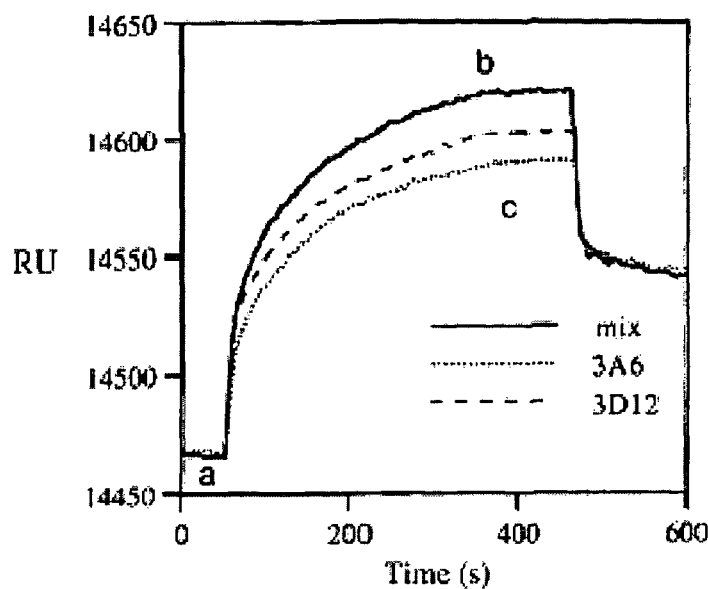
FIGS. 9A and 9B show sensorgrams of epitope mapping of scFv binding to BoNT/A $H_C$. Point 'a': beginning of injection, point 'b': end of injection, and point 'c': amount of scFv bound. The difference in RU between points b and c is due to differences in refractive index between scFv and running buffer.
Figure 9B:
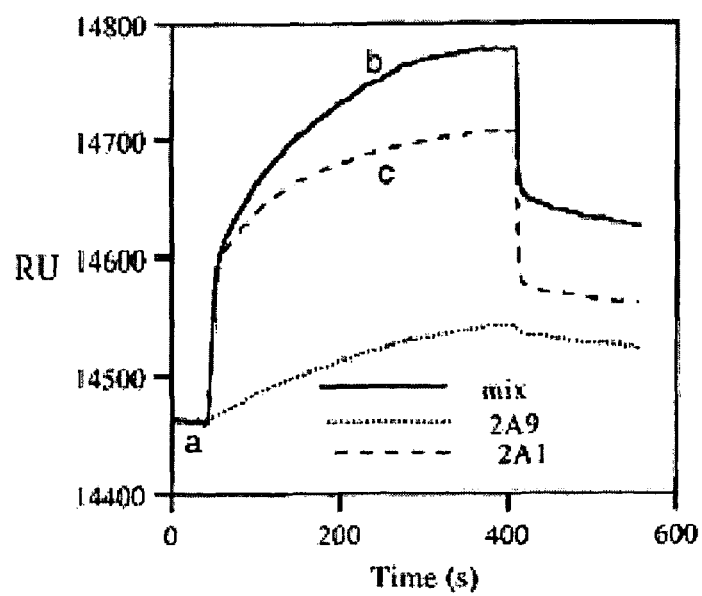
Figure 10A:
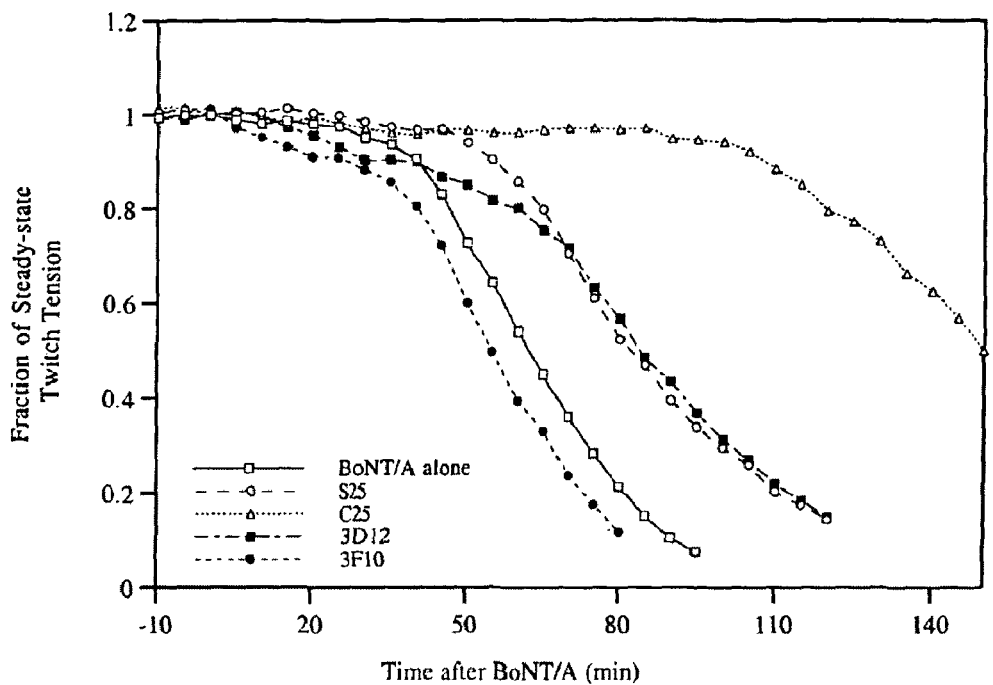
FIGS. 10A and 10B show the individual and combined effects of scFv antibodies targeting BoNT/A HC domain.
Figure 10B:
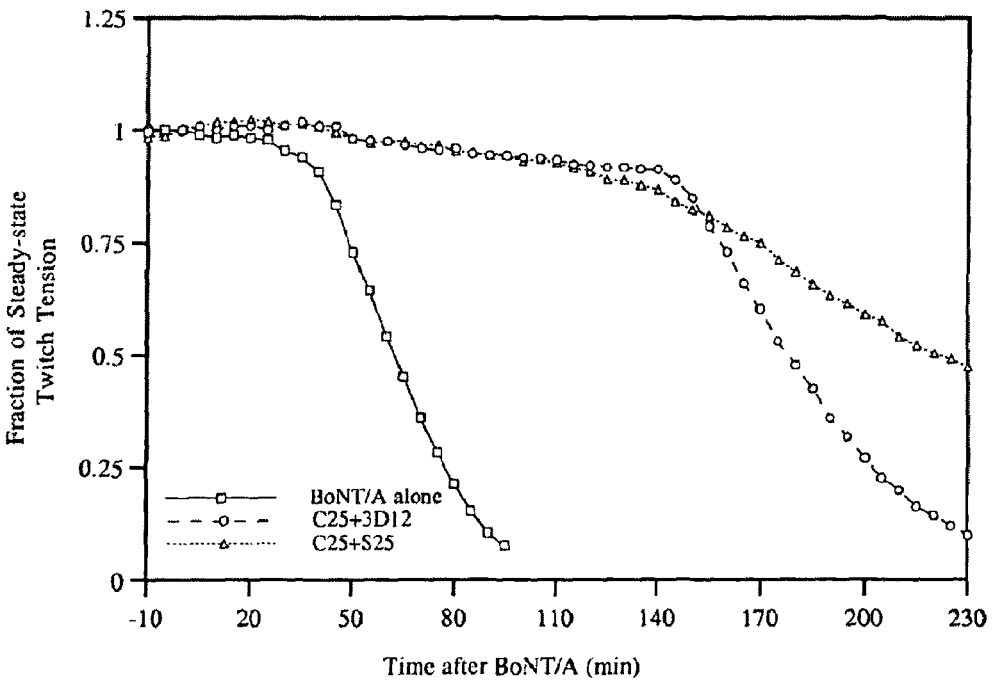

In vivo toxin neutralization was studied using a mouse assay in which toxin and Ab are premixed and injected i.p., and time to death and number of surviving mice determined (Sheridan et al. (2001) *Toxicon* 39: 651-657). Fifty micrograms of each single mAb prolonged the time to death but failed to protect mice challenged with 20 $LD_{50}$s (FIG. 5A). In contrast, any pair of mAbs completely protected mice challenged with 100 $LD_{50}$s of toxin (FIG. 5B). At 500 $LD_{50}$s, the majority of mice receiving two of the pairs of mAbs (S25+3D12 or C25+S25) died, whereas 80% of mice receiving the pair of C25+3D12 survived (FIG. 3). All mice receiving a mixture of all three mAbs (oligoclonal Ab) survived challenge with 500 $LD_{50}$s of toxin (FIG. 6). In these studies, the total amount of Ab administered was kept constant at 50 µg per mouse. To determine potency, mAb pairs and oligoclonal Ab were studied at increasing doses of toxin (FIG. 6). The most potent mAb pair (C25+3D12) protected 90% of mice challenged with 1,000 $LD_{50}$s, with no mice surviving challenge with 2,500 $LD_{50}$s. In contrast, oligoclonal Ab completely protected all mice challenged with 5,000 $LD_{50}$s of toxin, with five of ten mice surviving challenge with 20,000 $LD_{50}$s of toxin. The potency of the oligoclonal Ab was titrated using a modification of the standard mouse neutralization bioassay (Hatheway and Dang (1994) Pp. 93-107 In: *Therapy with Botulinum Toxin*, ed. Jankovic, J., Dekker, New York) and was determined to be 45 international units (IU)/mg of Ab, 90 times more potent than the human botulinum immune globulin used to treat infant botulism (Amon (1993) Pp. 477-482 in *Botulinum and Tetanus Neurotoxins: Neurotransmission and Biomedical Aspects*, ed. DasGupta, B. R. Plenum, New York). By definition, one IU neutralizes 10,000 $LD50$s of $BoNT\_A$ toxin (Bowmer (1963) *Bull. W. H. O.* 29: 701-709).

Two potential mechanisms could account for the increase in potency observed when mAbs were combined: an increase in the functional binding affinity of the Ab mixture for toxin and/or an increase in the blockade of the toxin surface that binds to cellular receptor(s). To determine the effect of combining antibodies on the functional binding affinities, apparent $K_d$ were determined for each single mAb, pairs of mAbs, and the mixture of all three mAbs by using a flow fluorimeter to quantify the free antibody that remained in solution reaction mixtures. For single mAbs, the antigen binding affinities measured in homogeneous solution (both antigen and antibody in solution; FIG. 7) were lower (higher $K_d$) than those measured by surface plasmon resonance in a BIACORE™ (Table 6), where the antibody is immobilized and only the antigen is in solution. When antibody C25, which showed the greatest in vitro potency, was mixed in equimolar amounts with antibody 3D12, the resulting Ab combination bound to the toxin with an apparent $K_d$ of 65 µM, an affinity 200- and 10-fold higher (lower $K_d$) than those observed with the individual antibodies alone. Addition of equimolar amounts of a third mAb (S25) to the mixture increased the apparent affinity further to 18 pM. An equimolar mixture of C25 with S25 yielded only a minor 2-fold increase in affinity, which may explain why this pair is less potent in vivo than the combination of C25 and 3D12. The increase in functional affinity observed with multiple mAbs may be due to either a conformational change in toxin that occurs on binding of the first mAb, resulting in higher affinity binding of the second and third mAbs, or from mAb binding changing the toxin from a monovalent to a multivalent antigen (Moyle et al. (1983) *J. Immunol.* 131: 1900-1905). This results in an "avidity effect" and an increase in affinity. Avidity effects have been well recognized and characterized for IgG binding to multivalent antigens (Crothers and Metzger (1972) *Immunochemistry* 9: 341-357), such as cell surfaces, but are not well appreciated as occurring in solution.

The increments in measured $K_d$ are consistent with the increase in in vivo potency observed for mAb pairs and oligoclonal Ab. Rearranging the equilibrium binding equation:

$$\text{free toxin/bound toxin} = K_d / [\text{serum antibody}].$$

Assuming a 2-ml mouse blood volume, the serum antibody concentration is 160 nM when mice receive 50 µg of Ab. Because the administered amount of toxin is a large multiple of the $LD_{50}$, bound toxin~administered toxin. Thus, the above equation simplifies to:

$$\text{free toxin/administered toxin} = K_d / 160 \text{ nM}.$$

To determine the amount of administered toxin that results in death of 50% of mice, one substitutes 1 $LD_{50}$ for the amount of free toxin and solves for administered toxin, yielding the equation:

administered toxin (in $LD_{50}$s)=1 $LD_{50} \times 160$ nM/$K_d$.

Using the solution Kd for C25, the predicted toxin dose at which 50% of the mice survive is 16 $LD_{50}$s (administered toxin=1 $LD_{50} \times 160$ nM/10 nM). When this calculation is applied to the C25 and 3D12 Ab pair, and to oligoclonal Ab, the magnitude of the increase in potency on combining antibodies parallels the increase in functional affinity (Table 7).

TABLE 7

Observed and predicted toxin neutralization by rewcombinant antibody.

| Antibody | Predicted Toxin Neutralization | Observed Toxin Neutralization |
| --- | --- | --- |
| C25 | 16 $LD_{50}$s | <20 $LD_{50}$s |
| C25 + 3D12 | 2,500 $LD_{50}$s | 1,500 $LD_{50}$s |
| C25 + 3D12 + S25 | 8,900 $LD_{50}$s | 20,000 $LD_{50}$s |

The second potential mechanism for potent toxin neutralization by oligoclonal Ab is the need to block multiple epitopes on the toxin binding domain surface that bind to cellular receptors. It has been hypothesized that the toxin binds to cellular receptors via at least two sites on the toxin binding domain (Dolly et al. (1984) Nature (London) 307: 457-460; Montecucco (1986) Trends Biochem. Sci. 11: 315-317). These include a ganglioside binding site and a putative protein receptor binding site. In fact, two spatially separated ganglioside binding sites have been observed in the co-crystal structure of the homologous tetanus toxin (Fotinou et al. (2001) J. Biol. Chem. 276: 32274-32281), and mAbs binding nonoverlapping tetanus toxin epitopes can block binding of toxin to GT1b ganglioside (Fitzsimmons et al. (2000) Vaccine 19: 114-121). Our prior epitope mapping studies are consistent with multiple mAbs blocking a large portion of the BoNT binding domain (HC) (Mullaney et al. (2001) Infect. Immun. 69: 6511-6514). Two of the mAbs (S25 and 3D12) bind the C-terminal subdomain of BoNT HC. The C25 mAb binds a conformational epitope that consists of sequence from the N- and C-terminal subdomains of BoNT $H_C$. One model consistent with the epitope mapping places the three mAb epitopes on the same $H_C$ face and overlapping the known docking sites for the putative cellular ganglioside receptor GT1b (Mullaney et al. (2001) Infect. Immun. 69: 6511-6514).

Discussion

In conclusion, we have shown that one of the six class A biowarfare agents, BoNT/A, can be potently neutralized by an oligoclonal Ab consisting of only three mAbs. Oligoclonal Ab is 90 times more potent than hyperimmune human globulin and approaches the potency of hyperimmune mono-serotype horse type A antitoxin (Sheridan et al. (2001) Toxicon 39: 651-657). Thus, the potency of polyclonal serum can be deconvoluted, or reduced, to mAbs binding only three nonoverlapping epitopes. This synergistic effect results in a more than 20,000-fold increase in potency for the three mAbs compared with the potency of any of the single mAbs. Others have previously shown synergy between monoclonal antibodies in neutralizing tetanus toxin or HIV infection. In the case of tetanus toxin, combining three to four monoclonal antibodies increased the potency of in vivo toxin neutralization up to 200-fold (Volk et al. (1984) Infect. Immun. 45: 604-609). In the case of HIV, combining three or four mAbs increased the potency of viral neutralization 10-fold compared with individual mAbs (Zwick et al. (2001) J. Virol. 75: 12198-12208). Thus, our observation is likely to prove general in many systems. We show, however, that the increased potency in the case of toxin neutralization likely results from a large increase in the functional affinity of the mixture antibodies. Whether such a mechanism holds true for viral neutralization is unclear.

One can hypothesize that the polyclonal humoral immune response to toxin is functionally dominated by Ab binding only a few nonoverlapping epitopes. The increase in potency appears to result primarily from a large decrease in the $K_d$ of oligoclonal Ab compared with the individual mAb, and also to greater blockade of the toxin surface that interacts with cellular receptors. Such mechanisms may be generally applicable to many antigens in solution, suggesting that oligoclonal Ab may offer a general route to more potent antigen neutralization than mAb. Although it might be possible to achieve a similar potency by engineering the $K_d$ of the C25 mAb to near pM, oligoclonal Ab offers a simpler, more rapid route to a potent antitoxin.

Oligoclonal Ab also offers a safe and unlimited supply of drug for prevention and treatment of BoNT/A intoxication. Because the Ab consists of either chimeric or human IgG, production could be immediately scaled to produce a stockpile of safe antitoxin. Alternatively, we have already replaced the chimeric S25 IgG with a fully human IgG and increased potency of the oligoclonal Ab more than 2-fold. Work is ongoing to replace chimeric C25 with a fully human homologue. Chimeric, humanized, and human mAb represent an increasingly important class of therapeutic agents whose means of production are known. Ten mAbs have been approved by the FDA for human therapy and more then 70 other mAb therapeutics are in clinical trials (Reichert (2001) Nat. Biotechnol. 19: 819-822). With an elimination half-life of up to 4 weeks, Ab could provide months of protection against toxin or be used for treatment. Oligoclonal Ab would be applicable to the other BoNT toxin serotypes, as well as to other class A agents. Anthrax is a toxin-mediated disease, and Ab has been shown to be protective for this agent (Little et al. (1997) Infect. Immun. 65: 5171-5175; Beedham et al. (2001) Vaccine 19: 4409-4416). Vaccinia immune globulin can be used to prevent or treat smallpox or complications arising from vaccination of immunocompromised hosts (Feery (1976) Vox Sang. 31: 68-76). Ab may also be useful for plague and disease caused by the hemorrhagic fever viruses (Hill et al. (1997) Infect. immun. 65: 4476-4482; Wilson et al. (2000) Science 287: 1664-1666). Our data support the rapid development and evaluation of oligoclonal Ab for countering BoNT and other agents of biowarfare and bioterrorism.

Example 3

Genetic and Immunological Comparison of Anti-Botulinum Type A Antibodies from Immune and Non-Immune Human Phage Libraries Understanding the antibody response in botulinum intoxication is important for vaccine design and passive prophylaxis. To investigate this activity, we have studied the immune response to BoNT/A (botulinum neurotoxin serotype A) binding domain ($H_C$) at the molecular level using phage display. The scFv antibodies were isolated from V-gene repertoires prepared from (a) human volunteer immunized with pentavalent botulinum toxoid and (b) non-immune human peripheral blood lymphocytes and spleenocytes. A large panel of serotype specific phage expressing botulinum binding scFv could be selected from both libraries. Epitope mapping of immune scFv binders towards BoNT/A HC revealed surprisingly a limited number of scFv recognizing conformational epitopes that corresponded to two distinct groups, clusters I and II. Only scFv from cluster I exhibited neutralizing activity in the mouse hemidiaphragm assay. Anti-BoNT/A HC clones derived from a non-immune library could be conveniently grouped into clusters III-XI and appeared to share no overlapping epitopes with cluster I or II. In addition they showed no neutralization of toxin at biologically significant concentrations. We therefore suggest that a vaccine based on the pentavalent botulinum toxoid directs the humoral immune response to a limited number of immunodominant epitopes exposed on the binding domain HC.

Introduction

Botulinum toxin is a paralytic neurotoxin existing as seven different serotypes (A-G) elaborated by a number of bacterial species belonging to the genus *Clostridium* (Hatheway (1989) Pp. 3-24 In: Simpson LL, editor. Botulinum neurotoxin and tetanus toxin. San Diego Academic Press). They are produced as a single chain protein ($M_r$: 150,000) and fully activated by limited proteolysis, which results in formation of two chains, the heavy ($M_r$: 100,000) and light ($M_r$: 50,000) chains held together by a disulfide bond and non-covalent bonds (Niemann (1991) Pp. 303-348 In: Alouf J E, Freer J H, editors. Sourcebook of bacterial protein toxins. New York: Academic Press; Simpson (1990) *J. Physiol.*, 84:143-151). Poisoning can occur by ingestion of clostridia-contaminated food (foodborne botulism), by infant bowel infection (infant botulism), and by deep subcutaneous infection of wounds (wound botulism). Human botulism is most frequently caused by types A, B, and E and rarely by F (Dowell (1984) *Rev Infect Dis.*, 6(Suppl 1):202-207; Botulism in the United States. Handbook for epidemiologists, clinicians and laboratory workers. Atlanta, Center for Disease Control, 1980). BoNTs (botulinum neurotoxin serotypes) act preferentially on cholinergic nerve endings to block acetylcholine release (Habermann et al. (1986) *Curr Top Microbiol Immunol.*, 129: 93-179; Montecuccoet al. (1994) *Mol. Microbiol.*, 13:1-8). The action of BoNTs involves three steps (Simpson (1986) *Ann Rev Pharmacol Toxicol.*, 26:427-453): (1) binding to receptors on the presynaptic membranes via the C-terminus of the heavy chain Hc; (2) translocation of the light chain into the cytosol via the N-terminus of the heavy chain HN; and (3) cleavage of one or more key components in the synaptic vesicle docking and fusion protein complex by the zinc protease activity of the light chain (Montecuccoet al. (1994) Mol Microbiol., 13:1-8; Schiavo (1992) *J Biol. Chem.*, 267: 23479-23483; Schiavoet al. (1995) *Curr Top Microbiol Immun.*, 195:257-275). Passive immunotherapy has been established as a valuable prophylactic and therapeutic approach against human pathogens and their toxins (for review, see Gronskiet al. (1990) *Mol. Immunol.*, 28:1321-1332 and Cross (1997) P. 97 In: Cryz S J, editor. Immunotherapy and vaccines. Weinheim, Germany: VCH Verlagsgesellschaft). In the case of botulism it is believed that antibody preparations recognizing the C-terminal domain of the BoNT heavy chain (HC) are able to prevent binding of the toxin to its cellular receptor(s). Immunization of mice with recombinant HC conferred good protection in vivo to a challenge dose up to 1,000,000 mouse i.p. $LD_{50}$ (Clayton et al. (1995) *Infect Immun.*, 63:2738-2742; Byrneet al. (1998) *Infect Immun.*, 66:10). Equine plasma-derived polyclonal anti-botulinum antibody preparations (equine HIG) have been administered to more than 80% of adult botulism patients in the past (Middlebrook and Brown (1995) *Curr Top Microbiol Immun.*, 195:89-122; Tacket et al. (1984) *Am J Med.*, 76:794-798; Morris (1981) P. 15 In: Lewis G E jr, editor. Biomedical aspects of botulism. New York: Academic Press). The large number of different epitopes recognized by polyclonal antibody preparations normally ensures the presence of protective antibodies, which are usually a small subpopulation of the total antibody. For prophylaxis, equine antibody is most effective when administered prior to exposure, but can prevent the disease up to 24 h post exposure (Middlebrook and Brown (1995) *Curr Top Microbiol Immun.*, 195:89-122). However, administration of equine antitoxin can cause adverse reactions, such as serum sickness and anaphylaxis in 9% of cases (Black and Gunn (1980) *Am J. Med.*, 69:567-570). Recent efforts have been focused on the production of human immunoglobulin (human BIG) prepared from serum of immunized volunteer donors (Amon (1993) Pp. 477-482 In: DasGupta B R, editor. Botulinum and tetanus neurotoxins, neurotransmission and biomedical aspects. New York: Plenum Press). Neutralizing monoclonal antibodies, especially if of human origin, would provide an unlimited source of antibody and replace the preparation of antibody from humans or horses.

We have been using antibody phage display to generate monoclonal antibodies capable of neutralizing BoNTs (Hoogenboom et al. (1991) *Nucl Acids Res.*, 19:4133-4137; McCaffertyet al. (1990) *Nature*, 348:552-554; Skerra and Pluckthun (1988) *Science*, 240:1038-1041). Using phage antibody libraries constructed from immunized mice, we identified two sets of monoclonal which bound two non-overlapping neutralizing epitopes on BoNT/A Hc (Amersdorfer et al. (1997) *Infect. Immun.*, 65:3743-3752). In the present example, we describe the characterization of monoclonal antibodies selected from a phage antibody library constructed from a human volunteer immunized with pentavalent botulinum toxoid (A-E). The affinities and epitopes recognized by these monoclonal antibodies were compared to affinities and epitopes recognized by monoclonal antibodies selected from a non-immune human phage library. The results identify an additional neutralizing epitope and provide a path to generating a fully human antibody for botulism prevention and treatment.

Materials and Methods:

Immune and Non-Immune V-Gene Antibody Libraries

For construction of an immune phage antibody library, a human volunteer received immunization with pentavalent botulinum toxoid types A-E (Michigan Department of Public Health). The volunteer was immunized at 0, 2 and 12 weeks with 0.5 ml of pentavalent toxoid and boosted with 0.5 ml of toxoid 1 year later. The neutralization titer against BoNT/A was measured using the mouse serum neutralization bioassay (Hathewayet al. (1984) *J Infect Dis.*, 150: 407-412). PBLs were isolated by centrifugation in Histopaque 1077 and RNA prepared using a modified method of Cathala et al. (Cathala et al. (1983) *DNA*, 2:329-335). First strand cDNA was made from RNA prepared from $1.0 \times 10^8$ B cells, using an IgG constant region primer for heavy chain or κ and λ constant region primers for light chains [26]. $V_H$, $V_\kappa$ and $V_\lambda$ genes were amplified from first strand cDNA as described (Markset al. (1991) *J Mol. Biol.*, 222:581-597). PCR products were gel purified, ethanol precipitated after extraction from the gel and used to construct scFv gene repertoires as previously described (Id.). The scFv gene repertoires were gel purified and then used as template for re-amplification with flanking oligonucleotides containing appended restriction sites (Id.). scFv gene repertoires ($V_H$–$V_\kappa$, $V_H$–$V_\lambda$) were gel purified, digested with SfiI and NotI, extracted with phenol/chloroform, and ligated into the vector pCANTAB-5E (Pharmacia Biotech, Milwaukee, Wis.) digested with SfiI and NotI (Sambrooket al. (1991) New York: Cold Spring Harbor Laboratory). The ligation mix was extracted with phenol/chloroform, ethanol precipitated, and electroporated into 50 µl *E. coli* TG1 cells (Gibson(1984) University of Cambridge: studies on the Epstein-Barr virus genome). Cells were plated on TYE plates containing 100 µg/ml ampicillin and 1% (w/v) glucose. Colonies were scraped off the plates into 2 ml 2×TY containing 100 µg/ml ampicillin, 1% (w/v) glucose and 15% (v/v) glycerol for storage at −70° C. The products from four transformations resulted in a library of $7.7 \times 10^5$ individual recombinants. For the non-immune library, a previously reported phage-displayed human single chain antibody library containing $6.7 \times 10^9$ members was utilized (Sheets et al. (1997) *Proc Natl. Acad Sci USA*, 95:6157-6162).

Phage Preparation and Selections

Phagemid particles from both libraries were prepared by rescue with VCS-M13 helper phage (Stratagene) as previously described (Markset al. (1991) *J Mol. Biol.*, 222:581-597). Phage particles were purified and concentrated by two PEG precipitations (Sambrooket al. (1991) New York: Cold Spring Harbor Laboratory), resuspended in 2 ml phosphate-buffered saline (PBS: 25 mM $NaH_2PO_4$, 125 mM NaCl, pH 7.4) and filtered through a 0.45 µm filter (Nalgene) to achieve a titer of approximately $10^{13}$ transducing units (TU)/ml.

Libraries were selected using 75 mm×12 mm immunotubes (Nunc, Maxisorb) coated overnight at 4° C. with 2 ml of BoNT serotypes A, B, C, and E (50 µg/ml each), or BoNT/A HC (50 µg/ml) in PBS, pH 7.4 (Emanuel et al. (1996) *J Immunol Meth.*, 193:189-97). Tubes were blocked with 2% skimmed milk powder in PBS for 1 h at RT, and then the selection, washing and elution procedures were performed as previously described (Markset al. (1991) *J Mol. Biol.*, 222: 581-597) using phage at a concentration of $5.0 \times 10^{12}$ TU/ml. The 500 µl of the eluted phage were used to infect 10 ml log phase growing *E. coli* TG1, which were plated on 2×TY-AMP-Glu plates. Phage were rescued, concentrated as described above, and used for the next selection round. The rescue-selection-plating cycle was typically repeated for four rounds.

ELISA Screening and Fingerprinting

After each round of selection, single ampicillin-resistant colonies were used to inoculate microtitre plate wells containing 150 µl of 2×TY-AMP-0.1% glucose. The bacteria were grown to give an A600 of approximately 0.9, and scFv expression induced by addition of isopropyl-β-d-thiogalacto-pyranoside (IPTG) to a final concentration of 1 mM (De Bellis and Schwartz (1990) *Nucl Acids Res.*, 18:1311). Bacteria were grown overnight with shaking at 25° C., the cells were pelleted by centrifugation, and the supernatant containing soluble scFv was collected. Screening of scFv for binding to BoNTs and BoNT/A HC was performed in 96-well microtitre plates (Falcon 3912) coated with 10 µg/ml of antigen in PBS, pH 7.4. The scFv derived from the non-immune library were detected using mouse monoclonal antibody 9E10 (1 µg/ml) (Santa Cruz Biotechnology, Calif.), which recognizes the C-terminal myc tag (Munro and Pelham (1986) Cell, 46:291-300) followed by peroxidase-conjugated anti-mouse Fc antibody (Sigma) as described (Griffiths and Malmqvist (1993) *EMBO J.*, 12:725-734). The scFvs derived from the immune library were detected using peroxidase-conjugated monoclonal antibody anti-E (2.5 µg/ml) (Pharmacia Biotech). The reaction was stopped after 30 min with NaF (3.2 mg/ml) and A405 nm was measured. The number of unique clones was determined by PCR-fingerprinting (Markset al. (1991) *J Mol Biol.*, 222:581-597) followed by DNA sequencing of the $V_H$ and $V_L$ genes of at least two clones from each fingerprint pattern. The specificity of antibodies was determined by ELISA performed as above using wells coated with 10 µg/ml of BoNT/A, BoNT/B, BoNT/C, BoNT/E, BoNT/A $H_C$ and recombinant translocation domain of serotype A (BoNT/A HN). Clones were identified as being specific for the selected antigen if they gave at least a five-fold higher signal than background.

Subcloning, Expression and Purification of scFv scFv antibodies binding BoNT/A and BoNT/A Hc as determined by ELISA were subcloned into the expression vector pUC119 Sfi-NotmycHis, resulting in the fusion of a hexa-histidine tag at the C-terminus of the scFv (Schieret al. (1995) *Immunotech.*, 1:73-81). The scFv was expressed and purified by immobilized metal affinity chromatography as previously described (Schieret al. (1996) *J Mol. Biol.*, 255: 28-43) and the concentration of purified monomeric scFv determined spectrophotometrically, assuming an $A_{280\ nm}$ of 1.0 correlates to an scFv concentration of 0.7 mg/ml.

Epitope Mapping and Affinity Determination

Epitope mapping and kinetic studies were performed using surface plasmon resonance in a BIACORE™ (Pharmacia Biosensor). In a BIACORE™ flow cell, approximately 600 resonance units (RU) of BoNT/A Hc (15 µg/ml in 10 mM sodium acetate, pH 4.5) were coupled to a CM5 sensor chip using NHS-EDC chemistry (Johnson et al. (1991) *Anal Biochem.*, 198:268-277). This amount of coupled BoNT/A Hc resulted in scFv RUmax of 100-175RU. The surface was regenerated after binding of scFv using 4M $MgCl_2$. For epitope mapping studies, the amount (RU) of scFv bound for each member of a pair was determined, and then the two scFv were mixed together to give a final concentration equal to the concentration used for measurements of the individual scFv (Amersdorfer et al. (1997) *Infect. Immun.*, 65:3743-3752). The Kd of scFv was calculated from the association rate constants ($k_{on}$) and dissociation rate constants ($k_{off}$) determined in the BIACORE™ ($K_d = k_{off}/k_{on}$). Association was measured under continuous flow of 5 µl/min using a concentration range of scFv from 50 to 1000 nM. The $k_{on}$ was determined from a plot of 1n (dR/dt)/t versus concentration (Karlsson et al. (1991) *J Immunol Meth.*, 145:229-240). The $k_{off}$ was determined from the dissociation part of the sensor-gram at the highest concentration of scFv analyzed using a flow rate of 30 µl/min to prevent rebinding.

In Vitro Bioassay

In vitro neutralization studies were performed using a mouse hemidiaphragm preparation, as previously described (Desphande(1995) *Toxicon*, 33:551-557). Phrenic nerve-hemidiaphragm preparations were excised from male CD/1 mice (25-33 g) and suspended in 135 mM NaCl, 5 mM KCl, 1 mM $Na_2PO_4$ 15 mM $NaHCO_3$ 1 mM $MgCl_2$ 2 mM $CaCl_2$, and 11 mM glucose. The incubation bath was bubbled with 95% $O_2$, 5% CO and maintained at 36° C. Phrenic nerves were stimulated at 0.05 Hz with square waves of 0.2 ms duration. Isometric twitch tension was measured using a force-displacement transducer (Model FT03, Grass) connected to a chart recorder. Purified scFv antibodies were incubated with BoNT/A for 30 min at RT and then added to the tissue bath resulting in a final scFv concentration of $2.0 \times 10^{-8}$M and a final BoNT/A concentration of $2.0 \times 10^{-11}$M. Toxin induced paralysis was defined as a 50% reduction of the initial muscle twitch. The ratio of prolongation was calculated from the value of 50% reduction by the antibody divided by 50% reduction of BoNT/A. The combination of 3D12 and C25 was studied at a final concentration of $2.0 \times 10^{-8}$ M each. Differences between times to 50% twitch reduction were determined using two-tailed t-test, with P<0.05 being significant.

Preparation of Botulinum Toxin and Botulinum Toxin Domains

Purified botulinum toxin serotype A, B, C and E (150 kDa) were obtained from USAMRIID. The binding domain of botulinum toxin type A (BoNT/A Hc) was expressed in *E. coli* and purified by immobilized metal affinity chromatography (IMAC) utilizing a C-terminal ($His_6$) tag (Ophidian Pharmaceuticals, Inc.). The translocation domain of botulinum toxin type A (BoNT/A HN) was a gift from Dr. R. Stevens (UC-Berkeley, Calif.).

TABLE 8

Specificity of BoNT binding scFv selected from immune and non-immune phage display libraries

| scFv specificity | Number of unique scFv | |
|---|---|---|
| | Immune Library (pentavalent toxoid) | Non-Immune Library |
| BoNT/A | 23 | 14 |
| HC (binding domain) | 6 | 10 |
| HN (translocation domain) | 4 | 1 |
| Light chain (cat. domain) | 13 | 3 |
| BoNT/B | 16 | 5 |
| BoNT/C | 6 | 5 |
| BoNT/E | 3 | 3 |

Results

Strategy for the Synthesis of Immune Phage Display Library

PBLs from a human volunteer immunized with pentavalent botulinum toxoid were used to generate a scFv phage antibody library. The donors polyclonal serum was protective against BoNT/A with a titer of 2.56 IU (international units) in the mouse neutralization bioassay (Hathewayet al. (1984) *J Infect Dis.*, 150: 407-412). The $V_H$ and $V_L$ genes were amplified from RNA, spliced together to create scFv gene repertoires and cloned into pCANTAB-5E to create a phage antibody library of $7.7 \times 10^5$ transformants. PCR screening of 15 randomly selected clones indicated that all carried full length inserts, 66% having Vκ light chains and 34% having $V_\lambda$ light chains as determined by germline gene specific light chain primers (data not shown).

Selection of Phage Antibody Libraries and ELISA Screening

Both the immune library and a large non-immune human phage antibody library (Sheets et al. (1997) *Proc Natl. Acad Sci USA*, 95:6157-6162) were selected on BoNT serotypes A, B, C, E and BoNT/A Hc. After three rounds of selection on BoNT/A or BoNT/A Hc, the frequency of ELISA positive clones was 79 and 100%, respectively from the immune library. A similar frequency of ELISA positivity was observed for the other serotypes. After three rounds of selection on BoNT/A or BoNT/A Hc, the frequency of ELISA positive clones was 28 and 94%, respectively from the non-immune library. A similar frequency of ELISA positivity was observed for the other serotypes. The number of unique scFv was determined by DNA fingerprinting followed by DNA sequencing, and specificity of each scFv was determined by ELISA. In screening, 100 colonies from each selection, 48 unique antibodies were identified from the immune library (23 BoNT/A, 16 BoNT/B, 6 BoNT/C and 3 BoNT/E) and 27 unique antibodies from the non-immune library (14 BoNT/A, 5 BoNT/B, 5 BoNT/C and 3 BoNT/E) (Table 8).

Figures 8A, 8B:
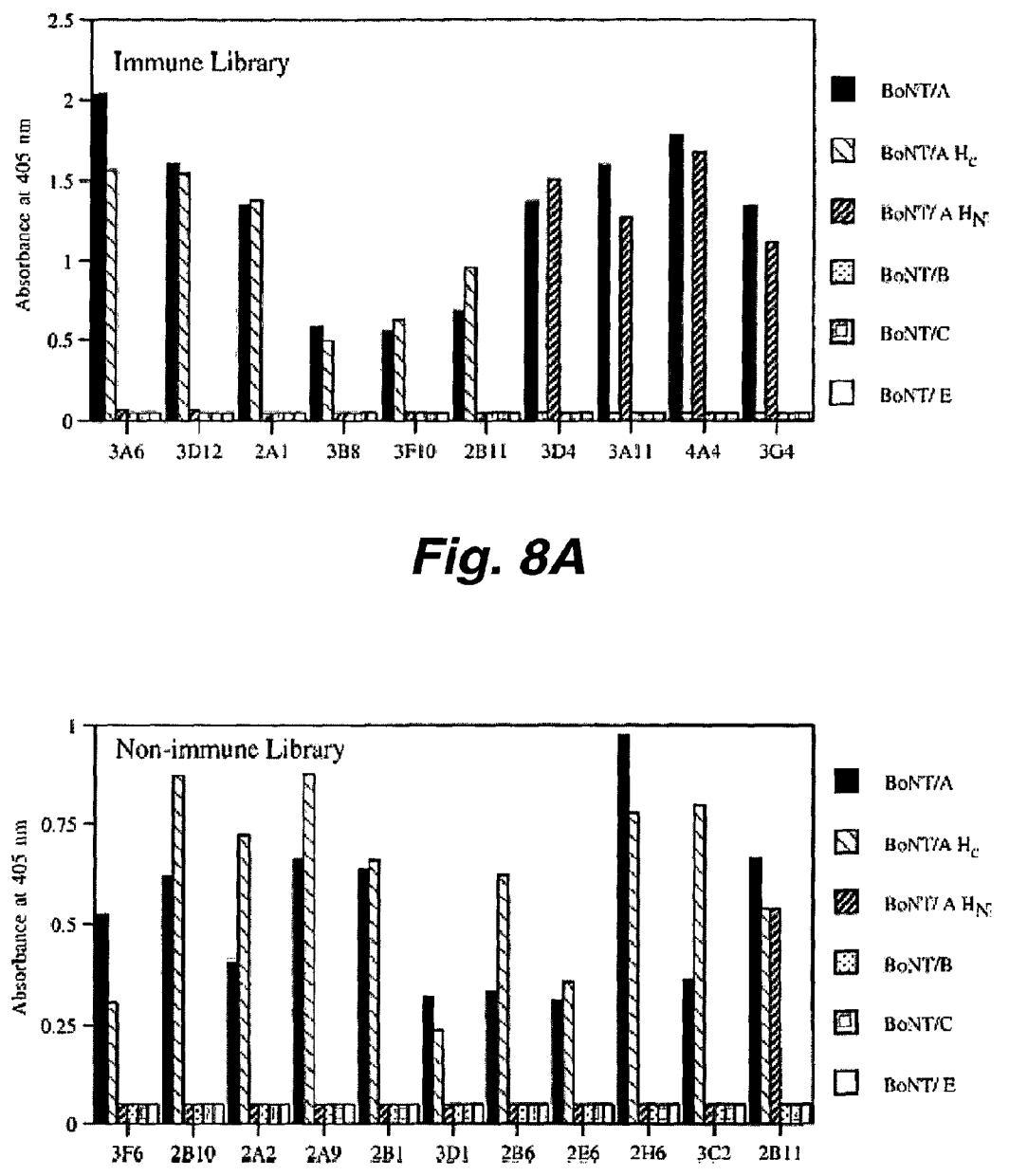

The fine specificity of each BoNT/A scFv was determined by ELISA on recombinant BoNT/A Hc and BoNT/A HN domains (FIG. 8). Of the 23 immune BoNT/A antibodies isolated after selection on toxin, 6 bound to BoNT/A Hc (3A6, 3D12, 2A1, 3B8, 3F10, 2B11), 4 bound to BoNT/A HN (3D4, 3A11, 4A4, 3G4) (FIG. 8A) and the remaining 13 antibodies presumably bound the light chain (Chen et al. (1997) *Infect Immun.*, 65:1626-1630). These findings suggest that immunization with botulinum toxoid directs the immune response towards the light chain, with fewer antibodies directed against the Hc or HN domains.

Selection of the immune library on BoNT/A Hc yielded only a single unique antibody (2A1), which was clonally related to toxin selected clones 3D12 and 3D6 (Table 9). When the $V_L$ gene usage of the six anti-Hc clones was analyzed, all were found to use the $V_\kappa 1$ gene family (Table 9), although the library contained ⅔ $V_\kappa$ and ⅓ VA light chain genes. Selection of the non-immune library on BoNT/A holotoxin yielded four antibodies, but none of these bound BoNT/A Hc. Selection of the library on BoNT/A Hc yielded 10 unique scFv, which used both V, or VA light chain genes (Table 9). Overall, only 50% of these scFv bound holotoxin, consistent with the observation that a significant portion of the Hc surface is buried in the holotoxin (Lacy et al. (1998) *Nat Struct Biol.*, 5:898-902). All scFv antibodies were serospecific and domain specific, with no cross reactivity observed except for clone 2B11 from the non-immune library, which bound to BoNT/A Hc and BoNT/A HN domain as determined by ELISA (FIG. 8B).

TABLE 9

CDR 3-sequences and affinities for human scFv antibodies isolated from immune and non-immune libraries, selected on BoNT/A and BoNT/A $H_C$.[a]

| Clone | Family | Segment | Diff from Genome | $V_H$ CDR3 |
|---|---|---|---|---|
| 2A9[b] | $V_H3$ | DP54 | 5 | GRGVN (SEQ ID NO: 54) |
| 2B1[b] | $V_H3$ | DP46 | 0 | NGDPEAFDY (SEQ ID NO: 55) |
| 2H6[b] | $V_H3$ | DP47 | 6 | ALQSDSPYFD (SEQ ID NO: 56) |
| 3C2[b] | $V_H3$ | DP46 | 2 | DLAIFAGNDY (SEQ ID NO: 57) |
| 2B6[b] | $V_H3$ | DP47 | 3 | VGVDRWYPADY (SEQ ID NO: 58) |
| 3F6[c] | $V_H3$ | DP47 | 2 | DLLDGSGAYFDY (SEQ ID NO: 59) |
| 2A2[b] | $V_H3$ | DP46 | 0 | DLDYGGNAGYFDL (SEQ ID NO: 60) |
| 2B10[b] | $V_H3$ | DP46 | 0 | DLDYGGNAGYFDL (SEQ ID NO: 61) |
| 2E6[b] | $V_H3$ | DP46 | 0 | DYTANYYYYGMDV (SEQ ID NO: 62) |
| 3D1b | $V_H3$ | DP47 | 7 | DLGYGSGTSSYYLDY (SEQ ID NO: 63) |

| | Non-immune library Light Chain | | | $V_L$ CDR3 |
|---|---|---|---|---|
| 2A9[b] | Vκ1 | L12A | 6 | QQANSFPRT (SEQ ID NO: 64) |
| 2B1[b] | Vκ1 | L1 | 11 | LQDYNGWT (SEQ ID NO: 65) |
| 2H6[b] | Vλ3 | DPL16 | 7 | NSRDSSGNHVV (SEQ ID NO: 66) |
| 3C2[b] | Vλ3 | DPL16 | 9 | KSRDSRGNHLAL (SEQ ID NO: 67) |
| 2B6[b] | Vλ1 | L12A | 5 | QQYHTISRT (SEQ ID NO: 68) |

TABLE 9-continued

CDR 3-sequences and affinities for human scFv antibodies isolated from immune and non-immune libraries, selected on BoNT/A and BoNT/A $H_C$.[a]

| | | | | |
|---|---|---|---|---|
| 3F6[c] | Vλ3 | DPL16 | 3 | NSRDSSGNHVV (SEQ ID NO: 69) |
| 2A2[b] | Vλ3 | DLP16 | 10 | HSRDSSVTNLD (SEQ ID NO: 70) |
| 2B10[b] | Vλ3 | DPL16 | 4 | NSRDSSGNHQV (SEQ ID NO: 71) |
| 2E6[b] | Vλ2 | DPL12 | 14 | NSRDSSGVV (SEQ ID NO: 72) |
| 3D1[b] | Vλ3 | DPL16 | 5 | NSRDSSGNHVV (SEQ ID NO: 73) |

Immune Library Heavy Chain

| Clone | Family | Segment | Diff from Genome | $V_H$ CDR3 |
|---|---|---|---|---|
| 3B8[c] | $V_H$1 | V1-2 | 10 | LATYYYFGLDV (SEQ ID NO: 74) |
| 3F10[c] | $V_H$1 | V1-2 | 10 | LATYYYFGLDV (SEQ ID NO: 75) |
| 2B11[c] | $V_H$1 | DP10 | 11 | GPWELVGYFDS (SEQ ID NO: 76) |
| 3A6c | $V_H$3 | DP50 | 18 | DPDWLLWGDRGALDV (SEQ ID NO: 77) |
| 3D12[c] | $V_H$3 | DP50 | 13 | EPDWLLWGDRGALDV (SEQ ID NO: 78) |
| 2A1[b] | $V_H$3 | DP50 | 14 | EPDWLLWGDRGALDV (SEQ ID NO: 79) |

Immune Library Light Chain

| Clone | Family | Segment | Diff from Genome | $V_L$ CDR3 |
|---|---|---|---|---|
| 3B8[c] | Vκ1 | DPK7 | 12 | QQYNSYVYT (SEQ ID NO: 80) |
| 3F10[c] | Vκ1 | DPK8 | 10 | QQLNSYPLT (SEQ ID NO: 81) |
| 2B11[c] | Vκ1 | L12 | 11 | QQLISYPLT (SEQ ID NO: 82) |
| 3A6[c] | Vκ1 | L12 | 8 | QHYNTYPYT (SEQ ID NO: 83) |
| 3D12[c] | Vκ1 | L12 | 10 | QHYNTYPYT (SEQ ID NO: 84) |
| 2A1[b] | Vκ1 | L12 | 4 | QHYNTYPYT (SEQ ID NO: 85) |

[a]Human germline VH, Vκ and Vλ segments have been assigned as detailed in the V-BASE database (MRC Centre for Protein Engineering, Cambridge, UK). Listed clones, with identical VH or VL CDR 3 regions, showed different CDR 1, CDR 2 and framework regions, as indicated by their differences from the germline genes; accession can be made through GenBank with nos. AF090405-AF090420.
[b]Library selected on BoNT/A.
[c]Library selected on BoNT/A HC.

Epitope Mapping of BoNT/A Hc Specific Antibody Fragments

BoNT/A Hc binding scFv were epitope mapped to determine the number of non-overlapping epitopes recognized. Epitope mapping was performed using surface plasmon resonance in a BIACORE™ studying pairs of scFv at concentrations resulting in near saturation of the chip surface and at least 100RU of scFv bound. The amount of scFv bound was determined for each member of a pair, and then the two scFv were mixed together to give a final concentration equal to the concentration used for measurements of the individual scFv. Antibodies recognizing identical epitopes showed minimal increase in RU bound when injected together (FIG. 9A), while scFv recognizing different epitopes showed an additive increase in RU (FIG. 9B). As depicted in Tables 2 and 3, scFv 3A6, 3D12 and 2A1, referred to as cluster I, share high homology of the $V_H$ and $V_L$ gene segments (DP 50 and L12, respectively) and recognize overlapping epitopes. They differ in sequence only by mutations in the heavy and light chain genes introduced by somatic mutations. The scFv 3B8 and 3F10, referred to as cluster II, form a second set of antibodies binding to a different epitope compared to cluster I. Clone 2B11, representing a possible unique epitope, could not be analyzed due to poor expression levels. When scFv antibodies derived from the non-immune library were analyzed, we found that all bound to unique epitopes, referred to as clusters III-XI as depicted in Table 3. Members of the non-immune library (clusters III-XI) showed no overlapping binding with members of the immune library (clusters I and II). The epitopes recognized by both the immune and non-immune scFv do not overlap with the epitopes bound by two previously reported murine scFv, C25 and S25 (Amersdorfer et al. (1997) *Infect. Immun.,* 65:3743-3752).

Kinetic Measurements and Neutralization Assay

The $k_{on}$ and $k_{off}$ were measured using surface plasmon resonance in a BIACORE™ and used to calculate the equilibrium dissociation constant. The scFv selected from the immune library had $K_d$'s of $3.69\times10^{-8}$ and $7.8\times10^{-9}$ M, values comparable to those reported for monoclonal IgG produced from hybridomas (Foote and Milstein (1991) Nature, 352:530-532) (Table 10). Non-immune scFv had lower Kd's ranging from $4.6\times10^{-7}$ to $2.61\times10^{-8}$M. To determine the ability of scFv to neutralize toxin induced neuroparalysis, in vitro studies were performed on one representative member from each epitope cluster using phrenic nerve-hemidiaphragm preparations. Values were reported in time to 50% twitch reduction for BoNT/A alone and in the presence of $2.0\times10^{-8}$M scFv. As shown in Table 10 and FIGS. 10A and 10B, a significant difference in neutralization of the different anti-BoNT/A $H_C$ scFvs were found, depending on which library was used. From the immune library, 3D12 (cluster I) significantly prolonged the time to neuroparalysis 1.5-fold, whereas 3F10 (cluster II) exhibited no effect on toxin neutralization. Representatives of the non-immune library (clusters III-XI) showed no protective effect in the hemidiaphragm assay, even after combination of all members of clusters III-XI at a final concentration of $1.8\times10^{-7}$ M. When using a combination of 3D12 (cluster I) with a previous isolated murine scFv, C25 (Amersdorfer et al. (1997) *Infect. Immun.,* 65:3743-3752), time to paralysis increased significantly to 3.2-fold, demonstrating a synergistic effect on toxin neutralization. We observed similar synergy with murine scFv S25 and 3D12 (data not shown).

TABLE 10

Affinities, binding kinetics, and in vitro toxin neutralization results of scFv selected from phage antibody libraries.

| Clone | Cluster | $K_d$ (M)[a] | $k_{on}$ (×10^5) (Ms)$^{-1}$ | $k_{off}$ (×10$^{-3}$s$^{-1}$) | Paralysis Time[b] |
|---|---|---|---|---|---|
| *Immune Library* | | | | | |
| 3D12[c] | I | $3.69 \times 10^{-8}$ | 0.13 | 0.50 | $85 \pm 5.0$[d] |
| 3F10[c] | II | $7.80 \times 10^{-9}$ | 0.80 | 0.62 | $55 \pm 5.0$[e] |
| *Non-Immune Library* | | | | | |
| 2B10[f] | III | $1.29 \times 10^{-7}$ | 5.57 | 71.6 | $62.3 \pm 6.7$[e] |
| 2E6[f] | IV | $1.93 \times 10^{-7}$ | 1.19 | 23.0 | $60.9 \pm 8.2$[e] |
| 2H6[f] | V | $3.86 \times 10^{-8}$ | 2.20 | 8.50 | $63.0 \pm 5.0$[e] |
| 2B1[f] | VI | $1.07 \times 10^{-7}$ | 0.83 | 8.88 | $58.4 \pm 4.0$[e] |
| 2A9[f] | VII | $2.61 \times 10^{-8}$ | 0.25 | 0.66 | $71.0 \pm 3.0$[e] |
| 2B6[f] | VIII | $7.15 \times 10^{-8}$ | 1.09 | 7.80 | $61.9 \pm 5.0$[e] |
| 3D1[f] | IX | $4.60 \times 10^{-7}$ | 1.31 | 60.3 | $58.3 \pm 3.8$[e] |
| 3F6[e] | X | $6.60 \times 10^{-8}$ | 4.69 | 30.9 | $60.4 \pm 3.6$[e] |
| 3C2[f] | XI | $3.90 \times 10^{-8}$ | 2.10 | 82.0 | $61.9 \pm 4.8$[e] |
| *Murine Library* | | | | | |
| S25 | XII | $7.30 \times 10^{-8}$ | 0.11 | 0.82 | $85 \pm 10$[d] |
| C25 | XIII | $1.10 \times 10^{-9}$ | 3.0 | 0.33 | $151 \pm 12$[d] |
| *Combination* | | | | | |
| C25 + S25 | | | | | $218 \pm 22$[g] |
| C25 + 3D12 | | | | | $179 \pm 2.3$[d] |
| Non-immune scFv (Clusters III-XI) | | | | | $65 \pm 2.3$[g] |
| BoNT/A pure toxin (control) | | | | | $56 \pm 3.8$ |

[a] The variables kon and koff were measured by surface plasmon resonance and Kd calculated as koff/kon.
[b] Time (min) to 50% twitch reduction in mouse hemidiaphragm assay using 20 nM scFv + 20 pM BoNT/A, compared to time for BoNT/A alone. Each value is the mean ± S.E.M. of at least three observations.
[c] Library selected on BoNT/A.
[d] $P < 0.01$ compared to BoNT/A.
[e] Not significant.
[f] Library selected on BoNT/A HC.
[g] $P < 0.01$ compared to BoNT/A HC.

Discussion

We previously demonstrated that immunization of mice with the recombinant binding domain of BoNT/A Hc directs the immune response towards generation of antibodies which bind epitope(s) involved in Hc binding to presynaptic toxin receptors (Amersdorfer et al. (1997) *Infect. Immun.*, 65:3743-3752). These experiments indicated that neutralization of toxin by scFv could be correlated to both scFv affinity and ability to compete with the holotoxin for receptor binding sites. Here we have carried out a more systematic approach by using immune and non-immune phage display libraries to map human humoral immune and non-immune responses to BoNT/A. The source of antibody genes for the two antibody libraries were (a) PBL of a human volunteer immunized with pentavalent toxoid (A-E) and (b) non-immune peripheral blood lymphocytes and spleenocytes. One limitation of this approach is the extent of which one immune human donor used for these studies represents broad genetic diversity generated upon exposure to botulism. The fact that the humoral immune response in mice and human resulted in a rather limited number of protective epitopes, suggests significant conservation of antigenic epitopes conferring protection. The selection procedure involved panning both combinatorial libraries against four immobilized botulinum neurotoxins, serotypes A, B, C, and E. After three to four panning cycles, antibodies against each serotype were obtained from both libraries, with decreasing frequency in this order, BoNT/A, BoNT/B, BoNT/C and BoNT/E. Similar frequency of binders was also observed for the non-immune library, with the exception of BoNT/B. These results correlate with the findings of Siegel (Siegel (1989) *J Clin Microbiol.*, 26:2351-2356), where they studied serum specimens from 25 human recipients of botulinum pentavalent toxoid. Immunogenicity of the various serotypes was determined by a mouse serum neutralization bioassay—serotype A ranged between 5.7 and 51.6 IU/ml, followed by serotype B from 0.78 to 18 IU/ml and serotype E, from 0.61 to 10 IU/ml.

Human immunization with toxoid resulted in production of antibodies directed largely against the toxin light chain, with fewer antibodies binding Hc. Similar results were observed after immunization of mice with BoNT/A Hc followed by holotoxin boosts. Since antibody neutralization activity results largely from blockade of cellular receptor binding by Hc, these analyses indicate that an Hc vaccine will be more protective than a toxin based vaccine, as more Hc antibodies are generated. Human immune Hc scFv recognized at least two non-overlapping epitopes. The scFv binding one of these epitopes (cluster I) could neutralize toxin in vitro. Potency of toxin neutralization increased when scFv binding cluster I were combined with immune mouse scFv binding either one of two non-overlapping Hc epitopes. This result suggests that Hc docks with either multiple cellular receptors, or docking occurs over a broad surface area (Mullaney et al. (2001) *Infect Immun.*, 69:6511-6514).

The repertoire of human scFv recognizing Hc was extended to a range of other epitopes (clusters III-XI) by selecting a large non-immune library on BoNT/A. Interestingly, this result is consistent with the concept that the primary immune repertoire contains antibodies capable of recognizing much of the solvent accessible area of an antigen, but that immunization directs this recognition to a limited number of immunodominant epitopes. All of the antibodies obtained from the non-immune library, however, were directed against non-neutralizing epitopes (or at least did not neutralize toxin in vitro). One explanation for the failure of neutralization could be due to low affinity of the antibodies for the Hc domain (e.g. 2B10, 2E6, 2B1, 3D1), ranging from 107 to 460 nM compared to the high affinity interaction of the toxin to its receptor(s), which is 0.3-2.3 nM (Schengrund (1999) *J Toxicol Toxin Rev.*, 18:35-44).

In conclusion, we report here the successful isolation of specific human antibodies toward botulinum neurotoxins and their subdomains using combinatorial libraries prepared from immune and non-immune human donors. The use of phage display to screen the antibody repertoire of any person with infectious diseases or pathogens allows us to access a very large pool of human monoclonal antibodies with therapeutic and research potential.

Example 4

Neutralizing Anti-BoNT/A Antibodies Evolved for Greater Affinity

Humanized C25 (HuC25) was subjected to directed evolution to increase binding affinity. Affinity improved versions of HuC25 include AR1 and AR2 (see e.g., Tables 11 and 12). In addition, affinity HuC25 was also engineered to bind more tightly to the A2 version of the A toxin. WR1(V) and WR1(T) (see e.g., Table 11) are HuC25 derivatives that tightly to the A2 version of A toxin improved versions of HuC25 and are thus cross-reactive for two different types of A toxin (A1 and A2). We have in vivo mouse data that AR1 is about twice as potent in mice in preventing intoxication than HuC25, so affinity is clearly important.

3D12, a fully human neutralizing antibody that synergizes with C25 and its related antibodies (e.g. huC25, AR1, AR2, etc.) was engineered to increase affinity. Three mutants are listed tin Table 11 (3-1, 3-8, 3-10) that bind both A1 and A2 toxin more than 10 times tighter than wild type 3D12. We believe improved binding translates into improved neutralization.

ING-1 is an antibody that is derived from a phage library selected on A2 toxin that cross-reacts with both toxins (A1 and A2) with good affinity.

TABLE 11 amino acid sequences for affinity matured and/or modified antibodies.

Heavy Chains

| Clone | Framework 1 | CDR1 | Framework 2 | CDR2 |
|---|---|---|---|---|
| huC25 | QVQLQESGGGLVQPGGSLRLSCAASGFTFS (SEQ ID NO: 86) | DYYMY (SEQ ID NO: 87) | WVRQAPGKGLEWVA (SEQ ID NO: 88) | TISDGGSYTYYPDSVKG (SEQ ID NO: 89) |
| Ar1 | QNQLQESGGGLVQPGGSLRLSCAASGFTFS (SEQ ID NO: 90) | DYYMY (SEQ ID NO: 91) | WVRQAPGKGLEWVA (SEQ ID NO: 92) | TISDGGSYTYYPDSVKG (SEQ ID NO: 93) |
| Ar2 | QVQLQESGGGLVQPGGSLRLSCAASGFTFS (SEQ ID NO: 94) | DHYMY (SEQ ID NO: 95) | WVRQAPGKGLEWVA (SEQ ID NO: 96) | TISDGGSYTYYPDSVKG (SEQ ID NO: 97) |
| WR1(V) | QVQLQESGGGLVQPGGSLRLSCAASGFTSS (SEQ ID NO: 98) | DHYMY (SEQ ID NO: 99) | WVRQAPGKGLEWVA (SEQ ID NO: 100) | TISDGGDYTYYPDSVKG (SEQ ID NO: 101) |
| WR1(T) | QVQLQESGGGLVQPGGSLRLSCAASGFTSS (SEQ ID NO: 102) | DHYMY (SEQ ID NO: 103) | WVRQAPGKGLEWVA (SEQ ID NO: 104) | TISDGGSYTYYPDSVKG (SEQ ID NO: 105) |
| 3D12 | QVQLVQSGGGVVHPGRSLKLSCAGSGFTFS (SEQ ID NO: 106) | DYDMH (SEQ ID NO: 107) | WVRQAPGLGLEWVA (SEQ ID NO: 108) | VMGFDGYEKYSAESVKG (SEQ ID NO: 109) |
| 3-1 | QVQLVQSGGGVVHPGRSLKLSCAGSGFTFS (SEQ ID NO: 110) | DYDMH (SEQ ID NO: 111) | WVRQAPGKGLEWVA (SEQ ID NO: 112) | VMWFDGTEKYSAESVKG (SEQ ID NO: 113) |
| 3-8 | QVQLVQSGGGVVHPGRSLKLSCAGSGFTFS (SEQ ID NO: 114) | DYDMH (SEQ ID NO: 115) | WVRQAPGKGLEWVA (SEQ ID NO: 116) | VIWFDGTEKYSAESVKG (SEQ ID NO: 117) |
| 3-10 | QVQLVQSGGGVVHPGRSLKLSCAGSGFTFS (SEQ ID NO: 118) | DYDMH (SEQ ID NO: 119) | WVRQAPGKGFEWVA (SEQ ID NO: 120) | VMWFDGTEKYSAESVKG (SEQ ID NO: 121) |
| ING1 | QVQLQQSGGGLVQPGGSLRLSCAASGFTFS (SEQ ID NO: 122) | NYAMT (SEQ ID NO: 123) | WVRQAPGKGLEWVS (SEQ ID NO: 124) | SISVGGSDTYYADSVKG (SEQ ID NO: 125) |

Heavy Chains

| Clone | Framework 3 | CDR3 | Framework 4 |
|---|---|---|---|
| huC25 | RFTISRDNSKNYLYLQMNSLRAEDTAMYYCSR (SEQ ID NO: 126) | YRYDDAMDY (SEQ ID NO: 127) | WGQGTLVTVSS (SEQ ID NO: 128) |
| Ar1 | RFTISRDNSKNTLYLQMNSLRAEDTAIYYCSR (SEQ ID NO: 129) | YRYDDAMDY (SEQ ID NO: 130) | WGQGTLVTVSS (SEQ ID NO: 131) |
| Ar2 | RFTTSRDNSKNTLYLQMNSLRAEDTAIYYCSR (SEQ ID NO: 132) | YRYDDAMDY (SEQ ID NO: 133) | WGQGTLVTVSS (SEQ ID NO: 134) |
| WR1(V) | RFTVSRDNSKNTLYLQMNSLRAEDTAIYYCSR (SEQ ID NO: 135) | YRYDDAMDY (SEQ ID NO: 136) | WGQGTLVTVSS (SEQ ID NO: 137) |
| WR1(T) | RFTTSRDNSKNTLYLQMNSLRAEDTAIYYCSR (SEQ ID NO: 138) | YRYDDAMDY (SEQ ID NO: 139) | WGQGTLVTVSS (SEQ ID NO: 140) |
| 3D12 | RFTISRDNSKNTLFLQMNSLRADDTAVYYCAR (SEQ ID NO: 141) | EPDWLLWGDRGALDV (SEQ ID NO: 142) | WGQGTTVTVSS (SEQ ID NO: 143) |
| 3-1 | RFTISRDNSKNTLFLQMNSLRADDTAVYYCAR (SEQ ID NO: 144) | EPDWLLWGDRGALDV (SEQ ID NO: 145) | WGQGTTVTVSS (SEQ ID NO: 146) |
| 3-8 | RFTISRDNSKNTLFLQMNSLRADDTAVYYCAR (SEQ ID NO: 147) | EPDWLLWGDRGALDV (SEQ ID NO: 148) | WGQGTTVTVSS (SEQ ID NO: 149) |
| 3-10 | RFTISRDNSKNTLFLQMNSLRADDTAVYYCAR (SEQ ID NO: 150) | EPDRLLWGDRGALDV (SEQ ID NO: 151) | WGQGTTVTVSS (SEQ ID NO: 152) |
| ING1 | RFTVSRDNSKNTLLLQMNSLRAEDTAVYYCAK (SEQ ID NO: 153) | VRTKYCSSLSCFAGFDS (SEQ ID NO: 154) | WGQGTLVTVSS (SEQ ID NO: 155) |

TABLE 11-continued amino acid sequences for affinity matured and/or modified antibodies.

Light Chains

| Clone | Framework 1 | CDR1 | Framework 2 | CDR2 |
|---|---|---|---|---|
| huC25 | EIVLTQSPATLSLSPGERATISC (SEQ ID NO: 156) | RASESVDSYGHSFMQ (SEQ ID NO: 157) | WYGGKPGQAPRLLIY (SEQ ID NO: 158) | RASNLEP (SEQ ID NO: 159) |
| Ar1 | EIVLTQSPATLSLSPGERATISC (SEQ ID NO: 160) | RASESVDSYGHSFMG (SEQ ID NO: 161) | WYQQKPGQAPRLLIY (SEQ ID NO: 162) | RASNLEP (SEQ ID NO: 163) |
| Ar2 | EIVLTQSPATLSLSPGERATISC (SEQ ID NO: 164) | RASESVDSYGHSFMQ (SEQ ID NO: 165) | WYQQKPGQAPRLLIY (SEQ ID NO: 166) | RASNLEP (SEQ ID NO: 167) |
| WR1(V) | EIVLTQSPATLSLSPGERATISC (SEQ ID NO: 168) | RASESVDSYGHSFMQ (SEQ ID NO: 169) | WYQQKPGQAPRLLIY (SEQ ID NO: 170) | RASNLEP (SEQ ID NO: 171) |
| WR1(T) | EIVLTQSPATLSLSPGERATISC (SEQ ID NO: 172) | RASESVDSYGHSFMQ (SEQ ID NO: 173) | WYQQKPGQAPRLLIY (SEQ ID NO: 174) | RASNLEP (SEQ ID NO: 175) |
| 3D12 | DIVMTQSPSTLSASVGRVTITC (SEQ ID NO: 176) | RASQSISSWLA (SEQ ID NO: 177) | WYQQKPGKAPKLLMY (SEQ ID NO: 178) | EASSLES (SEQ ID NO: 179) |
| 3-1 | DIVMTQSPSTLSASVGDRVTITC (SEQ ID NO: 180) | WASQSISSRLA (SEQ ID NO: 181) | WYQQKPGKAPKLLMY (SEQ ID NO: 182) | EATSLGS (SEQ ID NO: 183) |
| 3-8 | DIVMTQSPSTLSASVGDRVTITC (SEQ ID NO: 184) | RASQSISSWLA (SEQ ID NO: 185) | WYQQKPGKAPKLLMY (SEQ ID NO: 186) | GASSLGS (SEQ ID NO: 187) |
| 3-10 | DIVMTQSPSLTLSASVGDRVTITC (SEQ ID NO: 188) | RASQSISSWLA (SEQ ID NO: 189) | WYQQKPGKAPKLLMY (SEQ ID NO: 190) | EASSLGR (SEQ ID NO: 191) |
| ING1 | DIVMTQSPSSLSASVGDRVTITC (SEQ ID NO: 192) | RASQSISSYLN (SEQ ID NO: 193) | WYQQKPGKAPKL (SEQ ID NO: 194) | AASSLQS (SEQ ID NO: 195) |

Light Chains

| Clone | Framework 3 | CDR3 | Framework 4 |
|---|---|---|---|
| huC25 | GIPARFSGSGSGTDFTLTISSLEPEDFAVYYC (SEQ ID NO: 196) | QQSNEDPFT (SEQ ID NO: 197) | FGQGTKVEIKR (SEQ ID NO: 198) |
| Ar1 | GIPARFSGSGSGTDFTLTISSLEPEDFAVYYC (SEQ ID NO: 199) | QQGNEVPFT (SEQ ID NO: 200) | FGQGTKVEIKR (SEQ ID NO: 201) |
| Ar2 | FIPARFSGSGSGTDFTLTISSLEPEDFAVYYC (SEQ ID NO: 202) | QQGNEVPFT (SEQ ID NO: 203) | FGQGTKVEIKR (SEQ ID NO: 204) |
| WR1(V) | GIPARGSGSGSGTDFTLTISSLEPEDFAVYYC (SEQ ID NO: 205) | QQGNEVPFT (SEQ ID NO: 206) | FGQGTKVEIKR (SEQ ID NO: 207) |
| WR1(T) | GIPARFSGSGSGTDFTLTISSLEPEDFAVYYC (SEQ ID NO: 208) | QQGNEVPFT (SEQ ID NO: 209) | FGQGTKVEIKR (SEQ ID NO: 210) |
| 3D12 | GVPSRFSGSGSGTEFTLTISSLQPDDFAAYYC (SEQ ID NO: 211) | QHYNTYPYT (SEQ ID NO: 212) | FGQGTKLEIKR (SEQ ID NO: 213) |
| 3-1 | GVPSRFSGSGSGTEFTLTISSLQPDDFAAYYC (SEQ ID NO: 214) | QHYDTYPYT (SEQ ID NO: 215) | FGQGTKLEIKR (SEQ ID NO: 216) |
| 3-8 | GVPSRFSGSGSGTEFTLTISSLHPDDFAAYYC (SEQ ID NO: 217) | QHYNTYPYT (SEQ ID NO: 218) | FGQGTKLEIKR (SEQ ID NO: 219) |
| 3-10 | GVPSRFSGSGSGTEFTLTISSLQPDDFAAYYC (SEQ ID NO: 220) | QHYSTYPYT (SEQ ID NO: 221) | FGQGTKLEIKR (SEQ ID NO: 222) |
| ING1 | GVPSRFSGSGSGTDFTLTISSLQPEDFATYYC (SEQ ID NO: 223) | QQSYSTPRTT (SEQ ID NO: 224) | FGGGTKVDIKR (SEQ ID NO: 225) |

Sequence for complete heavy chain is heavy chain framework 1 + CDR1 + framework 2 + CDR2 + framework 3 + CDR3 + framework 4.
Sequence for complete light chain is light chain framework 1 + CDR1 + framework 2 + CDR2 + framework 3 + CDR3 + framework 4.

TABLE 12

Affinity of antibodies on A1 and A2 toxins.

| Antibody | $K_D$ on Hall (A1) toxin | $K_D$ on Honey (A2) toxin |
|---|---|---|
| HuC25 | 1.24 nM | 250 nM |
| AR1 | 200 pM | 100 nM |
| AR2 | 47 pM | ND |
| WR1 (V) | 450 pM | 9.0 nM |
| WR1 (T) | 310 pM | 3.7 nM |
| 3D12 | 940 pM | 2.2 nM |
| 3D12.3-1 (RAZ1) | 17 pM | 70 pM |
| 3D12.3-8 | 21 pM | 67 pM |
| 3D12.3-10 | 28 pM | 81 pM |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

---

What is claimed is:

1. An isolated antibody, or antigen-binding fragment thereof, that specifically binds to an epitope of Botulinum neurotoxin type A, wherein the antibody or antigen-binding fragment comprises:
   a) a VL CDR1 comprising the amino acid sequence of SEQ ID NO:165;
   b) a VL CDR2 comprising the amino acid sequence of SEQ ID NO:167;
   c) a VL CDR3 comprising the amino acid sequence of SEQ ID NO:203; and
   d) VH CDRs comprising:
      i) a VH CDR1 comprising the amino acid sequence of SEQ ID NO:91;
      ii) a VH CDR2 comprising the amino acid sequence of SEQ ID NO:93; and
      ii) a VH CDR3 comprising the amino acid sequence of SEQ ID NO:130;
   or
      i) a VH CDR1 comprising the amino acid sequence of SEQ ID NO:95;
      ii) a VH CDR2 comprising the amino acid sequence of SEQ ID NO:97; and
      ii) a VH CDR3 comprising the amino acid sequence of SEQ ID NO:133.

2. The isolated antibody or antigen-binding fragment of claim 1, wherein said antibody is a single chain Fv (scFv).

3. The isolated antibody or antigen-binding fragment of claim 1, wherein said antibody is an IgG.

4. The isolated antibody or antigen-binding fragment of claim 1, wherein said antibody is a Fab.

5. The isolated antibody or antigen-binding fragment of claim 1, wherein said antibody is a (Fab')$_2$.

6. The isolated antibody or antigen-binding fragment of claim 1, wherein said antibody is a (scFv')$_2$.

7. The isolated antibody or antigen-binding fragment of claim 6, wherein said antibody is a fusion protein of two scFv fragments.

8. A method of specifically binding a botulinum neurotoxin type A (BoNT/A), said method comprising contacting said botulinum neurotoxin type A with an anti-botulinum neurotoxin type A (anti-BoNT/A) antibody or antigen-fragment binding fragment according to claim 1, said antibody or antigen-fragment binding fragment having a specificity and affinity such that it specifically binds to said botulinum neurotoxin type A.

9. The method of claim 8, wherein said antibody binds both an A1 and A2 toxin.

10. The method of claim 8, further comprising contacting said botulinum neurotoxin type A with a second anti-botulinum neurotoxin type A (anti-BoNT/A) antibody or antigen-fragment binding fragment according to claim 1, said antibody or antigen-fragment binding fragment having a specificity and affinity such that it specifically binds to said botulinum neurotoxin type A, wherein said second anti-botulinum neurotoxin type A (anti-BoNT/A) antibody or antigen-fragment binding fragment binds to a different epitope than said first anti-botulinum neurotoxin type A (anti-BoNT/A) antibody or antigen-fragment binding fragment.

11. A composition comprising a plurality of anti-botulinum neurotoxin antibodies or antigen-binding fragments, wherein each antibody or antigen-binding fragment is specific for a different epitope of a botulinum neurotoxin, and wherein said plurality comprises an antibody of claim 1.

12. The composition of claim 11, wherein said composition comprises a first antibody or antigen-binding fragment that binds an A1 toxin and a second antibody or antigen-binding fragment that binds an A2 toxin.

13. A method of specifically binding a botulinum neurotoxin, said method comprising contacting said neurotoxin with the composition of claim 11.

14. The isolated antibody or antigen-binding fragment of claim 1, wherein said antibody comprises a variable heavy ($V_H$) comprising complementarity determining regions comprising the amino acid sequence of $V_H$ CDR1 (SEQ ID NO: 95), $V_H$ CDR2 (SEQ ID NO: 97), and $V_H$ CDR3 (SEQ ID NO:133).

15. The isolated antibody or antigen-binding fragment of claim 1, wherein said antibody comprises a $V_H$ comprising complementarity determining regions comprising the amino acid sequence of $V_H$ CDR1 (SEQ ID NO: 91), $V_H$ CDR2 (SEQ ID NO: 93), and $V_H$ CDR3 (SEQ ID NO:130).

16. The isolated antibody or antigen-binding fragment of claim 1, wherein said antibody or antigen-binding fragment comprises a full length light chain comprising framework regions comprising the amino acid sequence of $V_L$ framework 1 (SEQ ID NO: 164), of $V_L$ framework 2 (SEQ ID NO: 166), of $V_L$ framework 3 (SEQ ID NO: 202), and of $V_L$ framework 4 (SEQ ID NO: 204).

17. The isolated antibody or antigen-binding fragment of claim 16, wherein said antibody or antigen-binding fragment comprises a variable heavy ($V_H$) comprising complementarity determining regions comprising the amino acid sequence of $V_H$ CDR1 (SEQ ID NO: 95), $V_H$ CDR2 (SEQ ID NO: 97), and $V_H$ CDR3 (SEQ ID NO:133).

18. The isolated antibody or antigen-binding fragment of claim 16, wherein said antibody or antigen-binding fragment comprises a $V_H$ comprising complementarity determining regions comprising the amino acid sequence of $V_H$ CDR1 (SEQ ID NO: 91), $V_H$ CDR2 (SEQ ID NO: 93), and $V_H$ CDR3 (SEQ ID NO:130).

19. The isolated antibody or antigen-binding fragment of claim 17, wherein said antibody or antigen-binding fragment comprises a $V_H$ comprising framework regions comprising the amino acid sequence of $V_H$ framework 1 (SEQ ID NO: 94), of $V_H$ framework 2 (SEQ ID NO: 96), of $V_H$ framework 3 (SEQ ID NO: 132), and of $V_H$ framework 4 (SEQ ID NO: 134).

20. The isolated antibody or antigen-binding fragment of claim 18, wherein said antibody or antigen-binding fragment comprises a $V_H$ comprising framework regions comprising the amino acid sequence of $V_H$ framework 1 (SEQ ID NO: 90), of $V_H$ framework 2 (SEQ ID NO: 92), of $V_H$ framework 3 (SEQ ID NO: 129), and of $V_H$ framework 4 (SEQ ID NO: 131).

21. An isolated antibody, or antigen-binding fragment thereof, that specifically binds to an epitope of Botulinum neurotoxin type A, wherein the antibody comprises a full-length light chain comprising:
  a $V_L$ CDR1 comprising the amino acid sequence of SEQ ID NO:165;
  a $V_L$ CDR2 comprising the amino acid sequence of SEQ ID NO:167;
  a $V_L$ CDR3 comprising the amino acid sequence of SEQ ID NO:203;
  a $V_L$ framework 1 comprising the amino acid sequence of SEQ ID NO: 164;
  a $V_L$ framework 2 comprising the amino acid sequence of SEQ ID NO:166;
  a $V_L$ framework 3 comprising the amino acid sequence of SEQ ID NO: 202; and
  a $V_L$ framework 4 comprising the amino acid sequence of SEQ ID NO: 204.

22. A method of detecting a Botulinum neurotoxin (BoNT) in a biological sample, the method comprising:
  a) contacting the biological sample with the isolated antibody, or an antigen-binding fragment thereof, of claim 1; and
  b) detecting binding, if any, of the antibody to an epitope present in the sample.

* * * * *